US011597784B2

United States Patent
Sundell et al.

(10) Patent No.: US 11,597,784 B2
(45) Date of Patent: Mar. 7, 2023

(54) ENHANCED YIELD, STRUCTURAL CONTROL, AND TRANSPORT PROPERTIES OF POLYNORBORNENES FOR NATURAL GAS UPGRADING THROUGH MIZOROKI-HECK CROSS-COUPLINGS

(71) Applicant: Saudi Arabian Oil Company, Dhahran (SA)

(72) Inventors: Benjamin James Sundell, Arlington, MA (US); John Alden Lawrence, III, Cambridge, MA (US); Tatiana P. Headrick, Waltham, MA (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 288 days.

(21) Appl. No.: 16/834,926

(22) Filed: Mar. 30, 2020

(65) Prior Publication Data
US 2021/0324118 A1 Oct. 21, 2021

(51) Int. Cl.
| | |
|---|---|
| C08F 132/08 | (2006.01) |
| C08F 132/02 | (2006.01) |
| C08G 61/08 | (2006.01) |
| C07C 2/72 | (2006.01) |
| B01D 53/22 | (2006.01) |
| B01D 71/44 | (2006.01) |

(52) U.S. Cl.
CPC .......... *C08F 132/08* (2013.01); *B01D 53/228* (2013.01); *B01D 71/44* (2013.01); *C07C 2/72* (2013.01); *C08F 132/02* (2013.01); *C08G 61/08* (2013.01)

(58) Field of Classification Search
CPC .... C08F 232/00; C08F 232/04; C08F 232/06; C08F 32/00; C08F 32/04; C08F 32/06; C08F 132/00; C08F 132/04; C08F 132/06; C08F 132/08; C08G 61/08; C07C 2/72
See application file for complete search history.

(56) References Cited

U.S. PATENT DOCUMENTS

| | | | | |
|---|---|---|---|---|
| 4,412,044 | A * | 10/1983 | Takahashi | C08G 61/08 |
| | | | | 525/367 |
| 7,550,546 | B2 * | 6/2009 | Watanabe | C08F 32/08 |
| | | | | 526/256 |
| 9,896,527 | B2 * | 2/2018 | Sundell | C08G 61/08 |
| 10,029,207 | B2 | 7/2018 | Qiao et al. | |
| 2008/0011406 | A1 * | 1/2008 | Arai | C08F 210/02 |
| | | | | 156/87 |
| 2008/0033133 | A1 | 2/2008 | Watanabe | |
| 2011/0143260 | A1 | 6/2011 | Bell et al. | |
| 2012/0283404 | A1 * | 11/2012 | Knapp | C12P 7/16 |
| | | | | 526/242 |
| 2021/0198393 | A1 * | 7/2021 | Deng | C08F 4/7027 |
| 2021/0347935 | A1 * | 11/2021 | Beerman | B01J 31/2278 |

FOREIGN PATENT DOCUMENTS

| | | | | | |
|---|---|---|---|---|---|
| JP | 2003-252928 | A | * | 9/2003 | .............. C08F 16/14 |
| JP | 2009046614 | A1 | | 3/2009 | |
| JP | 2011-219396 | A | * | 11/2011 | ............... C07C 2/72 |
| KR | 101809493 | B1 | | 12/2017 | |
| WO | 2005061110 | A1 | | 7/2005 | |
| WO | 2009097322 | A1 | | 8/2009 | |

OTHER PUBLICATIONS

Arnauld, T.; Barrett, A.G.M.; Hopkins, B.T. Tetrahedron Letters 2002, 43, 1081-1083. (Year: 2002).*
Li, S.; Burns, A.B.; Register, R.A.; Bell, A. Macromol. Chem. Phys. 2012, 214, 2027-2033.*
Gringolts, M., et al. "New high permeable addition poly (tricyclononenes) with Si (CH3) 3 side groups. Synthesis, gas permeation parameters, and free volume." Macromolecules 43.17 (2010): 7165-7172.
Finkelshtein, E. Sh, et al. "Addition-type polynorbornenes with Si (CH3) 3 side groups: synthesis, gas permeability, and free volume." Macromolecules 39.20 (2006): 7022-7029.
Vaughn, Justin T., et al. "Reverse selective glassy polymers for C3+ hydrocarbon recovery from natural gas." Journal of Membrane Science 522 (2017): 68-76.
Sundell, Benjamin J., et al. "Alkoxysilyl functionalized polynorbornenes with enhanced selectivity for heavy hydrocarbon separations." Rsc Advances 6.57 (2016): 51619-51628.
Tetsuka, Hiroaki, Mamoru Hagiwara, and Shojiro Kaita. "Addition-type poly (norbornene) s with siloxane substituents: synthesis, properties and nanoporous membrane." Polymer journal 43.1 (2011): 97.
Aida, Fuyuki, et al. "Palladium-catalyzed 5-exo-Selective Reductive Mizoroki-Heck Reaction of Aryl Chlorides with 2, 5-Norbornadiene." Chemistry Letters 44.5 (2015): 715-717.
Alentiev, Dmitry A., et al. "Stereoselective synthesis and polymerization of Exo-5-trimethylsilylnorbornene." Journal of Polymer Science Part A: Polymer Chemistry 56.12 (2018): 1234-1248.
International Search Report and Written Opinion in Corresponding PCT Application No. PCT/US2021/024593 dated Jul. 2, 2021.
Arnaul T. et al.; ROMPgel—supported biphenyl and naphthalene: reagent for lithiation reactions with minimal purification; Tetrahedron Letters, Elseview, Amsterdam, NL, vol. 43, No. 6, Feb. 4, 2002; pp. 1081-1083.
Ho Kim Sung et al. Exploration of the versatility of ring opening metathesis polymerization: and approach for gaining access to low density polymeric aerogels, RSC Advances vol. 2, No. 23, Jan. 1, 2012, p. 8672; URL:https://pubs.rsc.org/en/content/articldf/2012/ra/c2ra21214e>.
Martin E. Speer et al.; Thianthrene-functionalized polynorbornenes as high-voltage materials for organic cathode-based dual-ion batteries; Chemical Communications, vol. 51, No. 83, Jan. 1, 2015.
Thakur Ashutosh et al: Cooperative catalysis by multiple active Centers of a half-titanocene catalyst integrated in polymer random coils; ACS Catalysis, vol. 9, No. 4; April 5, 20019.

(Continued)

*Primary Examiner* — Rip A Lee
(74) *Attorney, Agent, or Firm* — Leason Ellis LLP

(57) ABSTRACT

Gas separation membranes are provided and more particularly, a series of addition-type and ROMP type polynorbornenes with substituents derived from Mizoroki-Heck reactions are provided and have particular utility as gas separation membranes for natural gas upgrading.

15 Claims, 28 Drawing Sheets

(56) References Cited

OTHER PUBLICATIONS

Lai Holden W. H. et al.; Norbornyl bensocyclobutene ladder polymers: Conformation and microporosity; Journal of Polymer Science Part A: Polymer Chemistry, vol. 55, No. 18; May 15, 2017; <https://onlinelibrary.wiley.com/doi/full-xml/10.1002/pola.28640>.

* cited by examiner

ENHANCED YIELD, STRUCTURAL CONTROL, AND TRANSPORT PROPERTIES OF POLYNORBORNENES FOR NATURAL GAS UPGRADING THROUGH MIZOROKI-HECK CROSS-COUPLINGS

TECHNICAL FIELD

The present disclosure relates to gas separation membranes and more particularly, to a series of addition-type and ROMP type polynorbornenes with substituents derived from Mizoroki-Heck reactions that have particular utility as gas separation membranes for natural gas upgrading.

BACKGROUND

Natural gas (methane) is often found with substantial amounts of impurities that must be removed before pipeline distribution. Heavy hydrocarbon components, such as propane and butane, are valuable for energy production or chemicals manufacturing. Currently, hydrocarbons such as propane and butane are removed from natural gas by refrigeration technologies that condense these products out as liquids, where they are separated from natural gas. While effective, refrigeration technologies are relatively expensive and energetically intensive. An alternative technology to separate propane and butane from natural gas uses semipermeable polymeric membranes, which do not require costly cooling mechanisms and have a "free" energetic driving force—the high pressure/concentration gas feed.

Many gas separation membranes have been developed and commercialized to separate nitrogen from air, carbon dioxide from methane, and several other gas pairs. These membranes operate on the basis of diffusion selectivity, where smaller molecules permeate at a faster rate through the polymeric membrane. If these processes were applied towards the separation of propane and butane from methane, methane would permeate at a faster rate than propane or butane, which would necessitate costly recompression of the methane permeate before pipeline distribution. Therefore, a much more attractive separation involves a gas separation membrane that permeates the larger propane and butane at a more rapid rate compared to methane. Membranes that perform this separation have been studied and include the commercialized rubbery polydimethylsiloxane (PDMS) and its derivatives, highly glassy materials such as poly[1-(trimethylsilyl)-1-propyne] (PTMSP), polymers of intrinsic microporosity (PIMs), and certain polynorbornene derivatives (PNB). Polynorbornenes have generated high interest lately because they can demonstrate higher separation efficiencies compared to rubbery PDMS, though they don't suffer as much from the aging and collapse of free volume that are endemic in PTMSP and PIMs. Polynorbornenes have been regarded as intermediate materials between the rubbery and glassy polymers and may offer advantages compared to either, though they do present challenges that need to be overcome.

Polynorbornenes encompass a large family of polymers with several structural motifs that are often categorized based on the polymerization mechanism. Ring-opening metathesis polymerization (ROMP) is the most widely used and versatile technique to produce polynorbornenes, though these polymers have not exhibited exceptional performance as membranes for heavy hydrocarbon separations. Cationic polymerizations of polynorbornenes are also known, but often produce low molecular weight materials with poor mechanical properties and unknown gas separation characteristics. The most promising polynorbornenes have resulted from addition-type polymerizations that keep intact the bicyclic nature of the polynorbornene backbone, have high chain rigidity and glass transition temperatures, and have demonstrated superior heavy hydrocarbons separations compared to PDMS. The addition-type polynorbornenes face several important challenges: a general lack of diversity in substituent availability off the polynorbornene backbone, relatively low polymerization yields compared to the ROMP polynorbornenes, and a need to further improve hydrocarbon selectivities in natural gas upgrading. The work described in the present disclosure addresses and solves these challenges.

Further embodiments and the full scope of applicability of the present disclosure will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

SUMMARY

A process for forming a Mizoroki-Heck derived polynorbornene that is suitable for use as a gas separation membrane comprises the steps of:
  producing a substituted norbornene monomer by a Mizoroki-Heck coupling reaction in the presence of a catalyst; and
  polymerizing the substituted norbornene monomer to form the Mizoroki-Heck derived polynorbornene.

In one embodiment of the present disclosure, the substituted norbornene monomer comprises a 4-substituted norbornene monomer or a cyclic substituted norbornene monomer and the produced substituted norbornene monomers are further reacted in vinyl addition-type or ROMP-type polymerizations to obtain polynorbornenes, i.e., Mizoroki-Heck derived polynorbornenes (also referred to as Heck polynorbornenes).

Since the Mizoroki-Heck reaction produces norbornene monomers with substituents solely in the exo configuration, addition-type polymerizations of the exo substituted monomer feedstocks proceed with up to 100% yields, a large enhancement over previous routes, such as the Diels-Alder route.

The present Applicant has discovered that Mizoroki-Heck derived polynorbornenes show heightened mixed gas selectivities for butane/methane compared to both commercial PDMS and previously synthesized addition-type triethoxysilyl polynorbornene (TEA PNB).

The present Applicant has discovered that the Mizoroki-Heck derived polynorbornenes demonstrate unique solubility-selective gas permeation and that their $C_4H_{10}/CH_4$ mixed gas selectivities exceed alkoxysilyl based polynorbornenes and commercially used PDMS. In addition to thermal and structural characterization, XRD and computational studies confirmed the results of pure and mixed-gas transport testing, which show highly rigid polynorbornene membranes with favorably disrupted chain packing. In particular, a trimethylsilyl functionalized poly(tricyclononene) showed a regime of chain packing between 16.8-20.5 Å, mixed gas $C_4H_{10}$ permeabilities exceeding 5,000 Barrer, and $C_4H_{10}/CH_4$ selectivities up to 19.6.

BRIEF DESCRIPTION OF THE FIGURES

A more complete understanding of the invention and its many features and advantages will be attained by reference to the following detailed description and the accompanying drawing. It is important to note that the drawing illustrates only one embodiment of the present disclosure and therefore should not be considered to limit its scope.

FIG. 3(b) sets forth Mizoroki-Heck cross-coupling towards producing a cyclic substituted norbornene monomer (tricyclononene); FIG. 3(c) sets forth an addition polymerization of either 4-substituted or cyclic monomers in the presence of a palladium catalyst to produce high molecular weight polymer; and FIG. 3(d) sets forth a ring-opening metathesis polymerization (ROMP) of either 4-substituted or cyclic monomer in the presence of Grubbs' 1st generation catalyst to produce a high molecular weight polymer;

DETAILED DESCRIPTION OF CERTAIN EMBODIMENTS

Figure 1:
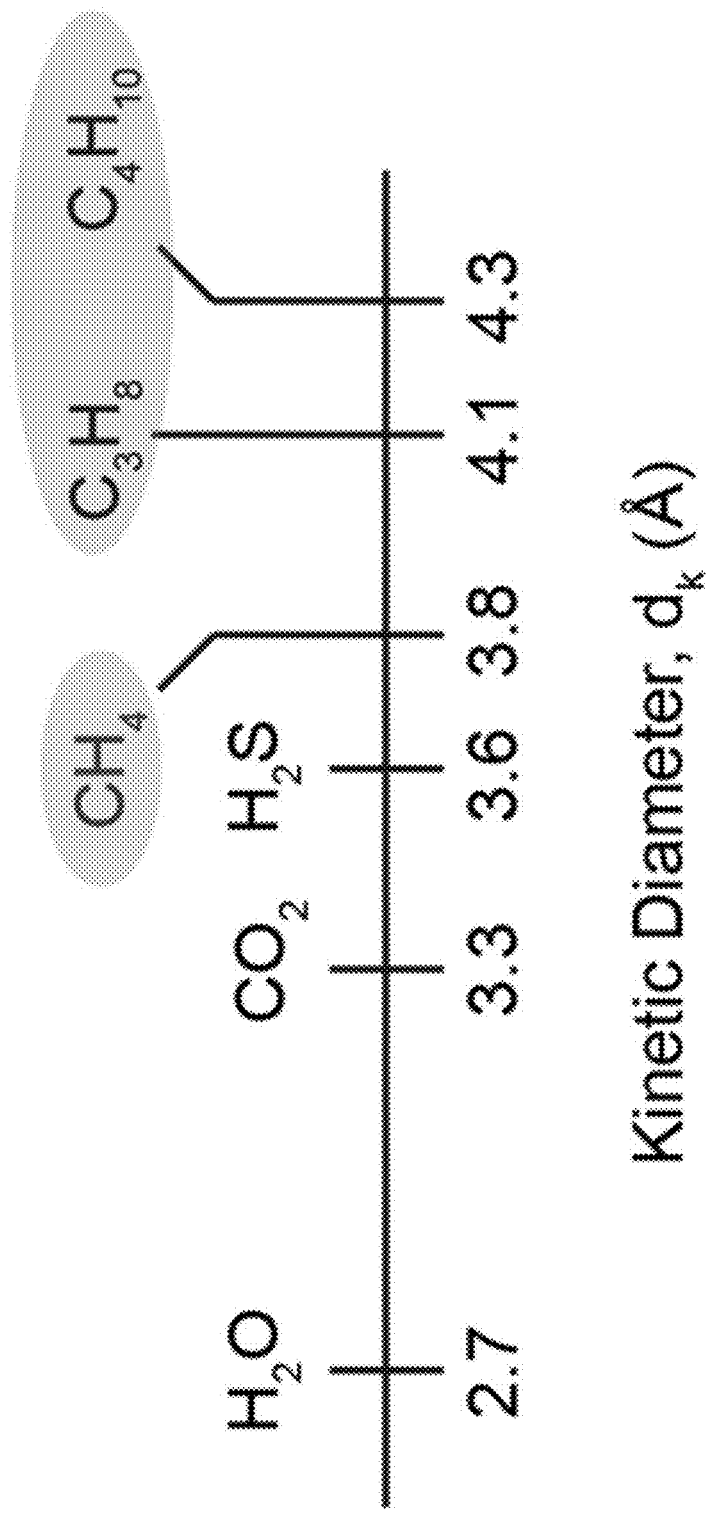
FIG. 1 sets forth kinetic diameters of several important gases in natural gas separations.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

In one aspect, the present disclosure describes the synthesis of substituted norbornene monomers through Mizoroki-Heck reactions, which may then be further reacted in vinyl addition-type or ROMP-type polymerizations to obtain polynorbornenes, i.e., Mizoroki-Heck derived polynorbornenes (also referred to as Heck polynorbornenes). The Heck polynorbornenes solve the aforementioned challenges with addition-type and ROMP-type polynorbornenes in the following ways:

(1) Heck polynorbornenes show heightened mixed gas selectivities for butane/methane compared to both commercial PDMS and previously synthesized addition-type triethoxysilyl polynorbornene (TEA PNB). In one example, a Heck derived polynorbornene had a C4/C1 selectivity of 19.6, compared to TEA-PNB with 18.5 and commercial PDMS with 13.9. Additionally, the stereoselective control of exo versus endo content has now been identified as a way of enhancing gas permeabilities. A recent report demonstrated higher gas permeabilities in pure exo derived ROMP and addition norbornenes compared to ROMP and addition norbornenes with mixtures of exo and endo content;

(2) Typical norbornene monomers employed in the synthesis of polymers for gas separation membranes are derived from Diels-Alder reactions that produce a mixture of norbornene stereoisomers, the exo and endo isomers. Furthermore, the Diels-Alder reaction typically results in a majority of the kinetically controlled endo configuration and much less of the thermodynamically favored exo configuration 4-substituted norbornene monomers with substituents in the endo position present steric interactions during the polymerization reaction that can block the coordination of the alkene to the transition metal catalyst, inhibiting the polymerization of these isomers. As a result, the presence of endo isomers in a norbornene monomer mixture can reduce polymerization yields by as much as 60% and also reduce resulting polymer molecular weights. Alternatively, the Mizoroki-Heck reaction typically produces norbornene monomers with substituents solely in the exo configuration. Addition-type polymerizations of the exo monomer feedstocks proceed with up to 100% yields and enhanced molecular weights, a large enhancement over previous routes; and (3) Historically, norbornene monomers used for addition-type polymerization in gas separations have been produced through limited reaction pathways. The Diels-Alder route, also known as a [4π+2π] cycloaddition, is perhaps the most commonly used. However, stereospecific [2σ+2σ+2π] cycloadditions through quadricyclanes are also known. These reactions proceed through cyclopentadiene or quadricyclane reacted with vinyl species, often bearing silane groups. Thus, the utility of these reactions has generally been limited by having the appropriate vinyl reagent available, which resulted in a reduced variety of substituents that could be introduced into the norbornene monomers. The Heck polynorbornenes proceed through the reaction between norbornadiene and aryl halides, particularly aryl bromides and aryl iodides, which are widely available from the diverse pool of building blocks for a variety of Pd-catalyzed coupling reactions, thereby greatly increasing the scope and selection of norbornene monomers available for addition-type polymerizations.

Gas Separation Membranes

As described herein, typical gas separation membranes operate based on diffusion selectivity, where gases with smaller kinetic diameters permeate through polymeric membranes at a faster rate compared to gases with a larger kinetic diameter. The gases most often referred to in the present disclosure, namely, methane, propane, and butane, are shown in FIG. 1 with their corresponding kinetic diameters listed therein.

Figure 2:
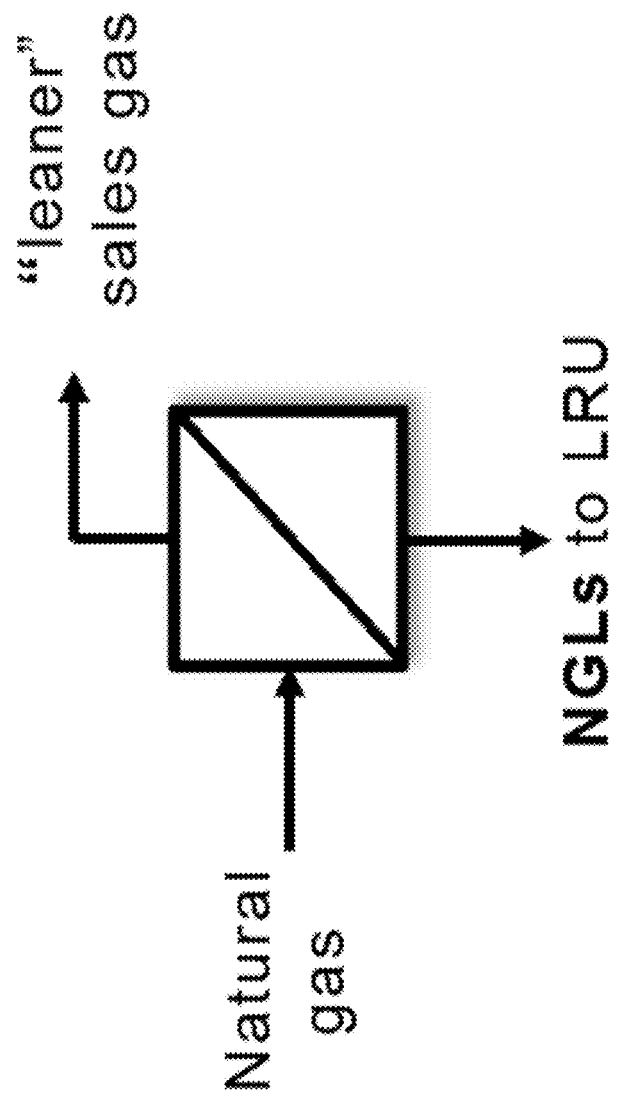
FIG. 2 is a schematic of an exemplary separation module where propane and butane permeate preferentially through a polymeric membrane compared to methane.

A diffusion selective membrane would permeate methane at a faster rate compared to propane and butane, whereas a more commercially attractive separation is shown in FIG. 2. In FIG. 2, a combination of methane (natural gas), propane, and butane enter the gas separation module (black box) at elevated pressures, methane is retained on the high pressure upstream interface and is delivered as "leaner" sales gas, and propane and butane permeate through the gas separation membrane (grey diagonal line) as lower pressure NGLs to the LRU (liquid recovery unit). This method avoids costly recompression of methane that would result from diffusion selective separations.

Typical polymeric membranes are incapable of the separation in FIG. 2 and will preferentially permeate methane compared to propane and butane. The present disclosure describes a series of novel polynorbornene structures capable of permeating propane and butane preferentially compared to methane, and with higher efficiencies compared to both commercialized PDMS and prior addition-type alkoxysilyl containing polynorbornenes (See, FIGS. 16 and 17 and their discussions).

Mizoroki-Heck Reaction

As is known, the Mizoroki-Heck reaction (also called the Heck reaction) is the chemical reaction of an unsaturated halide (or triflate) with an alkene in the presence of a base and a palladium catalyst (or palladium nanomaterial-based catalyst) to form a substituted alkene. The Mizoroki-Heck reaction is thus the palladium catalyzed cross-coupling reaction between alkenes, and aryl or vinyl halides (or triflates) to afford substituted alkenes. Typically, the Heck reaction includes an aryl moiety.

The Mizoroki-Heck reaction can be represented by:

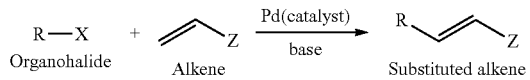

X = I, Br, OTf, Cl, etc.
Z = H, R, Ar, CN, CO, OR, OAc, NHAc, etc.

Heck Monomer

A Heck monomer refers to a substituted monomer synthesized through the Mizoroki-Heck reaction.

Mizoroki-Heck Derived Polymer

A Mizoroki-Heck derived polymer can be considered to be a polymer that is formed by the polymerization of a substituted monomer that is produced by the Mizoroki-Heck reaction.

Norbornene

A norbornene is a bridged cyclic hydrocarbon that consists of a cyclohexene ring with a methylene bridge between carbons 1 and 4. The molecule carries a double bond which induces significant ring strain and significant reactivity. Norbornene is made by a Diels-Alder reaction of cyclopentadiene and ethylene. Many substituted norbornenes can be prepared similarly. Related bicyclic compounds are norbornadiene, which has the same carbon skeleton but with two double bonds and norbornane which is prepared by hydrogenation of norbornene.

Polynorbornenes

Norbornenes are important monomers in ring-opening metathesis polymerizations (ROMP). Polynorbornenes exhibit high glass transition temperatures and high optical clarity. In addition to ROMP, norbornene monomers also undergo vinyl-addition polymerization and is a popular monomer for use in cyclic olefin polymers.

As set forth above, the present Applicant discovered that monomers (e.g., substituted norbornene monomers) synthesized through the Mizoroki-Heck reaction are capable of producing much higher yields (up to and including 100%) and heightened molecular weights in the polymerization processes compared to the traditional Diel-Alder reactions which typically results in monomer formation in a majority of the kinetically controlled endo configuration and much less of the thermodynamically favored exo configuration (that results from the Mizoroki-Heck reaction).

Synthesis of Substituted Norbornene Monomers through Mizoroki-Heck Reactions

Figure 3A:
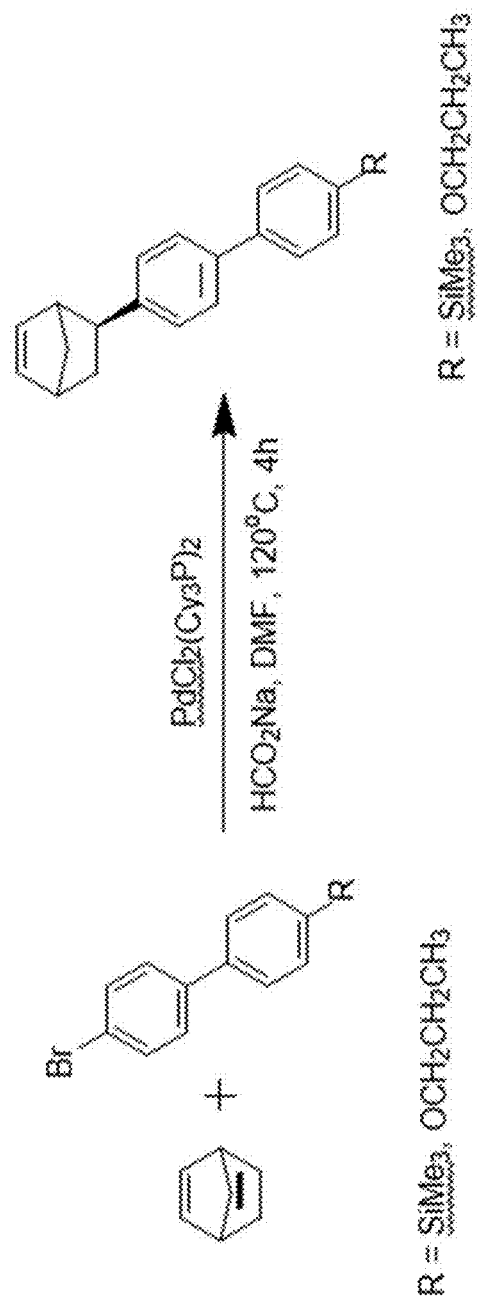
FIGS. 3(a) to 3(d) illustrate schemes for the synthesis of substituted norbornene monomers through Mizoroki-Heck reactions, which may then be further reacted in vinyl addition-type or ROMP-type polymerizations to obtain polynorbornenes (Heck polynorbornenes) with FIG. 3(a) sets forth a Mizoroki-Heck reaction cross-coupling producing a 4-substituted norbornene monomer.
Figure 3B:
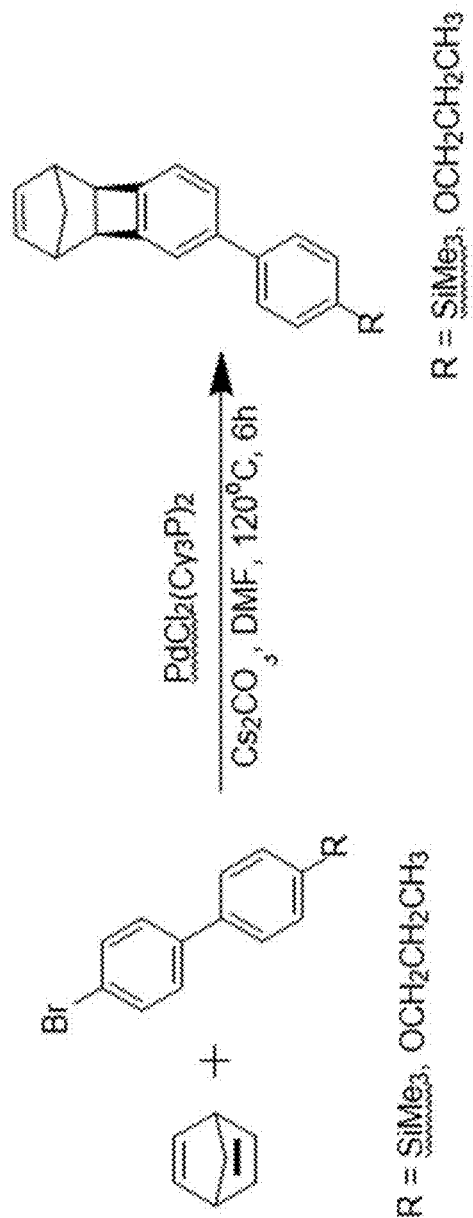
Figure 3C:
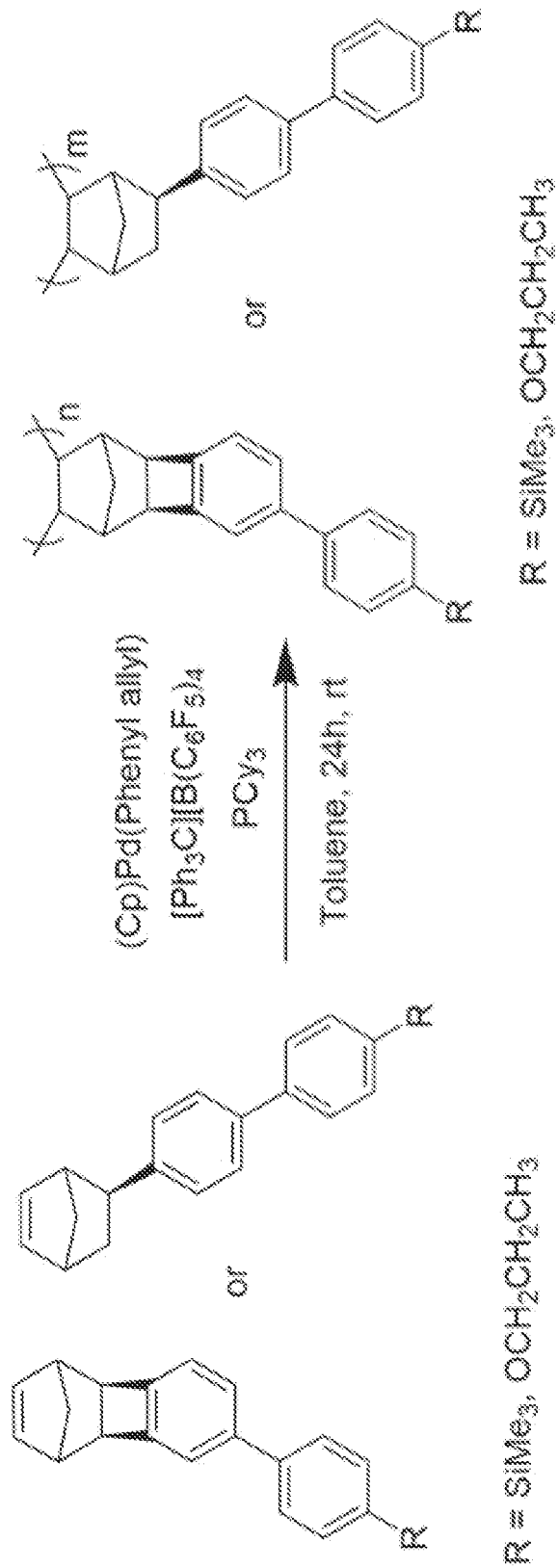

FIGS. 3(a) to 3(d) illustrate exemplary schemes for the synthesis of substituted norbornene monomers through Mizoroki-Heck reactions, which may then be further reacted in vinyl addition-type or ROMP-type polymerizations to obtain polynorbornenes (which can be referred to as being Heck polynorbornenes or a Mizoroki-Heck derived polynorbornenes) as described herein. Generally, FIG. 3(a) sets forth a Mizoroki-Heck reaction cross-coupling producing a 4-substituted norbornene monomer; FIG. 3(b) sets forth Mizoroki-Heck cross-coupling towards producing a cyclic substituted norbornene monomer; FIG. 3(c) sets forth an addition polymerization of either 4-substituted or cyclic monomers in the presence of a palladium catalyst to produce high molecular weight polymer; and FIG. 3(d) sets forth a ring-opening metathesis polymerization (ROMP) of either 4-substituted or cyclic monomer in the presence of Grubbs' 1st generation catalyst to produce a high molecular weight polymer.

In other words, the Mizoroki-Heck type reaction can be used to form two different classes of substituted norbornene monomers, namely, a 4-substituted norbornene monomers that have the exo configuration (FIG. 3(a)) and cyclic substituted norbornene monomers that have the exo configuration (FIG. 3b)). The substituted monomers produced according to the synthesis routes illustrated in FIGS. 3(a) and 3(b) can be polymerized using addition type polymerization (e.g., vinyl addition) as illustrated in FIG. 3(c) or alternatively, the monomers produced according to the synthesis routes illustrated in FIGS. 3(a) and 3(b) can be polymerized using ROMP type polymerization as illustrated in FIG. 3(d).

4-Substituted Norbornene Monomers

Figure 3D:
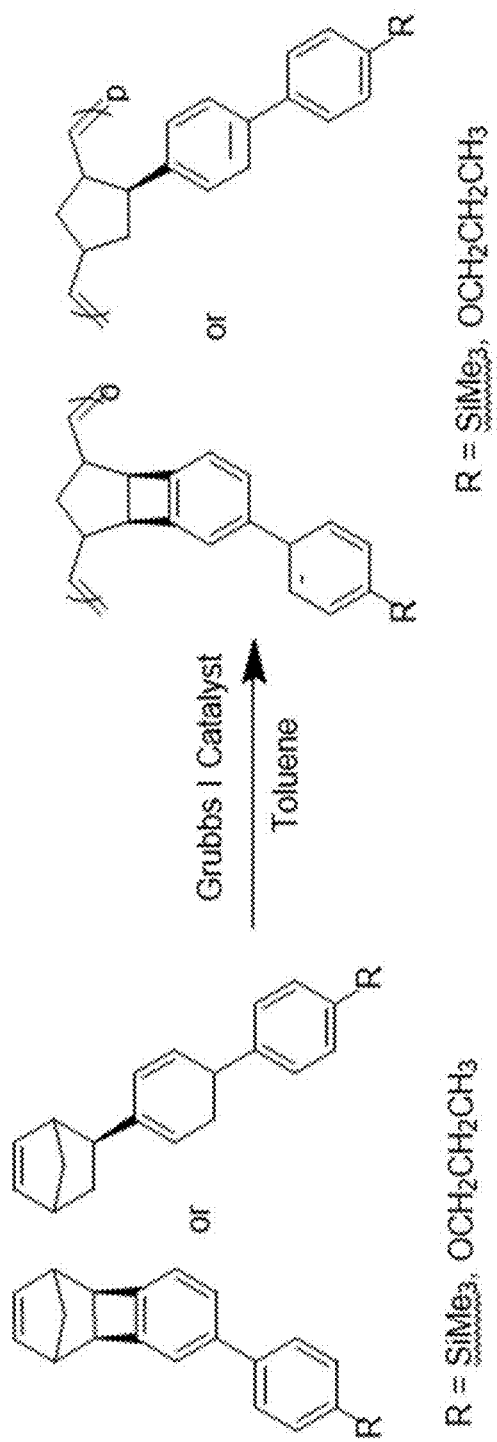
Figure 4:
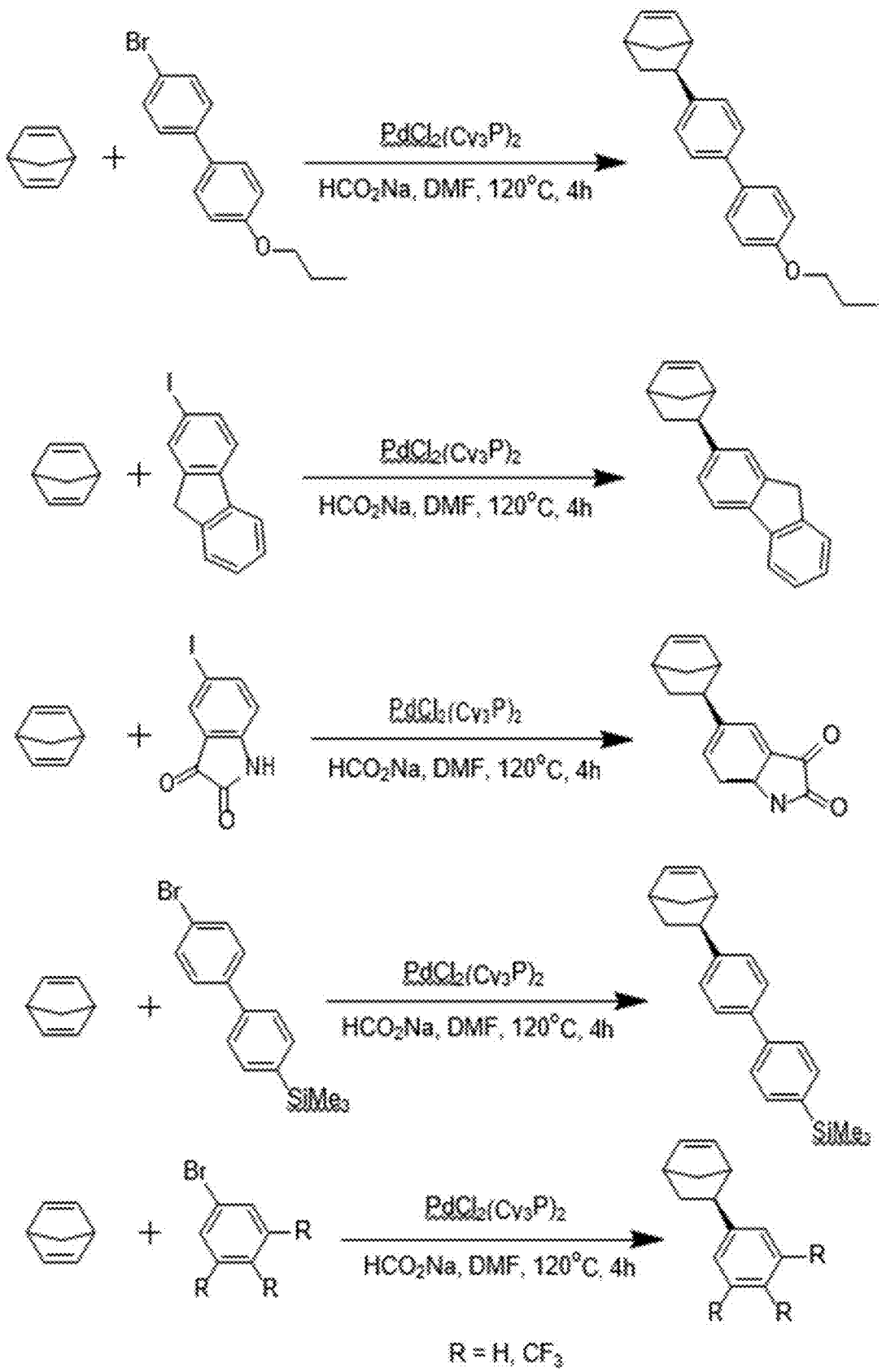
FIG. 4 sets forth a number of exemplary 4-substituted norbornene monomers produced via the Mizoroki-Heck reaction disclosed herein.

More specifically, FIG. 3(a) shows the Mizoroki-Heck reaction between an aryl bromide and norbornadiene towards producing a 4-substituted norbornene monomer suitable for polymerizations (e.g., polymerization of FIG. 3(c) or 3(d)). As mentioned herein, the step shown in FIG. 3(a) illustrates two important features of the present disclosure. More specifically, the resulting substituted norbornene monomer is purely of the exo configuration because of the excellent trans selectivity of the Mizoroki-Heck reaction, indicated by the solid black wedge bond between the norbornene moiety and the aryl substituent derived from the aryl bromide moiety. The aryl bromide used in FIG. 3(a) is only one example and could be replaced by thousands of commercially available aryl chlorides, aryl bromides or aryl iodides. Further examples of this reagent diversity and resulting monomers are shown in FIG. 4. Finally, the reaction conditions such as the palladium catalyst, sodium formate, and polar aprotic solvent at an elevated temperature are merely exemplary, as reaction conditions and reagent choice in the Mizoroki-Heck reaction change based on the reagents involved.

Reagents that are commonly used in a Mizoroki-Heck reaction include bases that include but are not limited to: Na2CO3, NaOAc, K2CO3, triethanolamine, diisopropylamine, DIPEA, other amines, etc. Suitable solvents/mediums include but are not limited to: (organic) DMF, NMP, DMAc, DMSO, dioxane, PhCF3, MeOH, other alcohols and diols, toluene, ionic liquids; (aqueous) H2O, MeCN/H2O mixtures, H2O/DMF, etc. One of the more common solvents comprise polar aprotic solvents. Suitable catalysts include but are not limited to: (Pd-based catalysts) PdCl(allyl)2, PdCl2(COD), Pd(dba)2, Pd(OAc)2, Pd(PPh3)Cl2, PdCl2(dppf), supported Pd catalyst systems, etc. Suitable Heck reaction conditions include temperatures that range from room temperature to 145° C., and reaction times range from 30 minutes to 48 hours, depending on reagents and solvents used. One of skill in the art will understand that all of these variables affect reaction outcomes.

Cyclic Substituted Norbornene Monomers

Figure 5:
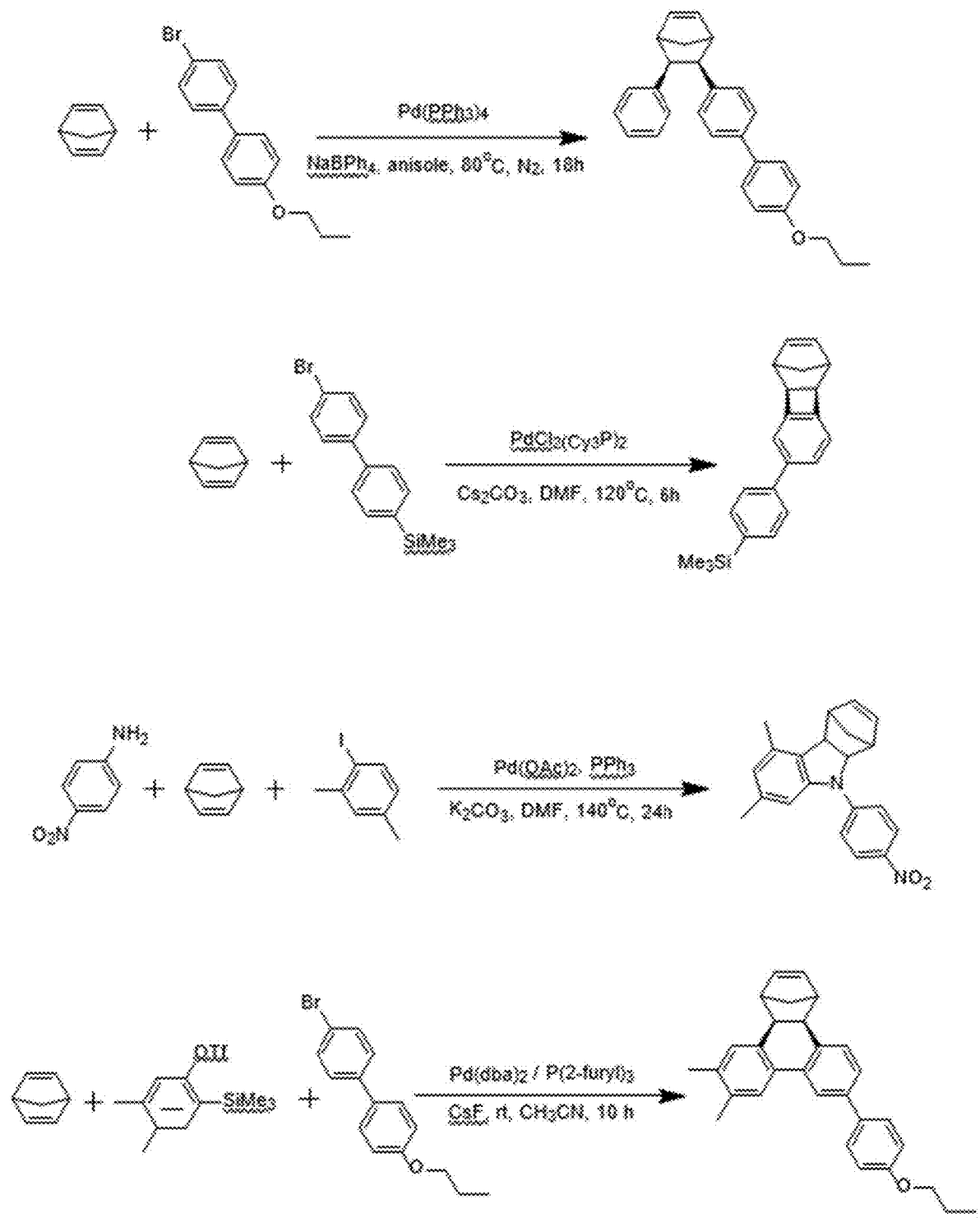
FIG. 5 sets forth a number of exemplary cyclic norbornene monomers produced via the Mizoroki-Heck reaction disclosed herein.

FIG. 3(b) shows the Mizoroki-Heck reaction towards the production of a four membered ring attached to the norbornene structure, and FIG. 5 shows the extension of this concept towards formation of five and six membered rings. The incorporation of additional ring structures beyond the bicyclic norbornene moiety imparts steric strain into the norbornene monomer and the resulting norbornene polymer, which in turn enhances transport properties in the separation of natural gas liquids from natural gas feeds. Similar to FIG. 3(a), this step illustrates two important features of the present disclosure. The resulting substituted norbornene monomer is purely of the exo configuration because of the excellent trans selectivity of the Mizoroki-Heck reaction, indicated by the solid black wedge bonds in the 4 and 5 position between the norbornene moiety and the aryl substituent derived from the aryl bromide moiety. The aryl bromide used in FIG. 3(a) is only one example, and could be replaced by thousands of commercially available aryl chlorides, aryl bromides or aryl iodides. Further examples of this reagent diversity and resulting monomers are shown in FIG. 5, in some cases incorporating an additional aryl reagent to form the five and six membered rings. Finally, the reaction conditions such as the palladium catalyst, $Cs_2CO_3$, and polar aprotic solvent at an elevated temperature are merely exemplary, as reaction conditions and reagent choice in the Mizoroki-Heck reaction change based on the reagents involved. As discussed herein, in order to enable cyclic norbornene formation, an appropriate base is selected as part of the Mizoroki-Heck reaction, including but not limited to $Cs_2CO_3$, $K_2CO_3$, or CsF.

Polymerization to form Norbornene Polymers (Mizoroki-Heck Derived Polynorbornenes)

Addition Type Polymerization

FIG. 3(c) illustrates the addition polymerization of the substituted monomers produced from FIG. 3(a) or FIG. 3(b). The addition polymerization depicted uses a cationic palladium catalyst system in the presence of phosphine ligands, though addition polymerizations may also be performed using titanium-, zirconium-, chromium-, cobalt-, and nickel-based systems. This polymerization yields high molecular weight polymers, where high molecular weight is defined as above the entanglement molecular weight where the polymer is capable of forming free-standing, ductile films. It will be appreciated that formed polymer products are solutions of high viscosity and polymeric solids produced as fibers and/or pellets as opposed to low molecular weight polymers. Furthermore, because of the purely exo configuration of the norbornene monomer, these polymers can achieve 100% yields as opposed to the norbornene polymers obtained from mixtures of endo and exo monomers, where yields may be as low at 30-40%.

ROMP Type Polymerization

FIG. 3(c) illustrates the ring-opening metathesis polymerization (ROMP) of the substituted monomers shown in FIG. 3(a) and FIG. 3(b). The ROMP depicted uses a ruthenium-based catalyst system (Grubbs 1st generation metathesis catalyst), though ROMP may also occur in the presence of titanium, tantalum, molybdenum, tungsten, rhenium, osmium, iridium, and cobalt catalysts. This polymerization proceeds to high molecular weight, where high molecular weight is defined as the entanglement molecular weight where the polymer is capable of forming free-standing, ductile films. Once again, it will be appreciated that formed polymer products are solutions of high viscosity and polymeric solids produced as fibers and/or pellets as opposed to low molecular weight polymers. ROMP of substituted norbornene monomers is often indiscriminate of endo versus exo configuration, and is capable of achieving nearly 100% yields regardless of the stereoisomers present in the monomeric mixture.

EXAMPLES

The following examples are provided to better illustrate embodiments of the present disclosure. However, it is to be understood that these examples are merely illustrative in nature, and that the process embodiments of the present disclosure are not necessarily limited thereto.

Figure 7:
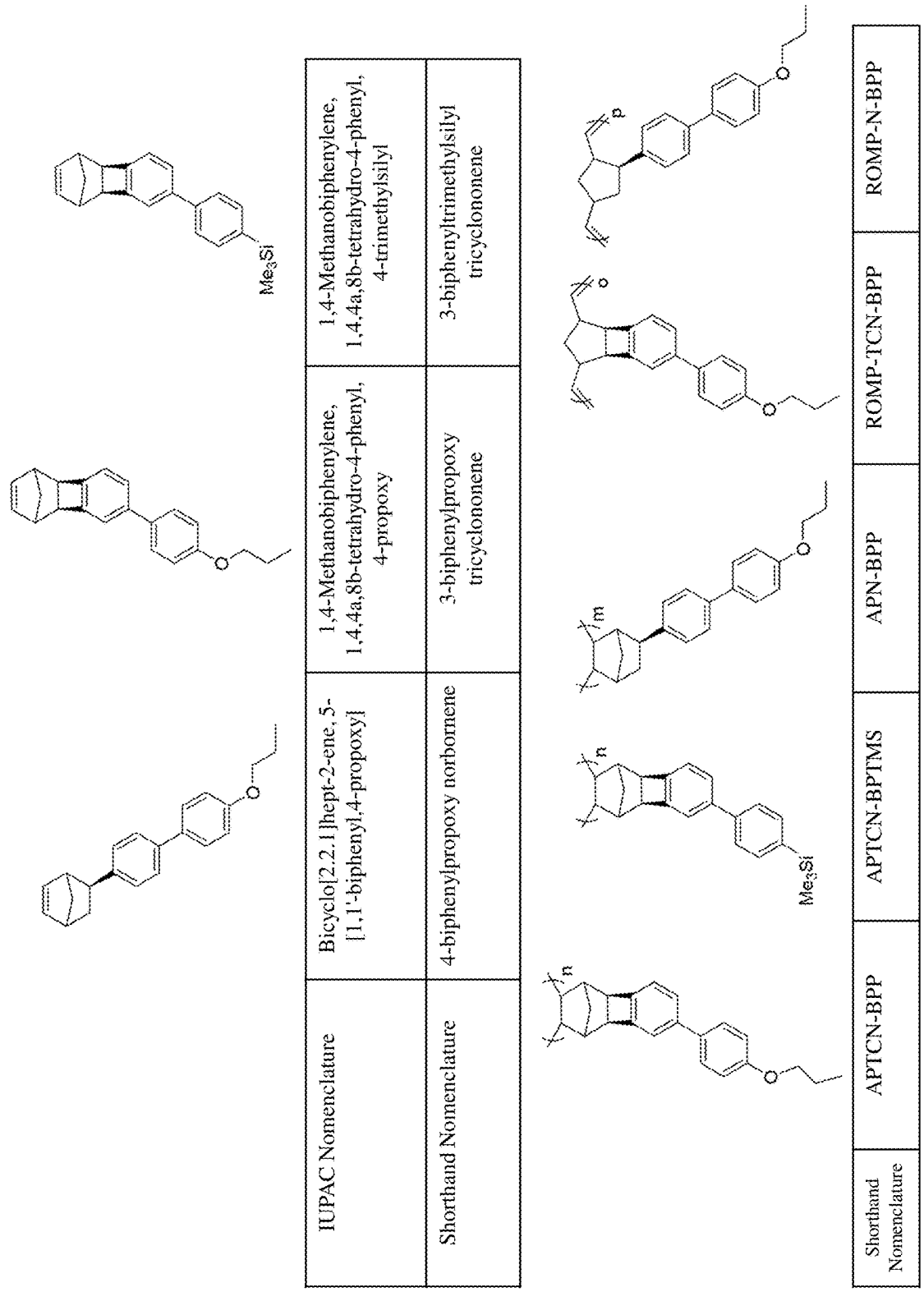
FIG. 7 sets forth IUPAC and shorthand nomenclature for monomers shown in FIGS. 3(a)-3(d) and shorthand nomenclature for the polymers (polynorbornenes) shown in FIGS. 3(a)-3(d)

Experimental procedures for the synthesis of 4-biphenyl-propoxy norbornene, 3-biphendlypropoxy tricyclononenes, 3-biphenyltrimethylsilyl tricyclononene, APTCN-BPP, APN-BPP, APTCN-BPTMS, ROMP-TCN-BPP and ROMP-N-BPP are disclosed below. The shorthand nomenclature for the structured depicted in FIGS. 3(a)-(d) are shown in FIG. 7 and this shorthand nomenclature will be used for the remainder of the present disclosure.

Example 1

Example 1 is described by the following Reaction 1:

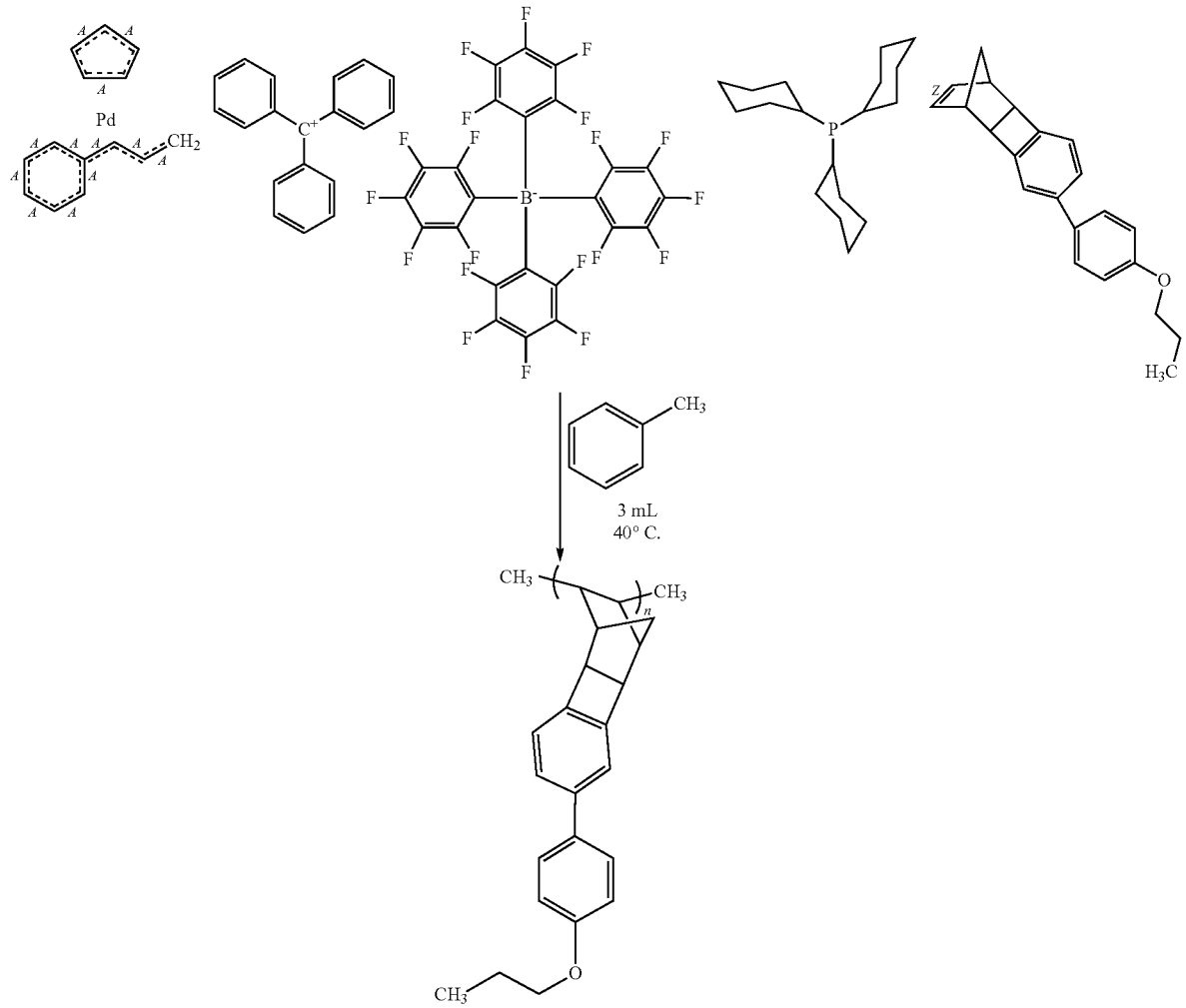

The following table is a stoichiometry table for the reagents (reactants) of Reaction 1.

| | Reactant 1 | Reactant 2 | Reactant 3 | Reactant 4 | Agent 1 |
|---|---|---|---|---|---|
| Molecular Weight | 288.690 | 922.358 | 280.428 | 302.409 | 92.138 |
| Equivs | 1.000 | 1.000 | 1.000 | 5000.000 | |
| Amount | 0.095 | 0.305 | 0.093 | 0.500 | 20.000 |
| Amount Units | mg | mg | mg | g | mL |
| n | 0.331 | 0.331 | 0.331 | 1.653 | |
| n Units | μmol | μmol | μmol | mmol | mol |
| Limit | ☐ | ☐ | ☐ | ■ | ☐ |

The reactants 1-4 and agent 1 for Reaction 1 are set forth below.

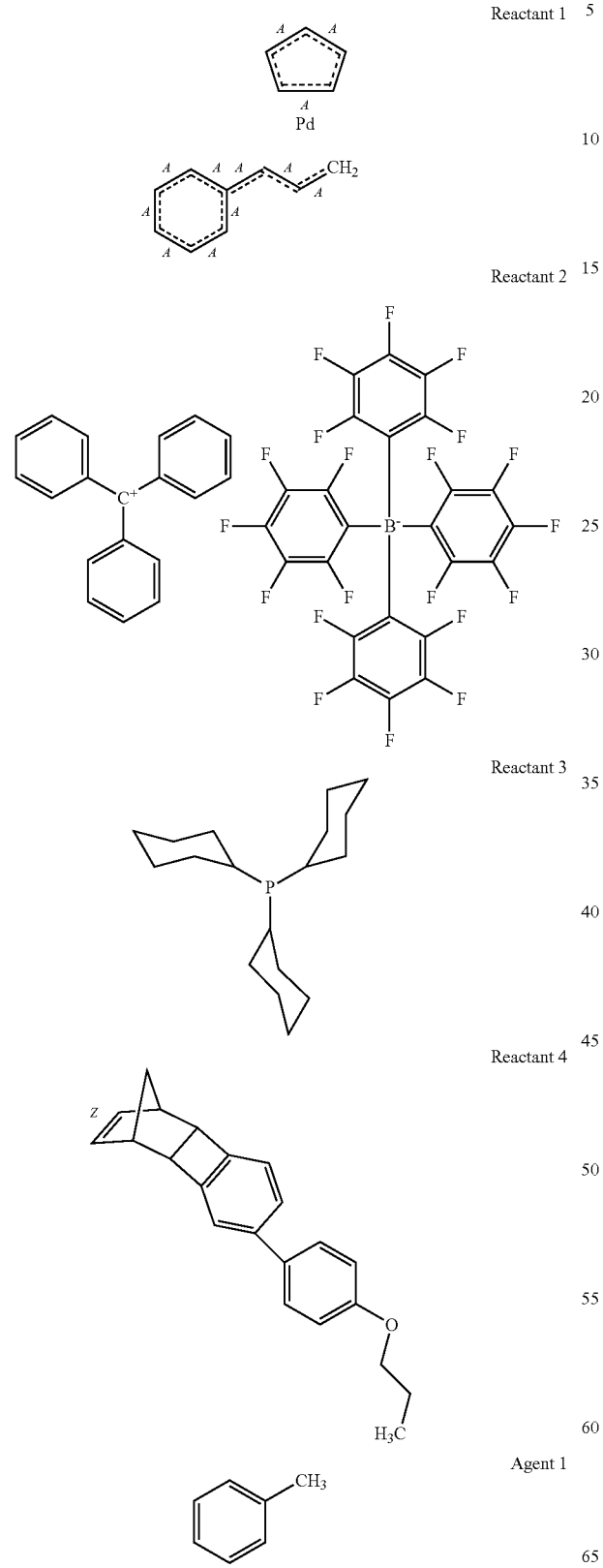

The following table is a stoichiometry table for the product of Reaction 1.

| Structure | Product 1 |
|---|---|
| Molecular Weight | 302.409 |
| N | 0.001 |
| n Units | mol |
| Actual Mass | 0.399 |
| Mass Units | g |
| Expected Mass | 0.500 |
| Purity | 100.000% |
| Expected % Yield | 100.000% |
| % Yield | 79.880% |

As described herein, Example 1 is directed to an addition type polymerization of cyclobutene heck monomer at a reaction temperature of 100° C. in the presence of toluene (agent).

The procedure is as follows, with all work being conducted in a glovebox under nitrogen. All chemicals used excluding the heck monomer were commercially available and required no further purification.

Step 1: Solutions of the catalyst, activator, and phosphine were prepared: 1-0.95 mg catalyst in 1.0 mL dry toluene 2-3.05 mg PCy3 in 1.0 mL dry toluene 3-0.93 mg trityl BArF 1.0 mL dry toluene 0.3 mL aliquots of each of the solutions were then combined in a 3 mL scintillation vial in the following order (1+2+3) to form the catalyst-phosphine-BArF solution. Step 2: 0.50 g of monomer (combination of PNB-TL-149, PNB-TL-151, PNB-TL-153) was weighed out in a 40 mL scintillation vial equipped with stir bar in the glove box. The monomer was then dissolved in 30 mL dry toluene (dried using in-house SPS and stored in the glove box over 4 A molecular sieves).

Step 3: 0.3 mL of the catalyst-phosphine-BArF solution was then added to the reaction vessel. The reaction was set to stir briefly in the glove box. Then, the reaction was capped and sealed under nitrogen in the glove box, brought out to the fume hood and left to stir at 1500 rpm at 100° C. for 24 hours on a hot plate.

The resulting polymer solution was precipitated in a large amount of acetone (1000 mL), then collected on an aspirator. Polymer appeared as a white solid. The polymer was then dried in vacuo to constant weight. Yield: 0.3994 g (79.8%).

Example 2

Example 2 is described by the following Reaction 2:

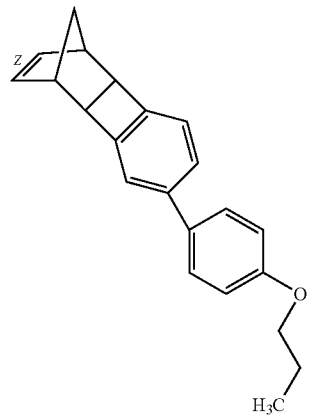

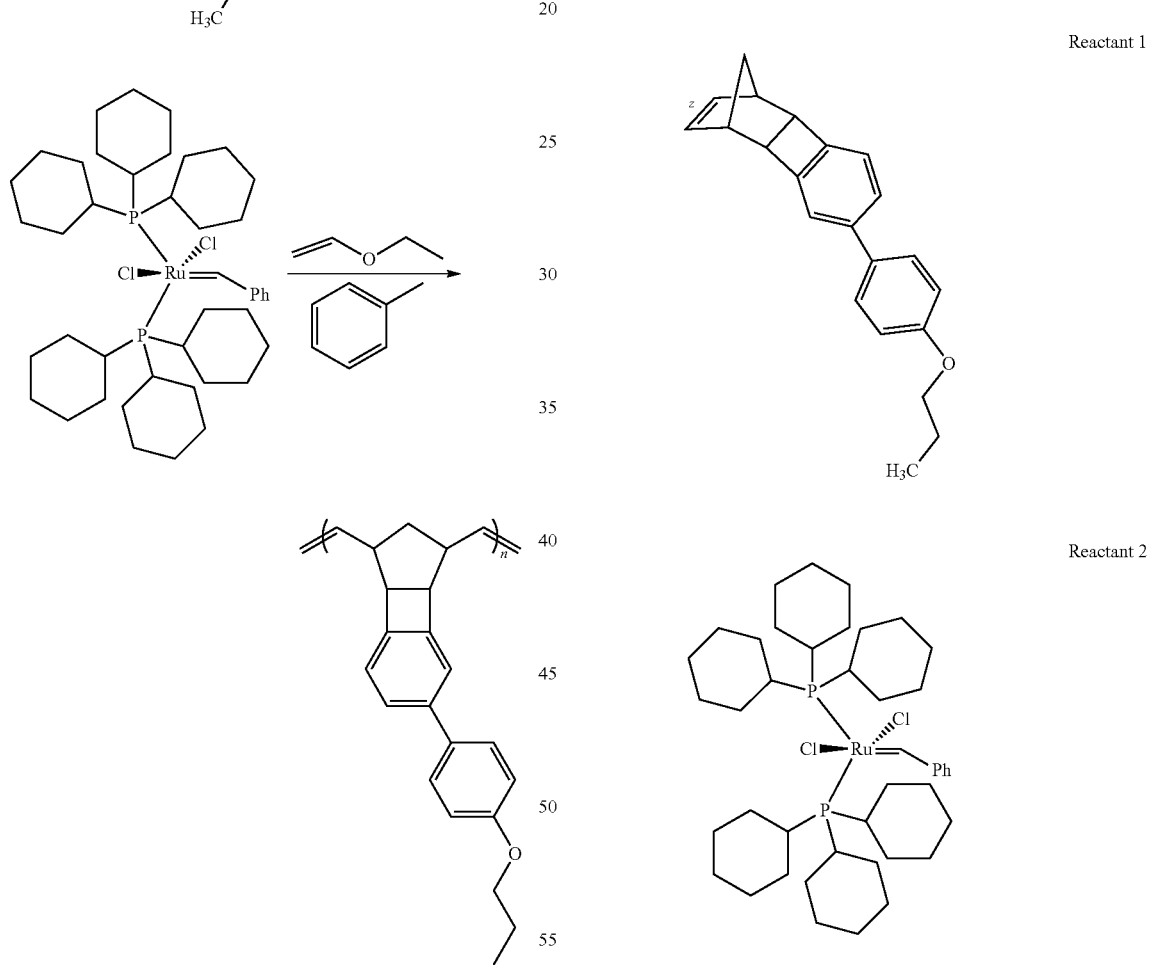

The following table is a stoichiometry table for the reagents (reactants) of Reaction 2.

|  | Reactant 1 | Reactant 2 | Agent 1 | Agent 2 |
|---|---|---|---|---|
| Substance | monomer | catalyst | inhibitor | solvent |
| Molecular Weight | 302.409 | 822.970 | 72.106 | 92.138 |
| .Equivs | 1.000 |  0.001 | 3.000 |  |
| Amount | 0.500 | 1.361 | 0.475 | 25.000 |
| Amount Units | g | mg | mL | mL |
| n | 1.653 | 1.653 | 0.005 |  |
| n Units | mmol | μmol | mol | mol |
| Mass Units | g | mg | g | g |
| Volume Units | mL | mL | mL | mL |
| Density |  |  | 0.753 |  |
| Density Units |  |  | g/mL |  |
| Limit | ☐ | ■ | ☐ | ☐ |

The reactants and agents of Reaction 2 are set forth below.

The following table is a stoichiometry table for the product of Reaction 2.

| Product 1 | |
|---|---|
| Structure | |
| Substance | Polymer product |
| Molecular Weight | 302.409 |
| Amount Units | g |
| n | 0.001 |
| n units | mol |
| Actual Mass | 0.358 |
| Mass Units | g |
| Expected Mass | 0.500 |
| Volume Units | mL |

Under ambient conditions, a 30 ml scintillation vial was charged with 0.50 grams of monomer and a stir bar. The vial was then brought into the glove box. In the glove box under nitrogen, the monomer was dissolved in 25 ml anhydrous toluene (SPS) and set to stir. A catalyst solution was then prepared by dissolving 13.6 mg Grubbs 1st gen catalyst in 1 ml toluene in a scint. vial. 0.1 ml of the catalyst solution was then added to the stirring monomer solution. The vial was capped, sealed with electrical tape, and brought out of the glove box to stir at 40° C. overnight. Once the reaction was complete, 0.50 ml ethyl vinyl ether was added and the reaction was allowed to stir for an additional 30 minutes.

The resulting polymer solution was precipitated in a large amount of acetone (1000 mL), then collected on an aspirator. Polymer appeared as an off-white solid. The polymer was then dried in vacuo to constant weight. Yield: 0.3581 g (71.6%).

Example 3

Example 3 is described by the following Reaction 3:

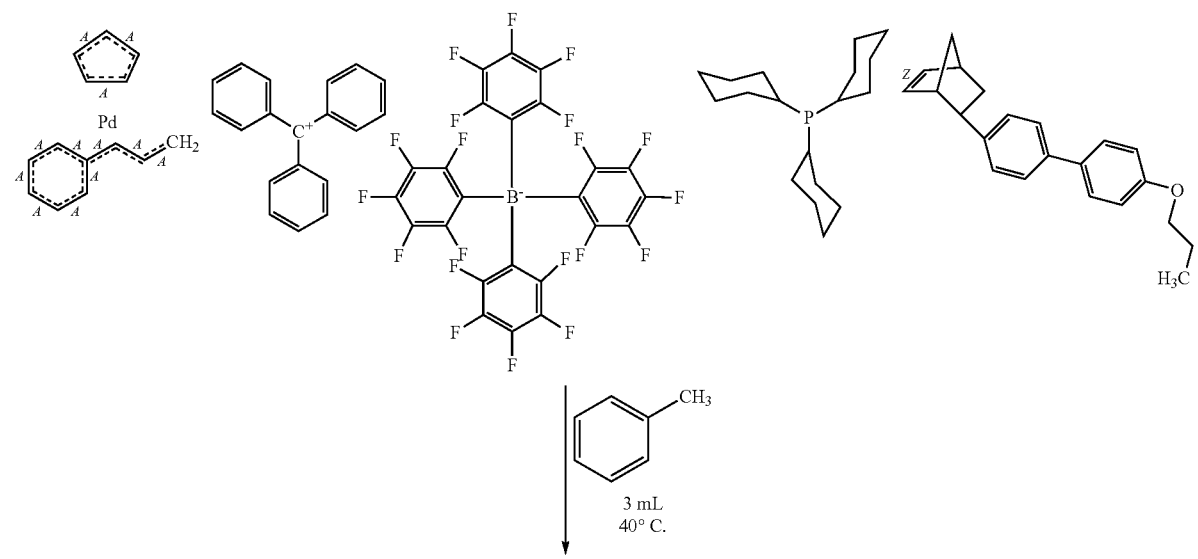

-continued
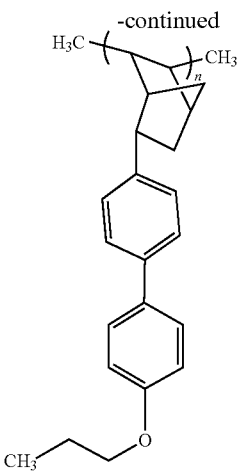
The following table is a stoichiometry table for the reagents (reactants) of Reaction 3.
|  | Reactant 1 | Reactant 2 | Reactant 3 | Reactant 4 | Agent 1 |
|---|---|---|---|---|---|
| Molecular Weight | 288.690 | 922.358 | 280.428 | 304.425 | 92.138 |
| Equivs | 1.000 | 1.000 | 1.000 | 5000.000 |  |
| Amount | 0.095 | 0.303 | 0.092 | 0.500 | 200.000 |
| Amount Units | mg | mg | mg | g | mL |
| n | 0.328 | 0.328 | 0.328 | 1.642 |  |
| n Units | μmol | μmol | μmol | mmol | mol |
| Limit | ■ | □ | □ | □ | □ |
The reactants and agent for Reaction 3 are set forth below:
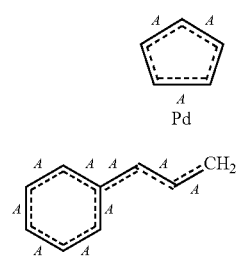
Reactant 1
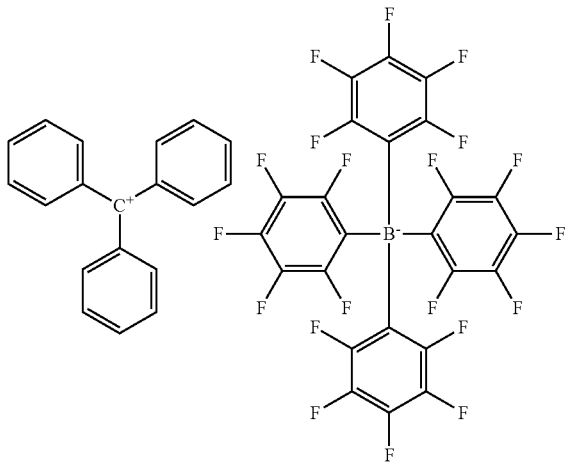
Reactant 2
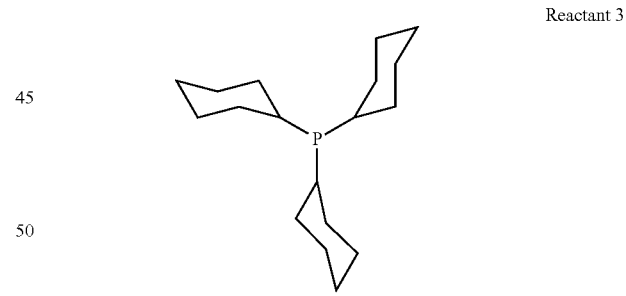
Reactant 3
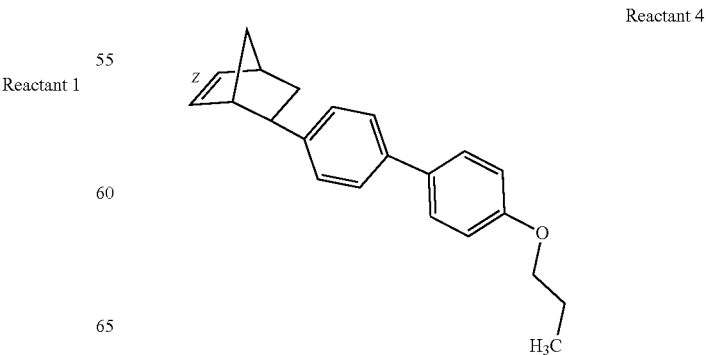
Reactant 4

Agent 1

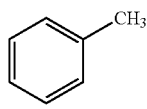

The following table is a stoichiometry table for the product of Reaction 3.

| Structure | Product 1 |
|---|---|
| Molecular Weight | 304.425 |
| N | 1.311 |
| n Units | mmol |
| Actual Mass | 0.399 |
| Mass Units | g |
| Expected Mass | 0.500 |
| Purity | 100.000% |
| Expected % Yield | 100.000% |
| % Yield | 79.8% |

As described herein, Example 3 is directed to addition-type polymerization of 4-substituted heck monomer at a reaction temperature of 100° C. in toluene.

All work conducted in the glovebox under nitrogen. All chemicals used excluding the heck monomer were commercially available and required no further purification. Step 1: Solutions of the catalyst, activator, and phosphine were prepared: I-0.95 mg catalyst in 1.0 mL dry toluene 2-3.05 mg PCy3 in 1.0 mL dry toluene 3-0.93 mg trityl BArF 1.0 mL dry toluene 0.3 mL aliquots of each of the solutions were then combined in a 3 mL scintillation vial in the following order (I+2+3) to form the catalyst-phosphine-BArF solution. Step 2: 0.50 g of monomer (PNB-TP-001) was weighed out in a 40 mL scintillation vial equipped with stir bar in the glove box. The monomer was then dissolved in 30 mL dry toluene (dried using in-house SPS and stored in the glove box over 4 A molecular sieves). Step 3: 0.3 mL of the catalyst-phosphine-BArF solution was then added to the reaction vessel. The reaction was set to stir briefly in the glove box. Then, the reaction was capped and sealed under nitrogen in the glove box, brought out to the fume hood and left to stir at 1500 rpm at 100° C. for 24 hour on a hot plate.

The resulting polymer solution was precipitated in a large amount of acetone (1000 mL), then collected on an aspirator. Polymer appeared as a white solid. The polymer was then dried in vacuo to constant weight. Yield: 0.3999 g (79.8%)

Example 4

Example 4 is described by the following Reaction 4:

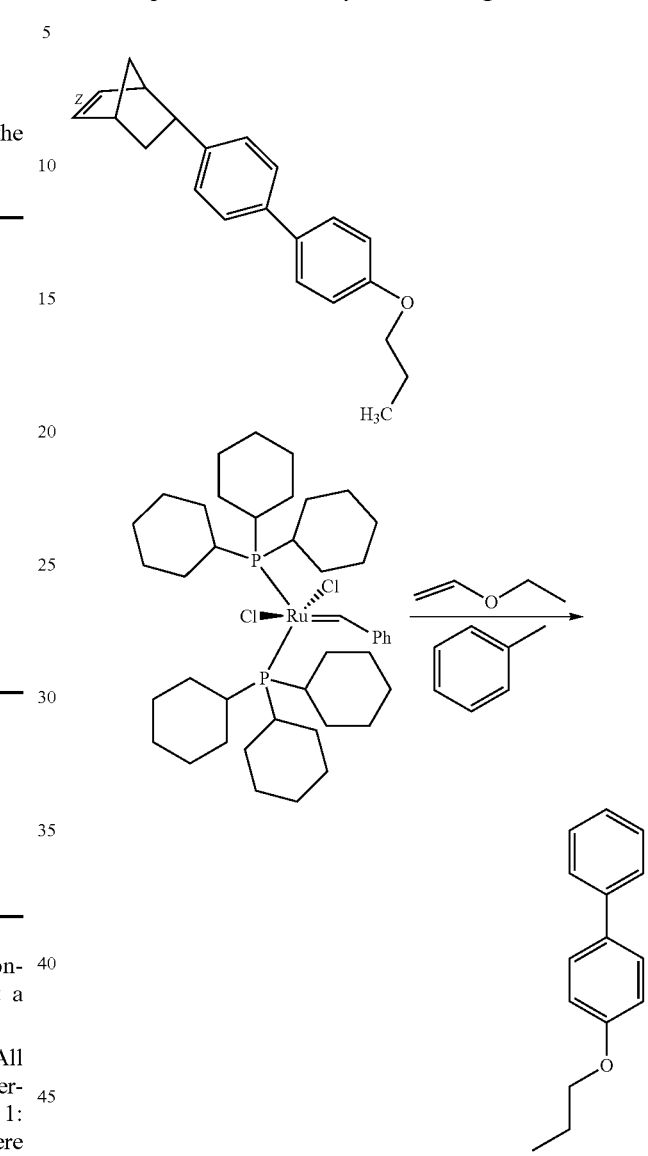

The following table is a stoichiometry table for the reagents (reactants) of Reaction 4.

| | Reactant 1 | Reactant 2 | Agent 1 | Agent 2 |
|---|---|---|---|---|
| Substance | monomer | catalyst | inhibitor | solvent |
| Molecular Weight | 304.425 | 822.970 | 72.106 | 92.138 |
| .Equivs | 1.000 | 0.001 | 3.000 | |
| Amount | 0.500 | 1.352 | 0.472 | 25.000 |
| Amount Units | g | mg | mL | mL |
| n | 1.642 | 1.642 | 0.005 | |
| n Units | mmol | μmol | mol | mol |
| Mass Units | g | mg | g | g |
| Volume Units | mL | mL | mL | mL |
| Density | | | 0.753 | |
| Density Units | | | g/mL | |
| Limit | ☐ | ■ | ☐ | ☐ |

The reactants and agents for Reaction 4 are set forth below:

| | |
|---|---|
| Reactant 1 | 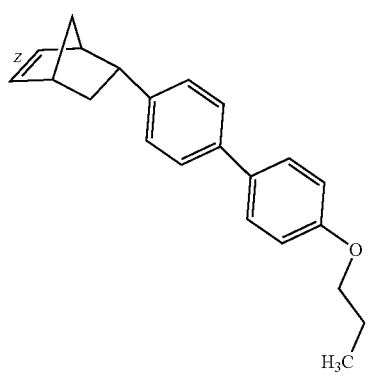 |
| Reactant 2 | 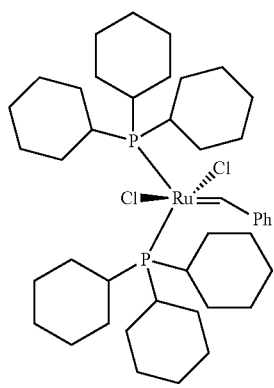 |
| Agent 1 | 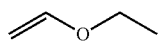 |
| Agent 2 | 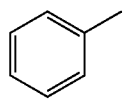 |

The following table is a stoichiometry table for the product of Reaction 4.

| | Product 1 |
|---|---|
| Structure | 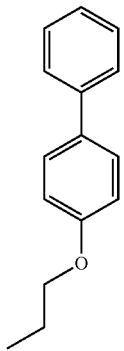 |

| Substance | Polymer product |
|---|---|
| Molecular Weight | 304425.000 |
| Amount Units | mg |
| N | 0.001 |
| n Units | mmol |
| Actual Mass | 358.200 |
| Mass Units | mg |
| Expected Mass | 499.999 |
| Volume Units | mL |
| Purity | 100.000% |
| % Yield | 71.7 |

Reaction 4 is directed to a ROMP of 4-substituted heck monomer.

The materials used in reaction 4 are as follows: Monomer—PNB-TP-001; Grubbs catalyst—97% purity, Sigma-Aldrich, lot no. MKBQ7821V; and ethyl vinyl ether—>98% purity, Fluka Analytical, lot no. BCBL3917V.

Under ambient conditions, a 30 ml scintillation vial was charged with 0.50 grams of PNB-TP-001 and a stir bar. The vial was then brought into the glove box. In the glove box under nitrogen, the monomer was dissolved in 25 ml anhydrous toluene (SPS) and set to stir. A catalyst solution was then prepared by dissolving 13.5 mg Grubbs 1st gen catalyst in 1 ml toluene in a scint. vial. 0.1 ml of the catalyst solution was then added to the stirring monomer solution. The vial was capped, sealed with electrical tape, and brought out of the glove box to stir at 40° C. overnight. Once the reaction was complete, 0.50 ml ethyl vinyl ether was added and the reaction was allowed to stir for an additional 30 minutes.

The resulting polymer solution was precipitated in a large amount of acetone (1000 mL), then collected on an aspirator. Polymer appeared as a off-white solid. The polymer was then dried in vacuo to constant weight. Yield: 0.3583 g (71.7%)

Example 5
Example 5 is described by the following Reaction 5:
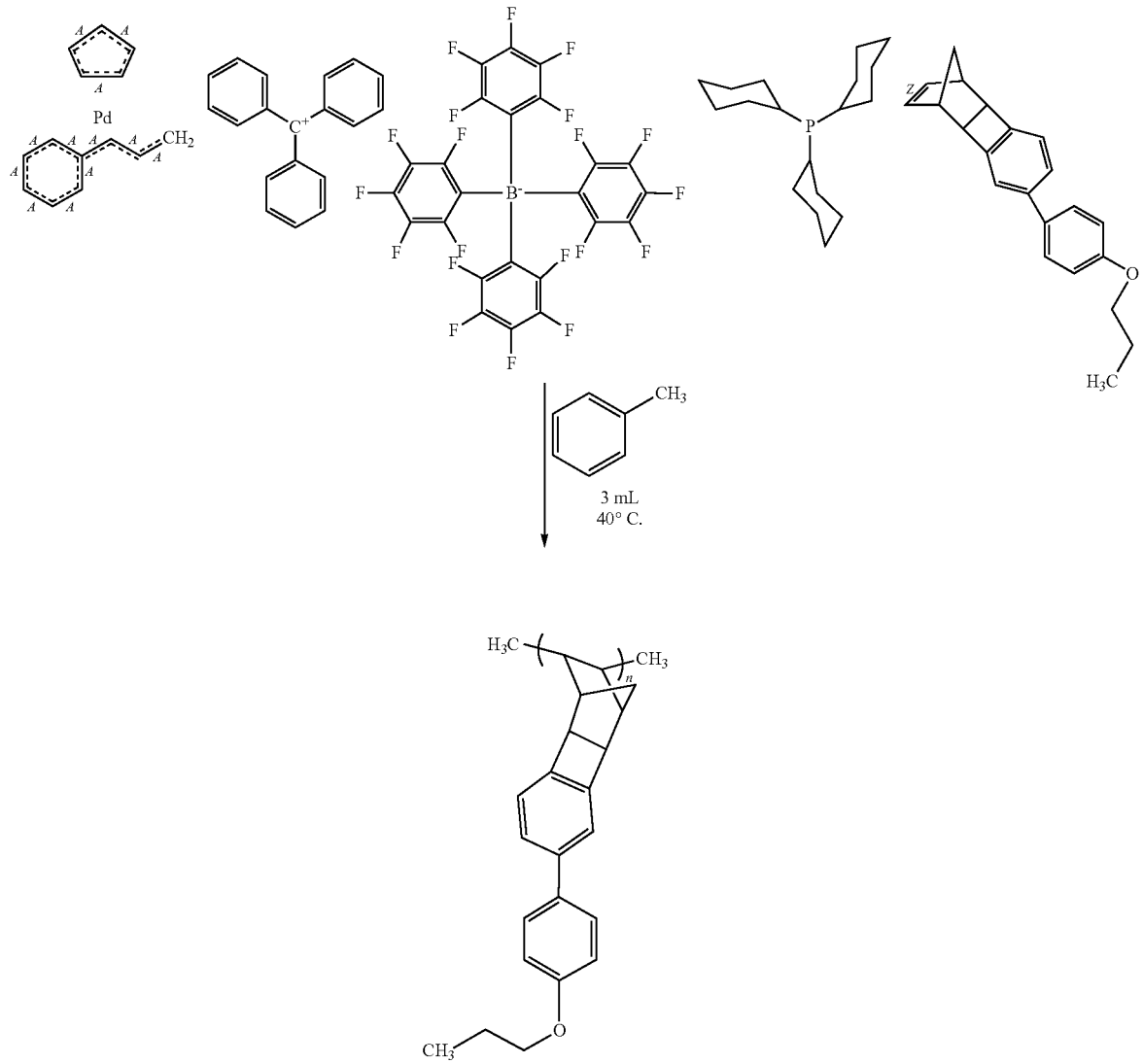
The following table is a stoichiometry table for the reagents (reactants) of Reaction 5.
|  | Reactant 1 | Reactant 2 | Reactant 3 | Reactant 4 | Agent 1 |
|---|---|---|---|---|---|
| Molecular Weight | 288.690 | 922.358 | 280.428 | 302.409 | 92.138 |
| Equivs | 1.000 | 1.000 | 1.000 | 5000.000 |  |
| Amount | 0.338 | 1.081 | 0.329 | 1.772 | 30.000 |
| Amount Units | mg | mg | mg | g | mL |
| n | 1.172 | 1.172 | 1.172 | 5.860 |  |
| n Units | μmol | μmol | μmol | mmol | mol |
| Limit | ☐ | ☐ | ☐ | ■ | ☐ |
The reactants and agent for Reaction 5 are set forth below.
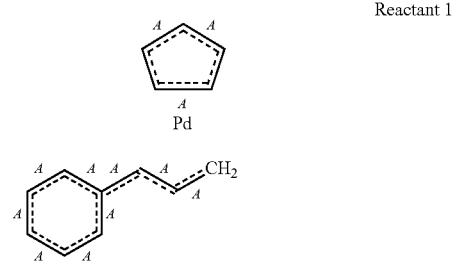
Reactant 1

-continued

Reactant 2

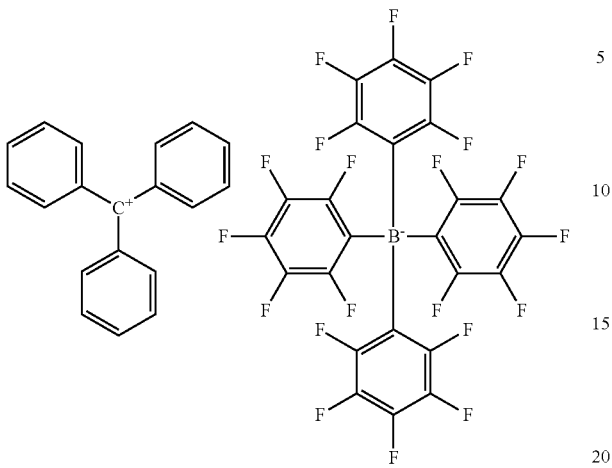

Reactant 3

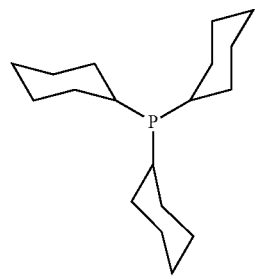

Reactant 4

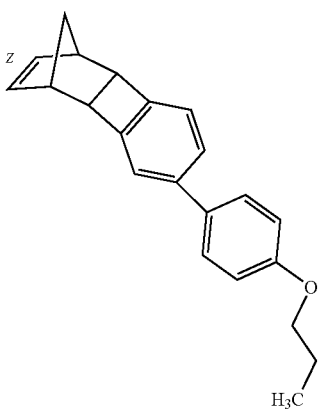

Agent

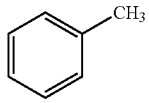

The following table is a stoichiometry table for the product of Reaction 5.

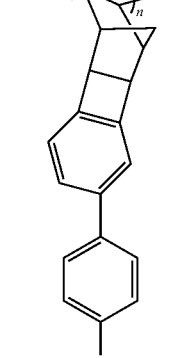

| | Product 1 |
|---|---|
| Structure | (shown above) |
| Molecular Weight | 302.409 |
| N | 0.006 |
| n units | mol |
| Actual Mass | 1.768 |
| Mass Units | g |
| Expected Mass | 1.772 |
| Purity | 100.000% |
| Expected % Yield | 100.000% |
| % Yiels | 99.768% |

Example 5 is directed to an addition-type polymerization of cyclobutene heck monomer at an operation condition of 100° C. in toluene.

All work conducted in the glovebox under nitrogen. All chemicals used excluding the heck monomer were commercially available and required no further purification. Step 1: Solutions of the catalyst, activator, and phosphine were prepared: 1-3.4 mg catalyst in 1.0 mL dry toluene 2-3.3 mg PCy3 in 1.0 mL dry toluene 3-10.8 mg trityl BArF 1.0 mL dry toluene 0.3 mL aliquots of each of the solutions were then combined in a 3 mL scintillation vial in the following order (1+2+3) to form the catalyst-phosphine-BArF solution. Step 2: 1.772 g of monomer (PNB-WP-031-019_COL1) was weighed out in a 40 mL scintillation vial equipped with stir bar in the glove box. The monomer was then dissolved in 30 mL dry toluene (dried using in-house SPS and stored in the glove box over 4 A molecular sieves). Step 3: 0.3 mL of the catalyst-phosphine-BArF solution was then added to the reaction vessel. The reaction was set to stir briefly in the glove box. Then, the reaction was capped and sealed under nitrogen in the glove box, brought out to the fume hood and left to stir at 1500 rpm at 100° C. for 24 hours on a hot plate. Observations: Reaction color: slight yellow, transparent; no color change upon polymerization After approximately 0.5 hours @ 100° C., the reaction became very viscous. The resulting polymer solution was precipitated in a large amount of acetone (2000 mL), then collected on an aspirator. Polymer appeared as a white, fibrous solid. The polymer was then dried in vacuo to constant weight. Yield: 1.768 g (99.8%).

Of particular note is the 99.8% yield of APTCN-BPP in reaction PNB-TL-158 (Reaction 5), which confirms the hypothesis that the monomers synthesized through the Mizoroki-Heck reaction are capable of giving much higher yields (100% compared to 30-40% in several cases) in the polymerization processes than previous Diel-Alder reactions. Reaction PNB-TL-154 (Reaction 1) provided APTCN-BPP with a 70-80% yield, similar to other ROMP, APN, and APTCN polymers shown in reactions PNB-TL-155 (Reaction 2), PNB-TL-156 (Reaction 3), and PNB-TL-157 (Reaction 4). This lower yield arises from the lower purity of the starting material and not because of the inefficiency of the polymerizations.

Figure 8:
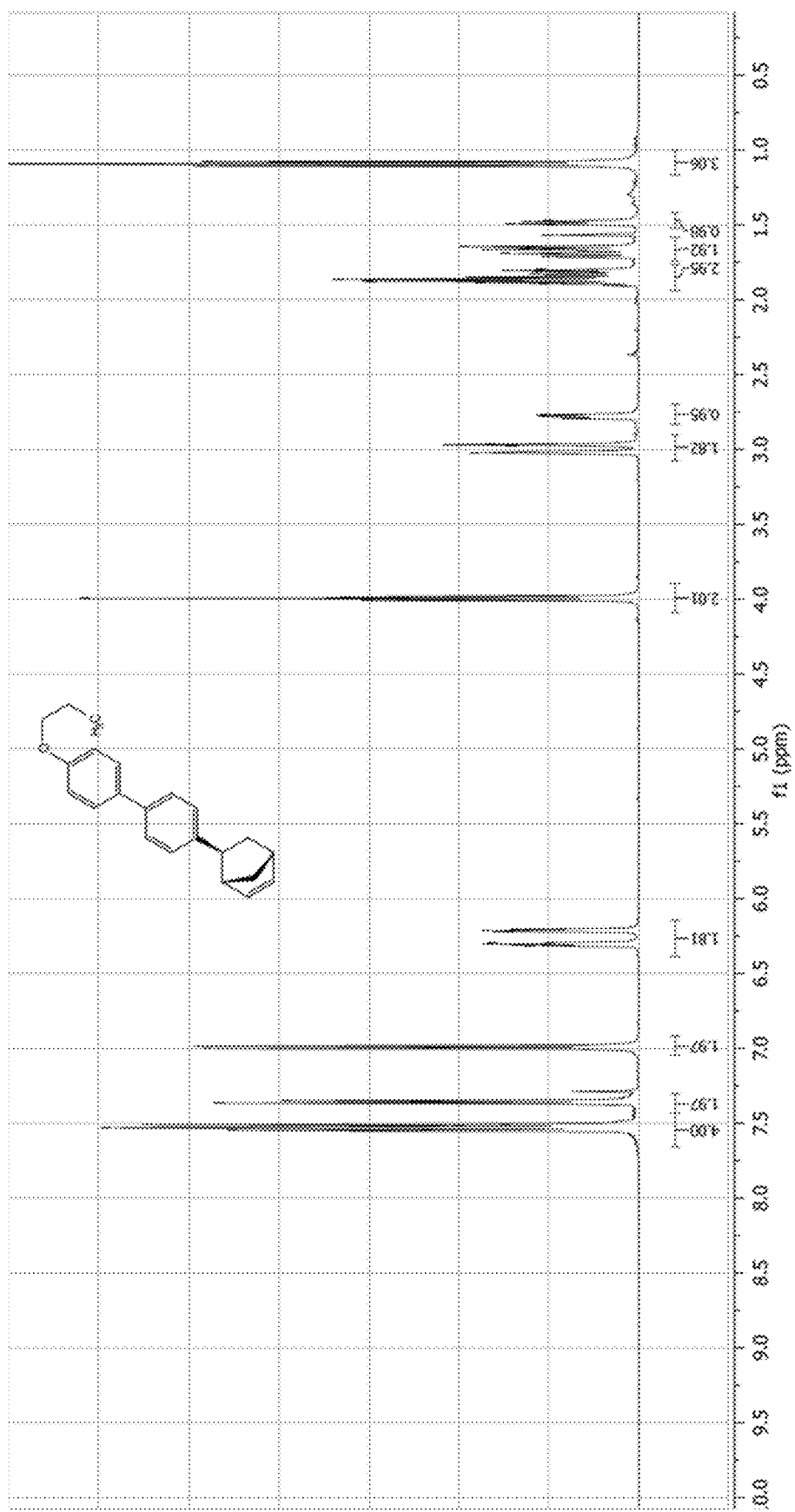
FIG. 8 is a $^1$H-NMR spectra of 4-biphenylpropoxy norbornene.
Figure 9:
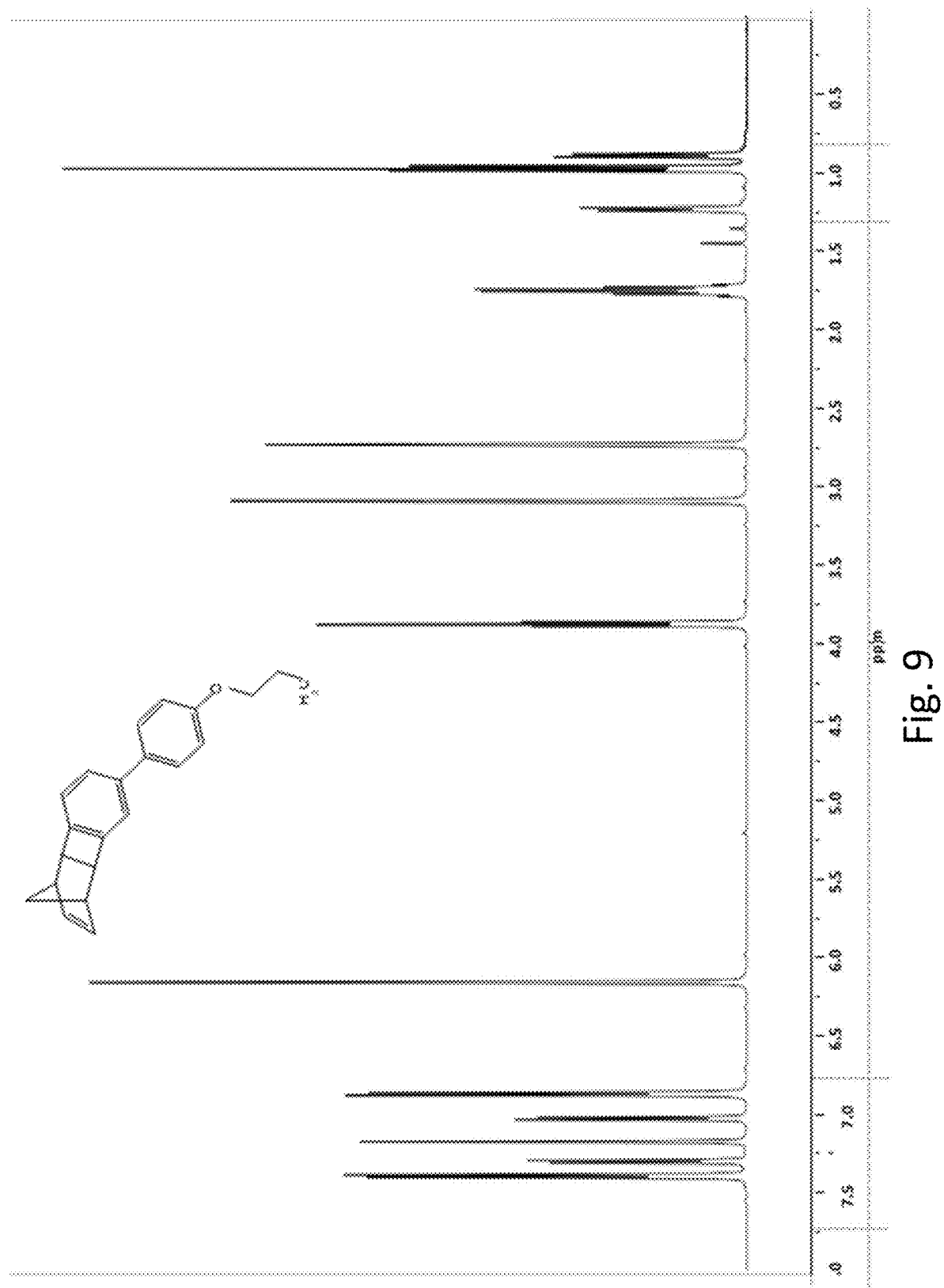
FIG. 9 is a $^1$H-NMR spectra of 4-biphenylpropoxy tricyclononene.
Figure 10:
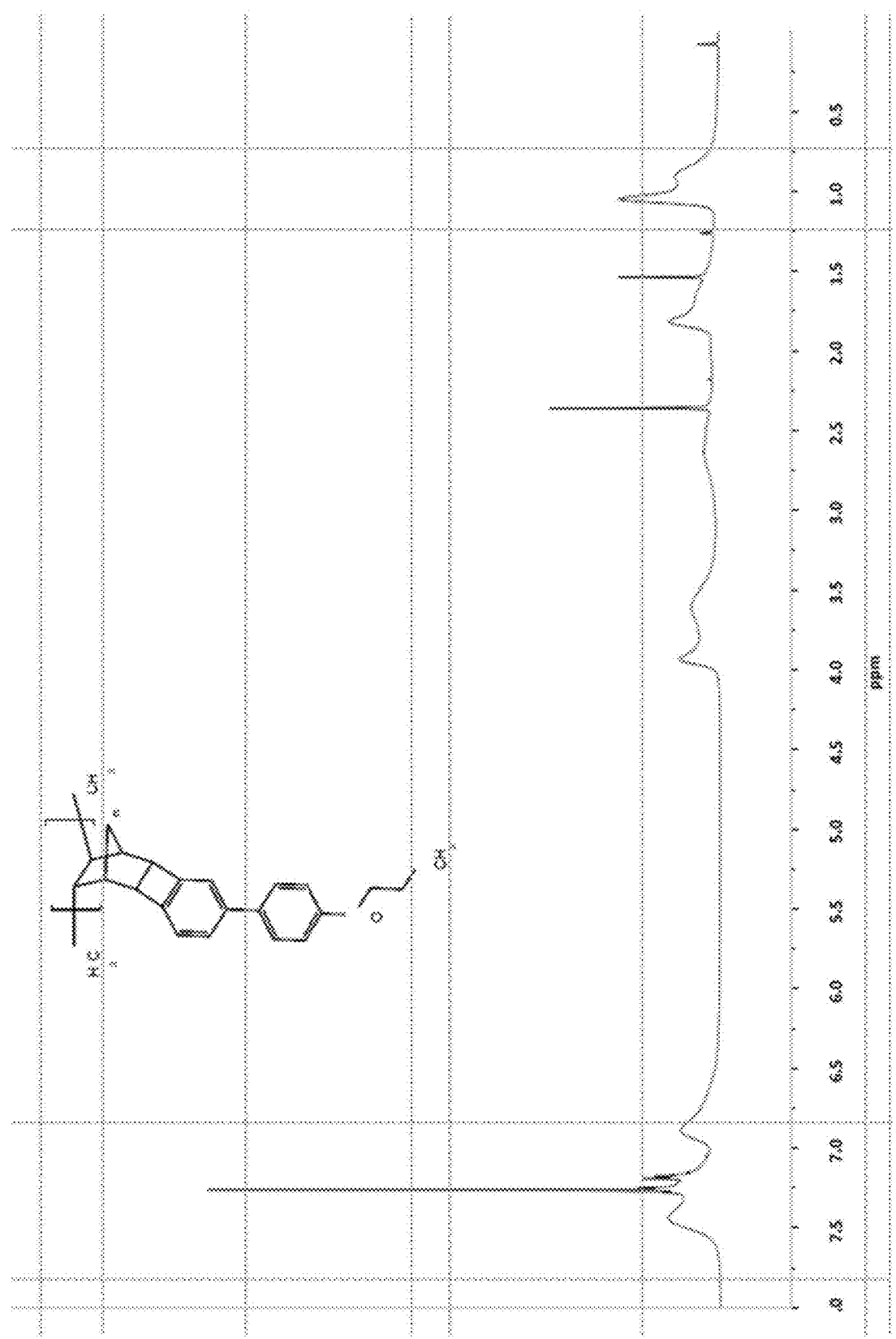
FIG. 10 is a $^1$H-NMR spectra of APTCN-BPP.
Figure 11:
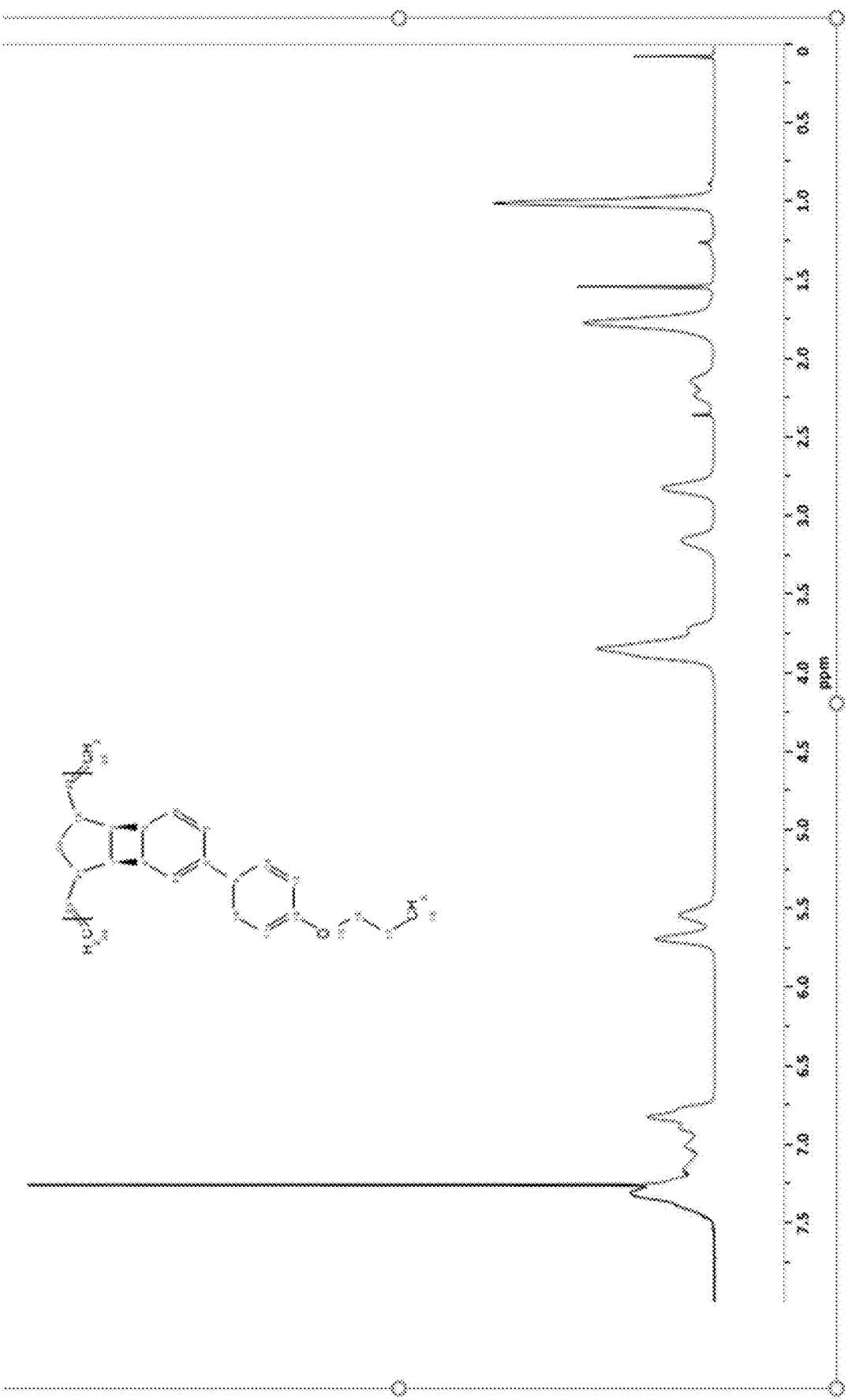
FIG. 11 is a $^1$H-NMR spectra of ROMP-TCN-BPP.
Figure 12:
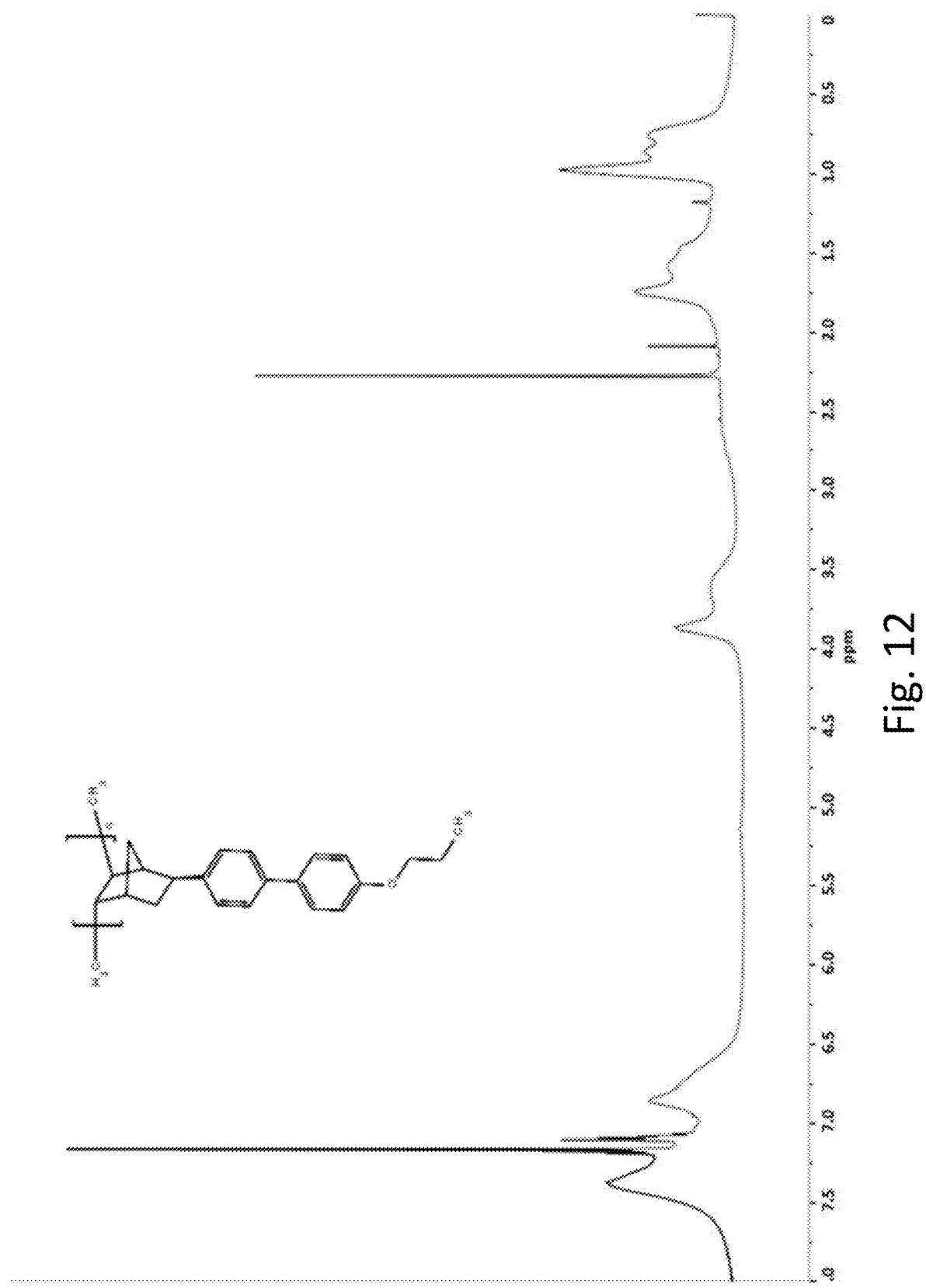
FIG. 12 is a $^1$H-NMR spectra of APN-BPP.
Figure 13:
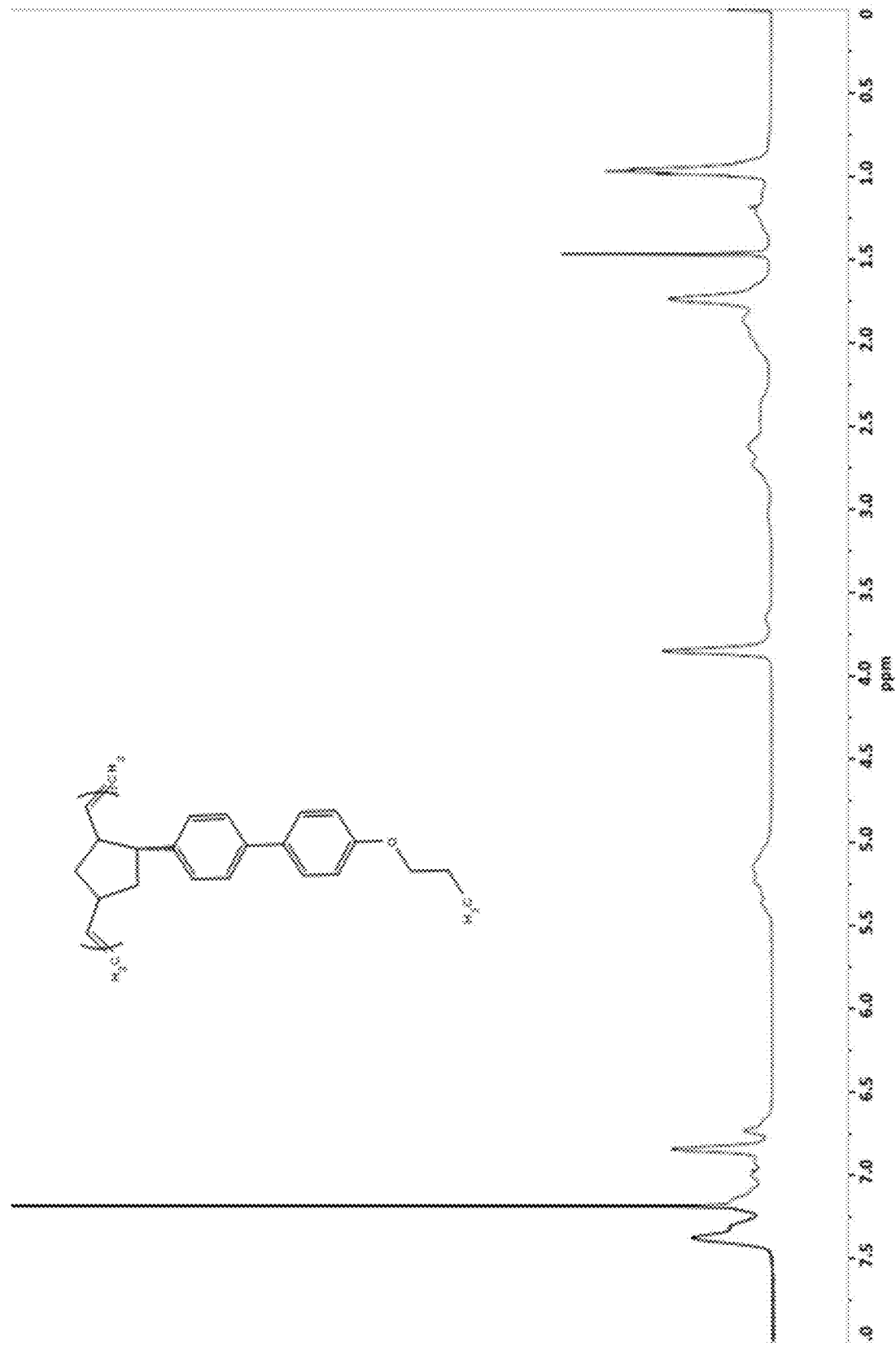
FIG. 13 is a $^1$H-NMR spectra of ROMP-N-BPP.
Figure 14:
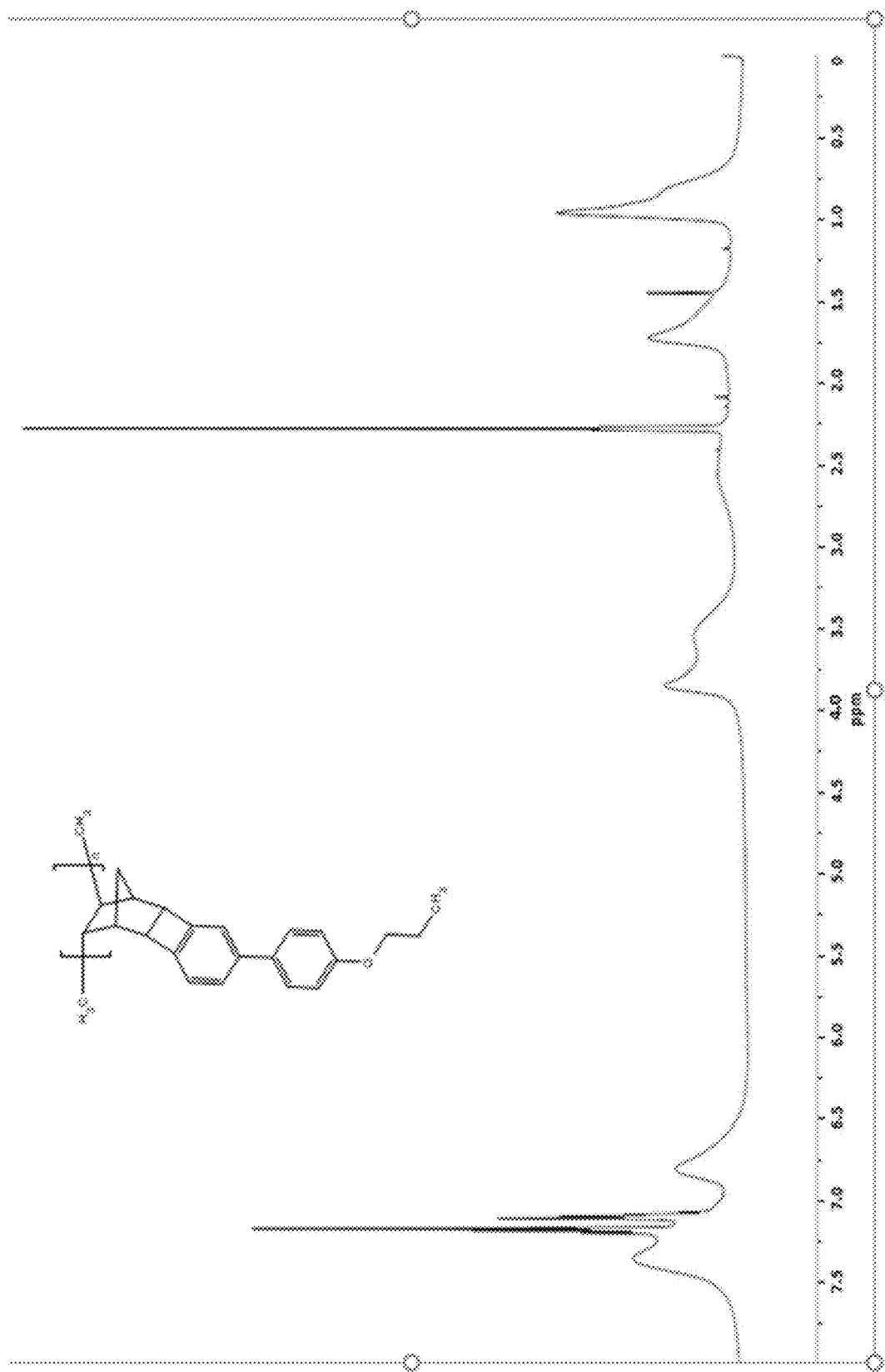
FIG. 14 is a $^1$H-NMR spectra of APTCN-BPP that has a 99.8% yield.

Structural characterization of the monomers and polymers described above are set forth in FIGS. 8-14. In particular, FIG. 8 is an $^1$H-NMR spectra of 4-biphenylpropoxy norbornene; FIG. 9 is an $^1$H-NMR spectra of 4-biphenylpropoxy tricyclononene; FIG. 10 is a $^1$H-NMR spectra of APTCN-BPP; FIG. 11 is an $^1$H-NMR spectra of ROMP-TCN-BPP; FIG. 12 is an $^1$H-NMR spectra of APN-BPP; FIG. 13 is an $^1$H-NMR spectra of ROMP-N-BPP; and FIG. 14 is an $^1$H-NMR spectra of APTCN-BPP.

Example 6

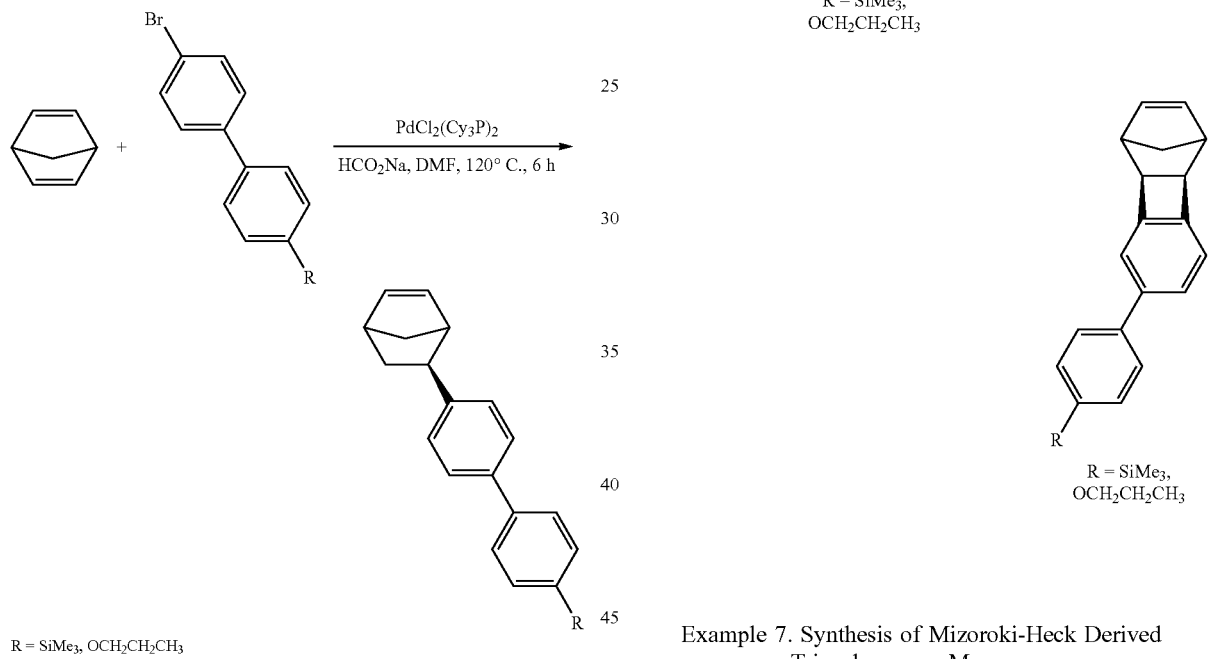

R = SiMe$_3$, OCH$_2$CH$_2$CH$_3$

Example 6. Synthesis of Mizoroki-Heck Derived Norbornene Monomers

Representative synthesis: A dried 1 L round bottom flask was equipped with a stir bar, cooled to room temperature and evacuated under vacuum. The flask was charged with nitrogen, and PdCl$_2$(PCy$_3$)$_2$ (5.112 g, 7 mmol), NaCO$_2$H (23.355 g, 343 mmol), and aryl bromide (20 g, 69 mmol) were added under an inert atmosphere. 300 mL of anhydrous DMF was added via syringe followed by norbornadiene (34.926 mL, 343 mol). The reaction was then stirred at 120° C. for six hours. The entire reaction mixture was added to 150 mL of water and diluted with 150 mL of diethyl ether. The aqueous layer was washed three times with diethyl ether, and the collected diethyl ether layers were washed with a fresh 100 mL of DI water. The organic layer was collected over MgSO$_4$ and then filtered. Diethyl ether was removed under vacuum to afford a viscous residue as the crude product, which was then purified with column chromatography using 100% hexanes as an eluent.

Example 7

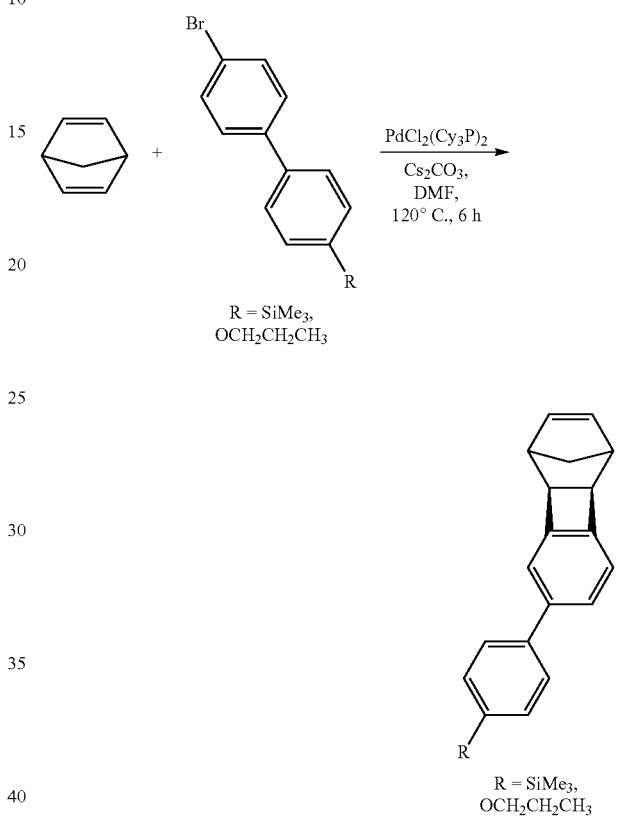

Example 7. Synthesis of Mizoroki-Heck Derived Tricyclononene Monomers

Representative synthesis: A 100-mL Schlenk flask was equipped with a stir bar, flame dried with a butane torch, cooled to room temperature and evacuated under vacuum. The flask was charged with nitrogen, and PdCl$_2$(PCy$_3$)$_2$ (0.375 g, 0.508 mmol), Cs$_2$CO$_3$ (9.220 g, 28.210 mmol), and aryl bromide (4.306 g, 14.105 mmol) were added under an inert atmosphere. 25 mL of DMF was added via syringe, followed by norbornadiene (5.738 mL, 56.421 mmol). The reaction was then stirred at 120° C. for six hours. The entire reaction mixture was added to 150 mL of water and diluted with 150 mL of diethyl ether. The aqueous layer was washed three times with diethyl ether, and the collected diethyl ether layers were washed with a fresh 100 mL of DI water. The organic layer was collected over MgSO$_4$ and then filtered. Diethyl ether was removed under vacuum to afford a brown viscous residue as the crude product, which was then purified with column chromatography using 100% hexanes as an eluent.

Example 8

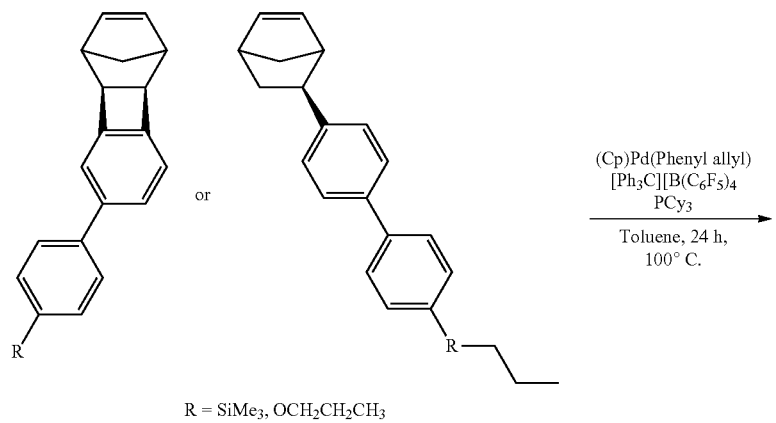

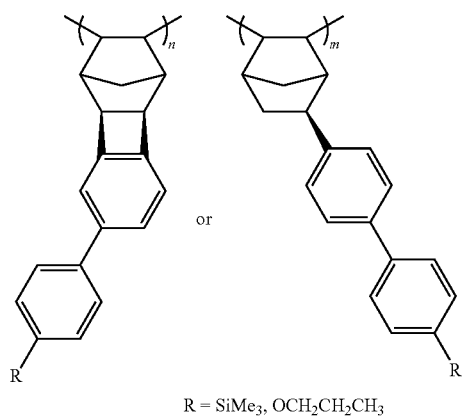

Example 8. Synthesis of Addition-Type Norbornene and Tricyclononene Polymers Representative synthesis: Under nitrogen, a 40 mL vial was charged with tricyclononene monomer (0.50 g, 1.65 mmol) and 30 mL of dry, deoxygenated toluene. In three separate vials, tricyclohexylphosphine (0.093 mg, 0.00033 mmol), cyclopentadienyl-(1,2,3-n)-1-phenyl-2-propenyl palladium (II) (0.095 mg, 0.00033 mmol), and trityl tetrakis [3,5-bis(trifluoromethyl) phenyl]borate (0.305 mg, 0.00033 mmol) were each dissolved in toluene. The palladium catalyst was thoroughly mixed with the phosphine solution, and then the trityl borate solution was added to the palladium and phosphine mixture. Afterwards, the mixed catalyst-phosphine-activator solution was added to the monomer solution. The reaction vessel was sealed and brought out of the glovebox to heat and stir at 100° C. for 24 hours, where it became viscous. After 24 hours, the solution was precipitated in 1000 mL of acetone dropwise which immediately formed small white polymer beads stirring in the acetone. The white polymer was collected via filtration and dried in vacuo to constant weight.

Example 9

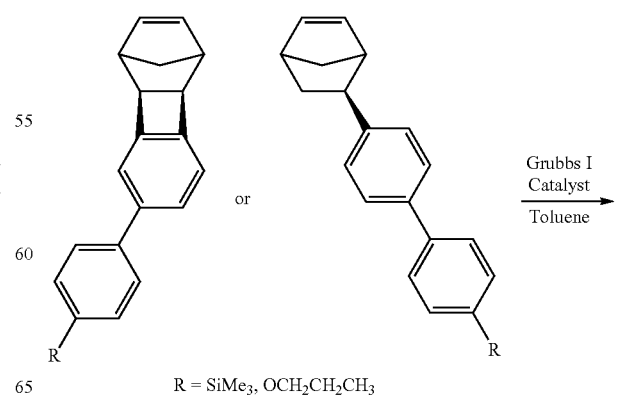

-continued

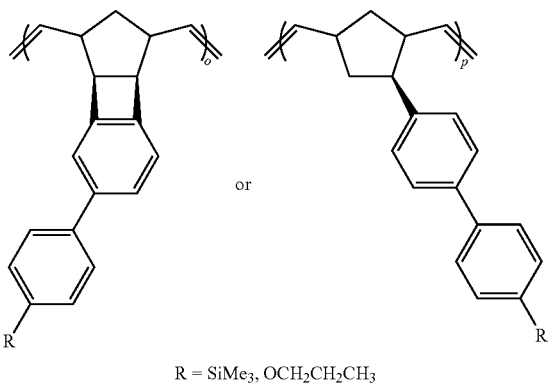

R = SiMe$_3$, OCH$_2$CH$_2$CH$_3$

Example 9. Synthesis of ROMP Norbornene and Tricyclononene Polymers

Representative synthesis: In a glovebox, a 30 mL vial was charged with tricyclononene monomer (0.500 g, 1.65 mmol) and 25 mL of dry, deoxygenated toluene. In a separate vial, Grubb's first generation catalyst (1.36 mg, 0.00165 mmol) was dissolved in 1 mL of dry toluene to create a stock catalyst solution. Finally, 0.1 mL of the catalyst solution was added to the stirring monomer solution to initiate polymerization. After 24 h, ethyl vinyl ether (0.48 mL, 5 mmol) was added to terminate the polymerization, and the solution continued to stir. After another 30 min viscous solution was precipitated dropwise into stirring acetone (1000 mL). The white polymer was collected via filtration and dried in vacuo to constant weight.

Table for Examples 6-9. This table sets forth monomer syntheses as a function of monomer type, catalyst system, stoichiometry, and reaction conditions. Table also includes norbornene structures that, due to lack of monomer reaction or purity, resulted in starting materials not suitable for polymerization.

| Structure | substituent | catalyst system | solvent | NBD mol eq. | catalyst mol eq. | co-catalyst mol eq. | Time (hr) | Temp (° C.) | Yield (%) |
|---|---|---|---|---|---|---|---|---|---|
| Norbornene (4,5-substituted) | 4: —Ph 5: —BPP | Pd(PPh$_3$)$_4$ Na$^+$Ph$_4$B$^-$ | anisole | 4.0 | 0.018 | 2 | 20 | 120 | — |
| norbornene (4,5-substituted) | 4: —Ph 5: —BPP | Pd(PPh$_3$)$_4$ Na$^+$Ph$_4$B$^-$ | DMF | 4.0 | 0.018 | 2.0 | 6 | 120 | — |
| norbornene (4,5-substituted) | 4: —Ph 5: —BPP | Pd(PPh$_3$)$_4$ Na$^+$Ph$_4$B$^-$ | DMF | 4.0 | 0.018 | 2.0 | 6 | 100 | — |
| norbornene (4,5-substituted) | 4: —Ph 5: —BPP | Pd(PPh$_3$)$_4$ Na$^+$Ph$_4$B$^-$ | DMSO | 4.0 | 0.018 | 2.0 | 6 | 100 | — |
| norbornene (4,5-substituted) | 4: —Ph 5: —BPP | Pd(PPh$_3$)$_4$ Na$^+$Ph$_4$B$^-$ | DMAc | 4.0 | 0.018 | 2.0 | 20 | 100 | — |
| norbornene (4,5-substituted) | 4: —Ph 5: —BPP | Pd(PPh$_3$)$_4$ Na$^+$Ph$_4$B$^-$ | anisole | 4.3 | 0.02 | 3.5 | 10 | 100 | — |
| norbornene (4,5-substituted) | 4: —Ph 5: —BPP | Pd(PPh$_3$)$_4$ Na$^+$Ph$_4$B$^-$ | anisole | 6.0 | 0.05 | 5.0 | 12 | 100 | — |
| norbornene (4,5-substituted) | 4: —Ph 5: —BPP | Pd(PPh$_3$)$_4$ Na$^+$Ph$_4$B$^-$ | anisole | 12.0 | 0.1 | 10.0 | 16 | 100 | — |
| norbornene (4,5-substituted) | 4: —Ph 5: —Ph | Pd(OAc)$_2$ TEMPO | AcOH | 2.0 | 0.05 | 1.5 | 12 | 30 | — |
| norbornene (4,5-substituted) | 4: —Ph 5: —Ph | Pd(OAc)$_2$ TEMPO | AcOH | 48.0 | 0.4 | 40.0 | 12 | 30 | — |
| norbornene (4-substituted) | -isatin | PdCl$_2$(PCy$_3$)$_2$ NaHCO$_2$ | DMF | 8.0 | 0.2 | 5.0 | 6 | 100 | 35* (impure) |
| norbornene (4-substituted) | -isatin | PdCl$_2$(PCy$_3$)$_2$ NaHCO$_2$ | DMF | 16.0 | 0.2 | 5.0 | 6 | 90 | — |
| norbornene (4-substituted) | -isatin | PdCl$_2$(PCy$_3$)$_2$ NaHCO$_2$ | DMF | 16.0 | 0.4 | 5.0 | 6 | 90 | 19* |
| norbornene (4-substituted) | -isatin | PdCl$_2$(PCy$_3$)$_2$ NaHCO$_2$ | DMF | 16.0 | 0.2 | 10.0 | 6 | 90 | — |
| norbornene (4-substituted) | -isatin | PdCl$_2$(PCy$_3$)$_2$ NaHCO$_2$ | DMF | 4.0 | 0.036 | 2.0 | 18 | 100 | — |
| norbornene (4-substituted) | -isatin | PdCl$_2$(PCy$_3$)$_2$ NaHCO$_2$ | DMF | 10.0 | 0.03 | 5.0 | 18 | 120 | — |
| norbornene (4-substituted) | -isatin | PdCl$_2$(PCy$_3$)$_2$ NaHCO$_2$ | DMF | 16.0 | 0.2 | 5.0 | 18 | 90 | — |
| norbornene (4-substituted) | —PhCF$_3$ | PdCl$_2$(PCy$_3$)$_2$ NaHCO$_2$ | DMF | 8.0 | 0.2 | 5.0 | 6 | 120 | 15* |
| norbornene (4-substituted) | —PhCF$_3$ | PdCl$_2$(PCy$_3$)$_2$ NaHCO$_2$ | DMF | 16.0 | 0.2 | 5.0 | 6 | 120 | 31* |

-continued

| Structure | substituent | catalyst system | solvent | NBD mol eq. | catalyst mol eq. | co-catalyst mol eq. | Time (hr) | Temp (° C.) | Yield (%) |
|---|---|---|---|---|---|---|---|---|---|
| norbornene (4-substituted) | —PhCF$_3$ | PdCl$_2$(PCy$_3$)$_2$ NaHCO$_2$ | DMF | 16.0 | 0.4 | 5.0 | 6 | 120 | 58* |
| norbornene (4-substituted) | —PhCF$_3$ | PdCl$_2$(PCy$_3$)$_2$ NaHCO$_2$ | DMF | 10.0 | 0.03 | 5.0 | 18 | 120 | — |
| norbornene (4-substituted) | —PhCF$_3$ | PdCl$_2$(PCy$_3$)$_2$ NaHCO$_2$ | DMF | 16.0 | 0.30 | 5.0 | 18 | 120 | 14 (90% p) |
| tricyclononene | —PhCF$_3$ | PdCl$_2$(PCy$_3$)$_2$ Cs$_2$CO$_3$ | DMF | 4.0 | 0.036 | 2.0 | 6 | 120 | — |
| norbornene (4-substituted) | -fluorene | PdCl$_2$(PCy$_3$)$_2$ NaHCO$_2$ | DMF | 8.0 | 0.2 | 5.0 | 6 | q | 30* |
| norbornene (4-substituted) | -fluorene | PdCl$_2$(PCy$_3$)$_2$ NaHCO$_2$ | DMF | 16.0 | 0.2 | 10.0 | 6 | 90 | 67* |
| norbornene (4-substituted) | -fluorene | PdCl$_2$(PCy$_3$)$_2$ NaHCO$_2$ | DMF | 8.0 | 0.4 | 5.0 | 6 | 90 | 50* |
| norbornene (4-substituted) | -fluorene | PdCl$_2$(PCy$_3$)$_2$ NaHCO$_2$ | DMF | 16.0 | 0.2 | 10.0 | 18 | 100 | 46 |
| norbornene (4-substituted) | -fluorene | PdCl$_2$(PCy$_3$)$_2$ NaHCO$_2$ | DMF | 16.0 | 0.2 | 10.0 | 18 | 90 | — |
| norbornene (4-substituted) | -fluorene | PdCl$_2$(PCy$_3$)$_2$ NaHCO$_2$ | DMF | 10.0 | 0.030 | 5.0 | 18 | 120 | 50 |
| norbornene (4-substituted) | —PhSiMe$_3$ | PdCl$_2$(PCy$_3$)$_2$ NaHCO$_2$ | DMF | 8.0 | 0.2 | 5.0 | 6 | 120 | 29* |
| norbornene (4-substituted) | —PhSiMe$_3$ | PdCl$_2$(PCy$_3$)$_2$ NaHCO$_2$ | DMF | 16.0 | 0.2 | 10.0 | N/A | 120 | — |
| norbornene (4-substituted) | —PhSiMe$_3$ | PdCl$_2$(PCy$_3$)$_2$ NaHCO$_2$ | DMF | 30.0 | 0.2 | 20.0 | 6 | 120 | — |
| norbornene (4-substituted) | —PhSiMe$_3$ | PdCl$_2$(PCy$_3$)$_2$ NaHCO$_2$ | DMF | 10.0 | 0.030 | 5.0 | 18 | 120 | — |
| norbornene (4-substituted) | —PhSiMe$_3$ | PdCl$_2$(PCy$_3$)$_2$ NaHCO$_2$ | DMF | 16.0 | 0.30 | 5.0 | 18 | 120 | 20 |
| norbornene (4-substituted) | —PhSiMe$_3$ | PdCl$_2$(PCy$_3$)$_2$ NaHCO$_2$ | DMF | 10.0 | 0.030 | 5.0 | 18 | 120 | — |
| norbornene (4-substituted) | —PhSiMe$_3$ | PdCl$_2$(PCy$_3$)$_2$ NaHCO$_2$ | DMF | 10.0 | 0.030 | 5.0 | 4 | 120 | — |
| norbornene (4-substituted) | —PhSiMe$_3$ | PdCl$_2$(PCy$_3$)$_2$ NaHCO$_2$ | DMF | 10.0 | 0.030 | 5.0 | 6 | 120 | — |
| tricyclononene | —PhSiMe$_3$ | PdCl$_2$(PCy$_3$)$_2$ Cs$_2$CO$_3$ | DMF | 4.0 | 0.036 | 2.0 | 6 | 120 | 53 |
| tricyclononene | —PhSiMe$_3$ | PdCl$_2$(PCy$_3$)$_2$ Cs$_2$CO$_3$ | DMF | 4.0 | 0.036 | 2.0 | 6 | 120 | — |
| tricyclononene | —BPP | PdCl$_2$(PCy$_3$)$_2$ Cs$_2$CO$_3$ | DMF | 4.0 | 0.036 | 2.0 | 6 | 120 | — |
| tricyclononene | —BPP | PdCl$_2$(PCy$_3$)$_2$ Cs$_2$CO$_3$ | DMF | 9.0 | 0.1 | 2.0 | 6 | 120 | 71 |
| tricyclononene | —BPP | PdCl$_2$(PCy$_3$)$_2$ Cs2CO3 | DMF | 8.0 | 0.075 | 2.0 | 6 | 120 | 64 |
| tricyclononene | —BPP | PdCl$_2$(PCy$_3$)$_2$ Cs$_2$CO$_3$ | DMF | 8.0 | 0.1 | 2.0 | 6 | 120 | 65 |
| tricyclononene | —BPP | PdCl$_2$(PCy$_3$)$_2$ Cs$_2$CO$_3$ | DMF | 9.0 | 0.075 | 2.0 | 6 | 120 | 66 |
| tricyclononene | —BPP | PdCl$_2$(PCy$_3$)$_2$ Cs$_2$CO$_3$ | DMF | 10.0 | 0.1 | 2.0 | 6 | 120 | 65 |
| tricyclononene | —BPP | PdCl$_2$(PCy$_3$)$_2$ Cs$_2$CO$_3$ | DMF | 4.0 | 0.036 | 2.0 | 20 | 120 | — |
| tricyclononene | —BPP | PdCl$_2$(PCy$_3$)$_2$ Cs$_2$CO$_3$ | DMF | 4.0 | 0.036 | 2.0 | 6 | 120 | — |
| tricyclononene | —BPP | PdCl$_2$(PCy$_3$)$_2$ Cs$_2$CO$_3$ | DMF | 6.0 | 0.036 | 2.0 | 6 | 120 | — |
| tricyclononene | —BPP | PdCl$_2$(PCy$_3$)$_2$ Cs$_2$CO$_3$ | DMF | 8.0 | 0.036 | 2.0 | 6 | 120 | — |
| tricyclononene | —BPP | PdCl$_2$(PCy$_3$)$_2$ Cs$_2$CO$_3$ | DMF | 8.0 | 0.075 | 2.0 | 6 | 120 | — |
| Norbornene | —BPP | PdCl$_2$(PCy$_3$)$_2$ NaHCO$_2$ | DMF | 5.0 | 0.1 | 5.0 | 6 | 120 | N/A |
| tricyclononene | —BPTMS | PdCl$_2$(PCy$_3$)$_2$ Cs$_2$CO$_3$ | DMF | 4.0 | 0.036 | 2.0 | 6 | 120 | 19 |
| tricyclononene | —BPTMS | PdCl$_2$(PCy$_3$)$_2$ Cs$_2$CO$_3$ | DMF | 4.0 | 0.036 | 2.0 | 6 | 120 | 18 |

Table for Examples 6-9. Polymer syntheses as a function of monomeric starting material and reaction conditions

| polymer | Monomer | catalyst system | solvent | Time (hr) | Temp (° C.) | Yield (%) | Mw | Mn | Mw/Mn |
|---|---|---|---|---|---|---|---|---|---|
| APN—BPP | propoxy norbornene | Cp(Pd)phenylallyl Trityl BArF/PCy$_3$ | toluene | 24 | 100 | 80 | | not measured | |
| APN—BPP | propoxy norbornene | Cp(Pd)phenylallyl Trityl BArF/PCy$_3$ | toluene | 24 | 100 | 44 | 7.20 × 10$^5$ | 2.68 × 10$^5$ | 2.69 |
| APN—BPP | propoxy norbornene | Cp(Pd)phenylallyl Trityl BArF/PCy$_3$ | toluene | 24 | 100 | 88 | | not measured | |
| APTCN—BPP | propoxy tricyclononene | Cp(Pd)phenylallyl Trityl BArF/PCy$_3$ | toluene | 24 | 100 | 80 | | not measured | |
| APTCN—BPP | propoxy tricyclononene | Cp(Pd)phenylallyl Trityl BArF/PCy$_3$ | toluene | 18 | 100 | 100 | 1.78 × 10$^6$ | 1.08 × 10$^6$ | 1.66 |
| APTCN—BPTMS | TMS tricyclononene | Cp(Pd)phenylallyl Trityl BArF/PCy$_3$ | toluene | 18 | 100 | No RXN | | not measured | |
| APTCN—BPTMS | TMS tricyclononene | Cp(Pd)phenylallyl Trityl BArF/PCy$_3$ | toluene | 18 | 100 | 67 | 1.49 × 10$^6$ | 0.85 × 10$^6$ | 1.74 |
| ROMP—N—BPP | Propoxy norbornene | Grubbs 3$^{rd}$ gen. | toluene | 18 | 40 | 72 | | not measured | |
| ROMP—N—BPP | Propoxy norbornene | Grubbs 1$^{st}$ gen. | toluene | 18 | 40 | 88 | 2.45 × 10$^5$ | 0.64 × 10$^5$ | 3.83 |
| ROMP—TCN—BPP | propoxy tricyclononene | Grubbs 1$^{st}$ gen. | toluene | 18 | 40 | 72 | | not measured | |
| ROMP—TCN—BPP | Propoxy tricyclononene | Grubbs 1$^{st}$ gen. | toluene | 18 | 40 | 94 | 3.53 × 10$^5$ | 0.90 × 10$^5$ | 3.93 |

Figure 15:
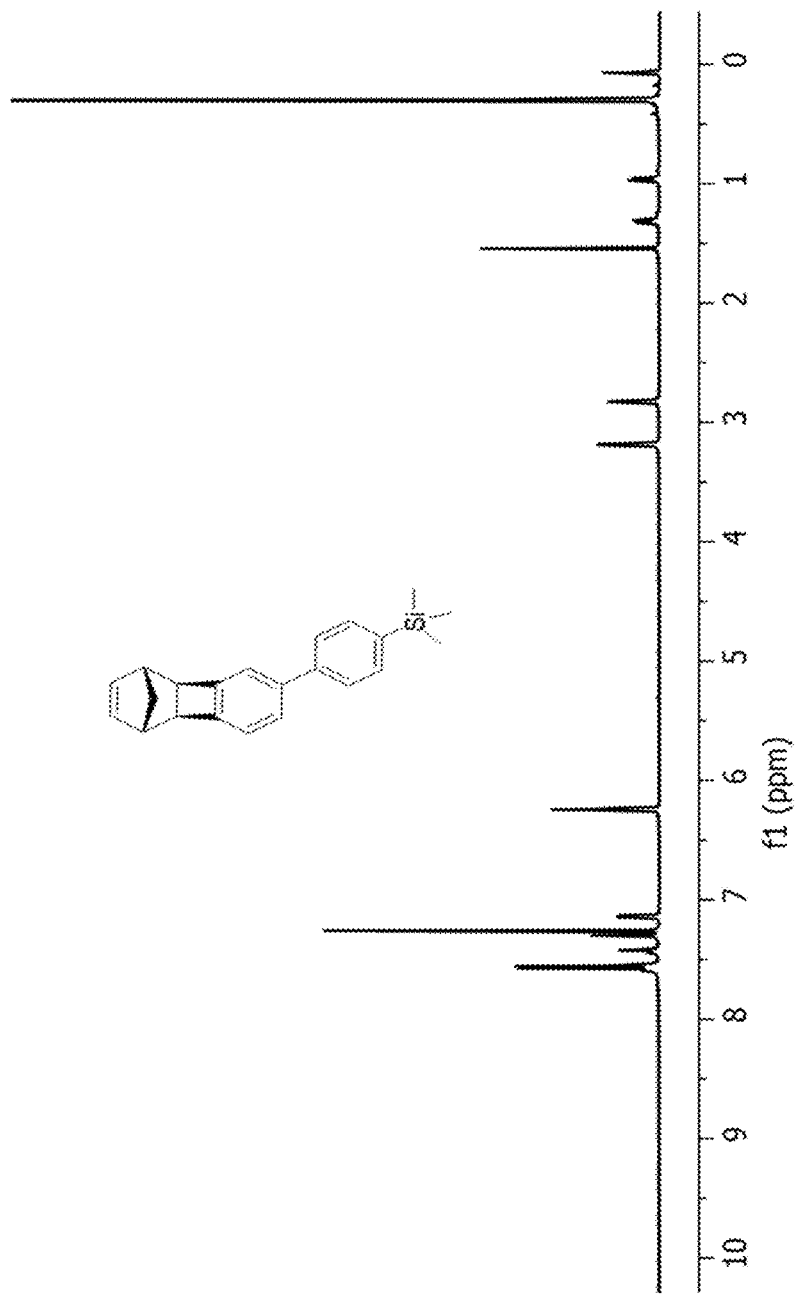
FIG. 15 is a $^1$H-NMR spectra of 4-biphenyltrimethylsilyl tricyclononene.
Figure 16:
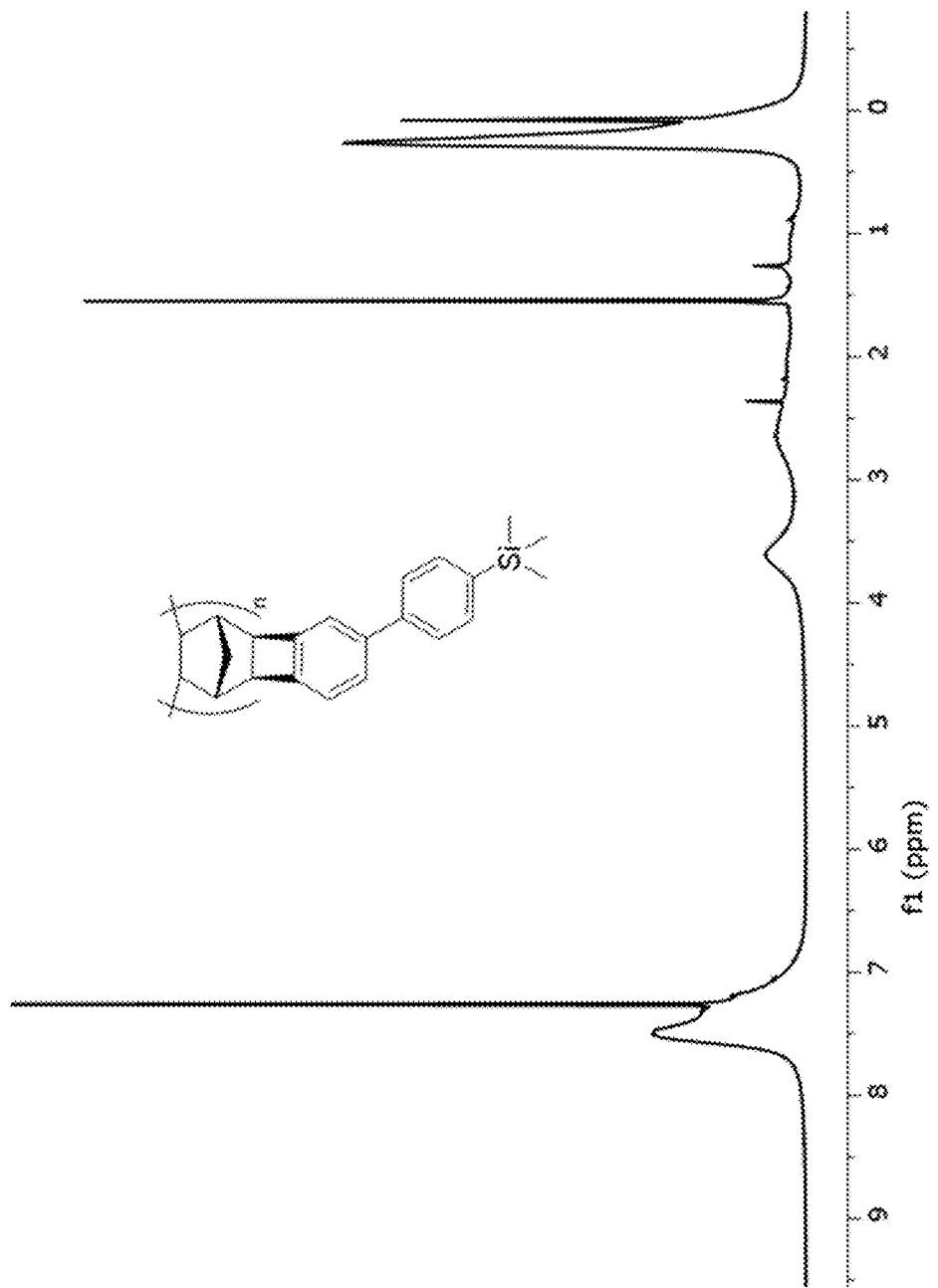
FIG. 16 is a $^1$H-NMR spectra of APNTCN-BPTMS.

Structural characterization of the monomers and polymers described above are set forth in FIGS. 15-16. In particular, FIG. 15 is an $^1$H-NMR spectra of 4-biphenyltrimethylsilyl tricyclononene and FIG. 16 is an $^1$H-NMR spectra of APNTCN-BPTMS.

Figure 20:
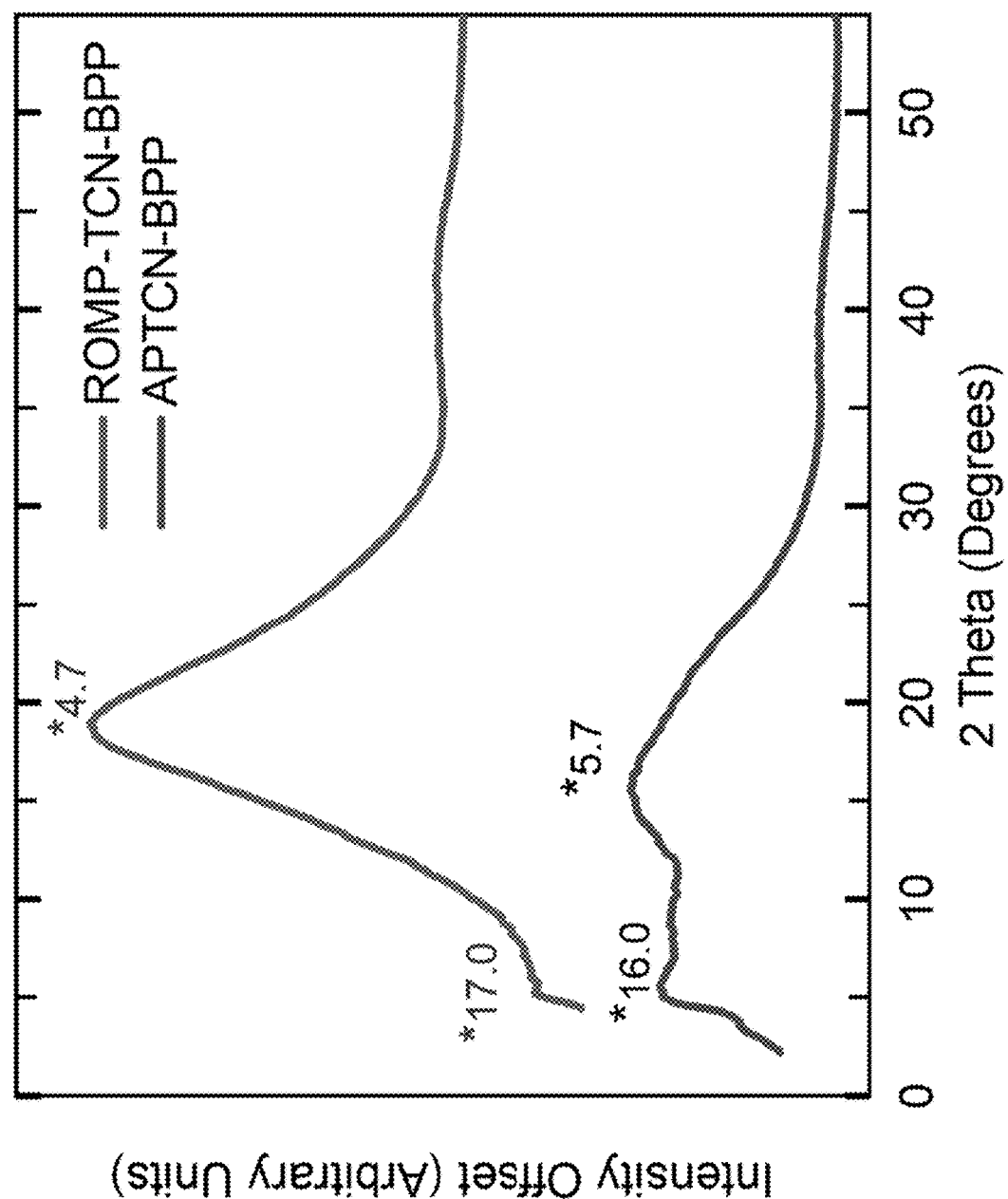
FIG. 20 is a graph that shows the XRD traces of ROMP-TCN-BPP and APTCN-BPP.
Figure 21:
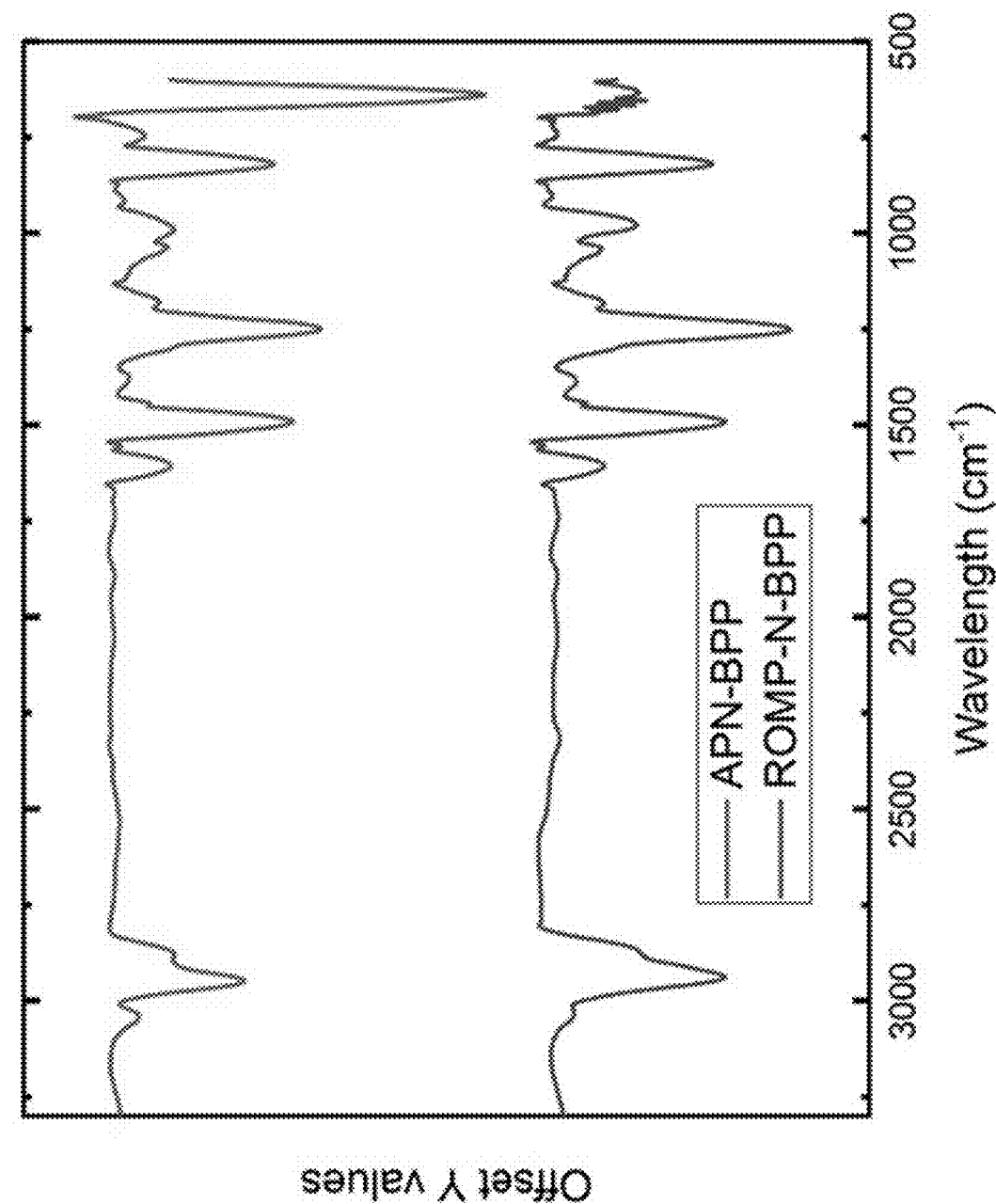
FIG. 21 is graph of FTIR spectra comparing addition-type and ROMP polymers using biphenyl propoxy norbornene monomers.
Figure 22:
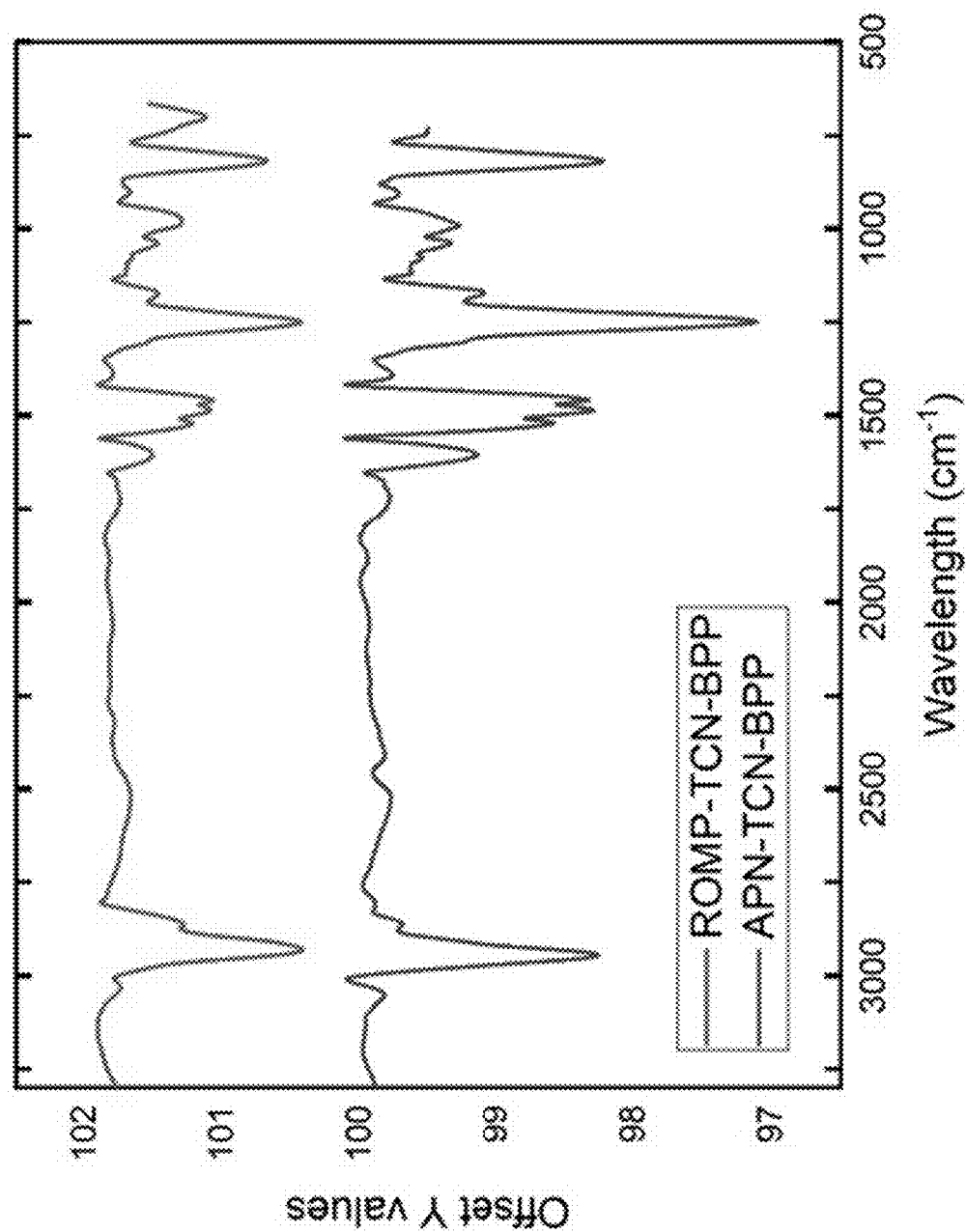
FIG. 22 is graph of FTIR spectra comparing addition-type and ROMP polymers using biphenyl propoxy tricyclononene monomers.
Figure 23:
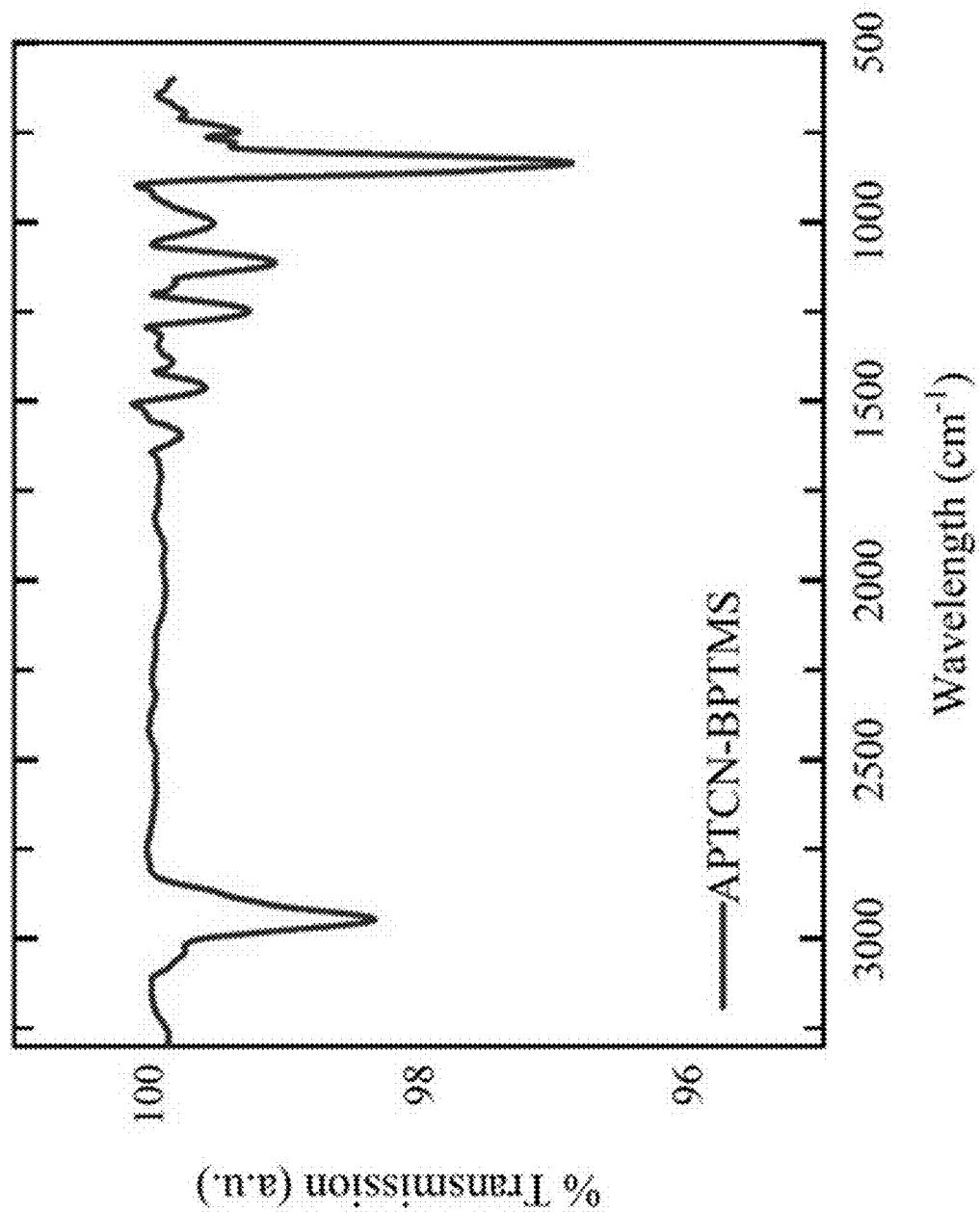
FIG. 23 is a graph of FTIR spectra for the addition-type polymers using trimethylsilyl substituted tricyclononene monomers.
Figure 24:
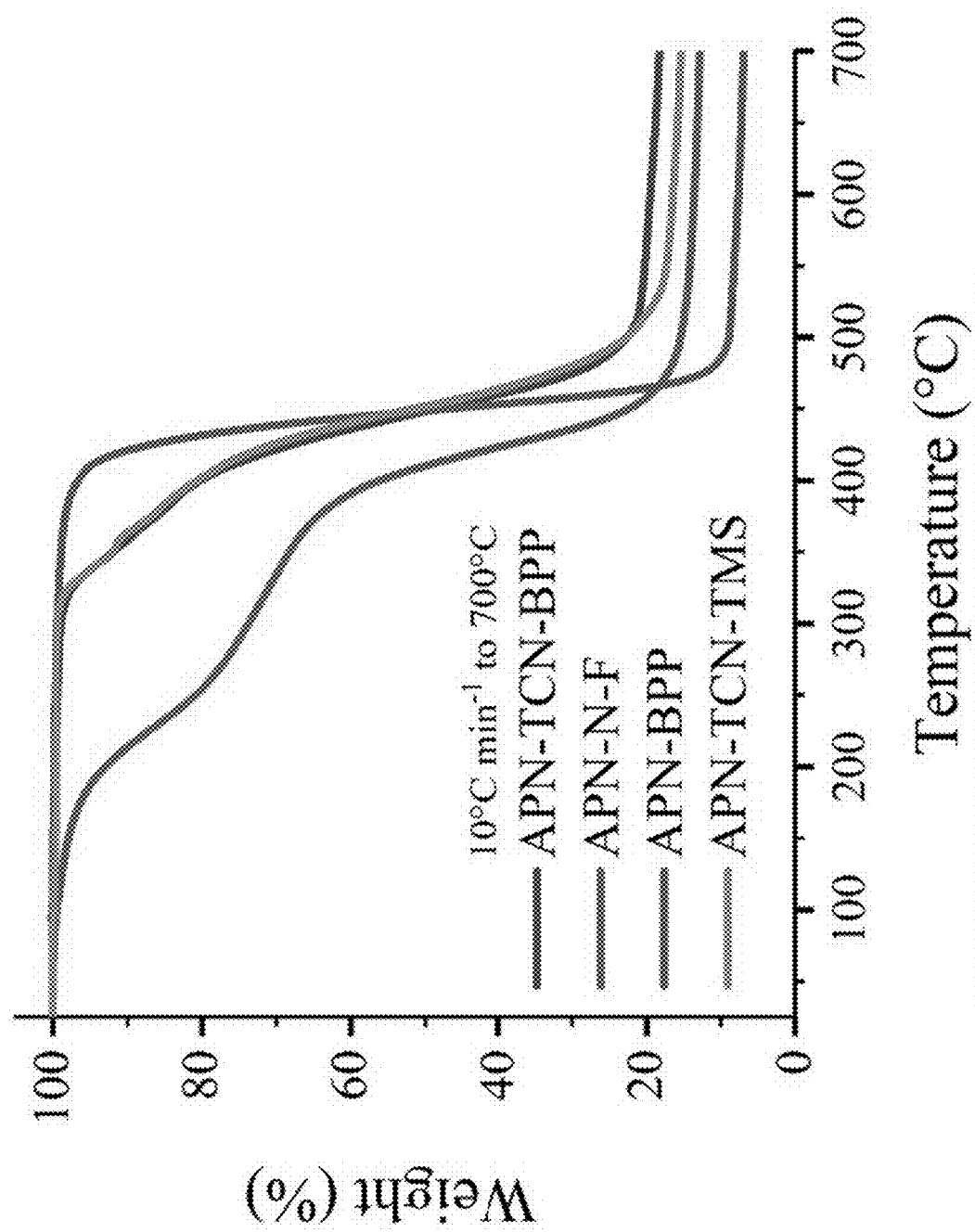
FIG. 24 illustrates that TGA thermograms comparing the addition-type polymers showed consistently high thermal stabilities (excluding APN-N-F, an impure fluorene based polynorbornene.
Figure 25:
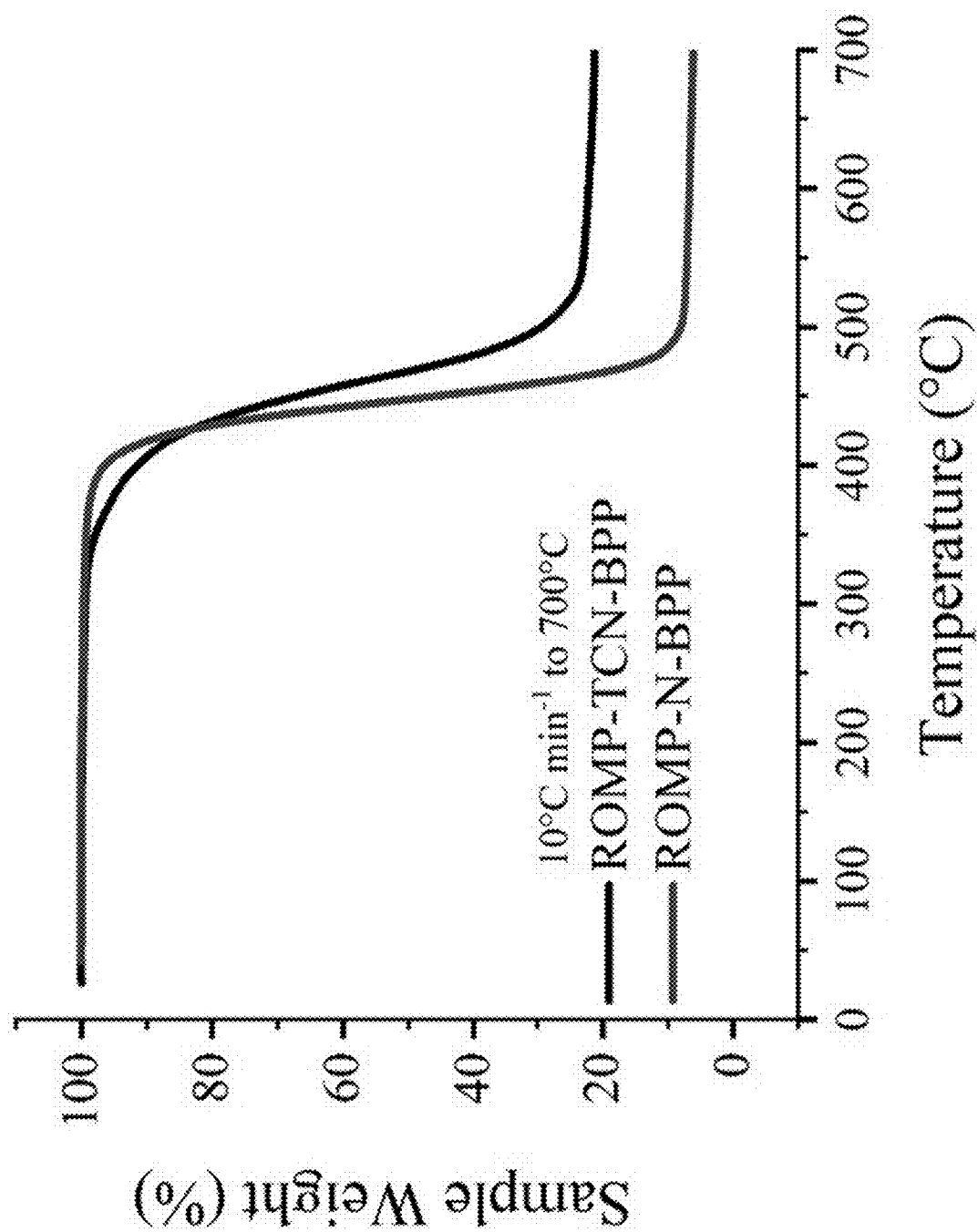
FIG. 25 illustrates that TGA thermograms comparing the ROMP polymers showed consistently high thermal stabilities.

FIG. 20 is a graph that shows the XRD traces of ROMP-TCN-BPP and APTCN-BPP. FIG. 21 is graph of FTIR spectra comparing addition-type and ROMP polymers using biphenyl propoxy norbornene monomers. FIG. 22 is graph of FTIR spectra comparing addition-type and ROMP polymers using biphenyl propoxy tricyclononene monomers. FIG. 23 is a graph of the FTIR spectra of addition-type polymers using trimethylsilyl substituted tricyclononene monomers. FIG. 24 illustrates that TGA thermograms comparing the addition-type polymers showed consistently high thermal stabilities (excluding APN-N-F, and impure fluorene based polynorbornene. FIG. 25 illustrates that TGA thermograms comparing the ROMP polymers showed consistently high thermal stabilities.

Gas Separation Membranes

As stated above, typical gas separation membranes operate based on diffusion selectivity, where gases with smaller kinetic diameters permeate through polymeric membranes at a faster rate compared to gases with a larger kinetic diameter. The gases most often referred to in this application, methane, propane and butane, are shown in FIG. 1 with their corresponding kinetic diameters.

In accordance with the present disclosure, the norbornene polymers described herein (e.g., the high molecular weight polymers that are formed according to the reactions of FIG. 3(c) or FIG. 3(d) are particularly suited for use in forming gas separation membranes.

Figure 6:
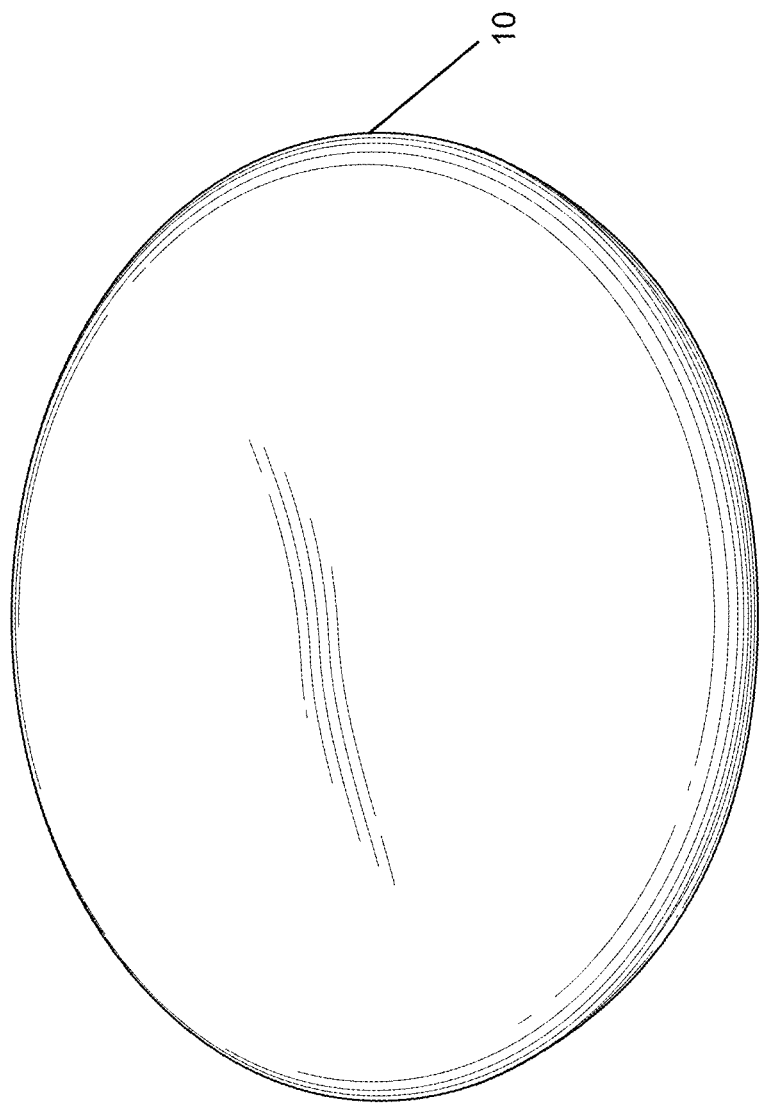
FIG. 6 illustrates a homogenous polymeric film formed of a Mizoroki-Heck derived polynorbornene.

For example, upon achieving the high molecular weight (norbornene) polymers that are disclosed herein, the polymers are then precipitated into appropriate non-solvents, dried and isolated. Non-solvents used in the present disclosure include, but are not limited to, acetone, methanol, and ethanol. It will be appreciated that the list on non-solvents can extend to other solvents with similarly high polarity, including, but not limited to, isopropyl alcohol, butanol, and potentially water. The polymers may then be dissolved in appropriate solvents, such as toluene, to form a viscous homogenous solution. This solution may then be cast using a variety of suitable methods apparent to those skilled in the art to form a homogenous polymeric film 10 that is illustrated in FIG. 6. The film 10 of FIG. 6 comprises an exemplary dense free-standing film that is suitable for testing of permeation and separation of natural gas liquids from natural gas. Thus, film 10 can be incorporated into a device for natural gas upgrading.

The polymeric films 10 can be produced via the following procedure. The polymer ((e.g., polynorbornene), having a weight of 0.5 g) is dissolved in 10 ml of toluene and is stirred until the polymer is completely dissolved and is filtered with a suitable filter, such as 0.45 μm syringe filters. The filtered polymer solutions are then poured into 10 cm diameter PFA molds on a level surface. The PFA mold is covered to slow the rate of evaporation, and the film is allowed to dry overnight. The polymer film is removed from the PFA mold and dried to constant weight under vacuum. The polymer films that are obtained are transparent, ductile, and colorless.

It will be appreciated that other suitable techniques can be used to form the polymer films.

Pure Gas and Mixed Gas Permeation Tests

Pure gas and mixed gas permeation tests were performed as follows. Gas permeation was conducted using a constant volume, variable pressure technique. The downstream side of the membrane (formed of film 10) was maintained at less than 25 torr using a vacuum pump. To keep the feed composition constant, a retentate stream was applied. The retentate flow was adjusted to 100 times the permeate flow. The composition of the permeate stream was measured using a Shimadzu gas chromatograph (GC) equipped with a thermal conductivity detector. A pump (e.g., Teledyne Isco) was used to control the feed pressure. The feed gas has heated to 90° C. to maintain the feed above its hydrocarbon dew point of around 70° C. at 800 psi. The membrane cell was kept at room temperature.

Permeability was calculated using Equation 1 set forth below, wherein $y_i$ is downstream mole fraction, l the membrane thickness and $\Delta f_i$ is the partial fugacity difference across the membrane. A fugacity driving force was used rather than partial pressure to correct for gas phase non-idealities. Fugacity coefficients were calculated using the Peng Robinson equation of state. The steady-state flux, or flux$_{total}$, was calculated by measuring the downstream pressure rise (dp/dt) after 30 minutes of permeation time. This time was well beyond the steady-state time estimated from 14× the pure gas time lag which equated to approximately 10 minutes for the slowest gas (methane). At 800 psi, the permeability was measured after 1 hour of permeation time to allow for any swelling induced relaxations to set-in.

$$P_i = \frac{f^{flux}{}_{total} \cdot y_i \cdot l}{\Delta f_i} \quad (1)$$

$$SF = \frac{[y_i/y_j]}{[x_i/x_j]} \quad (2)$$

$$\alpha_f = P_i/P_j \quad (3)$$

Figure 17:
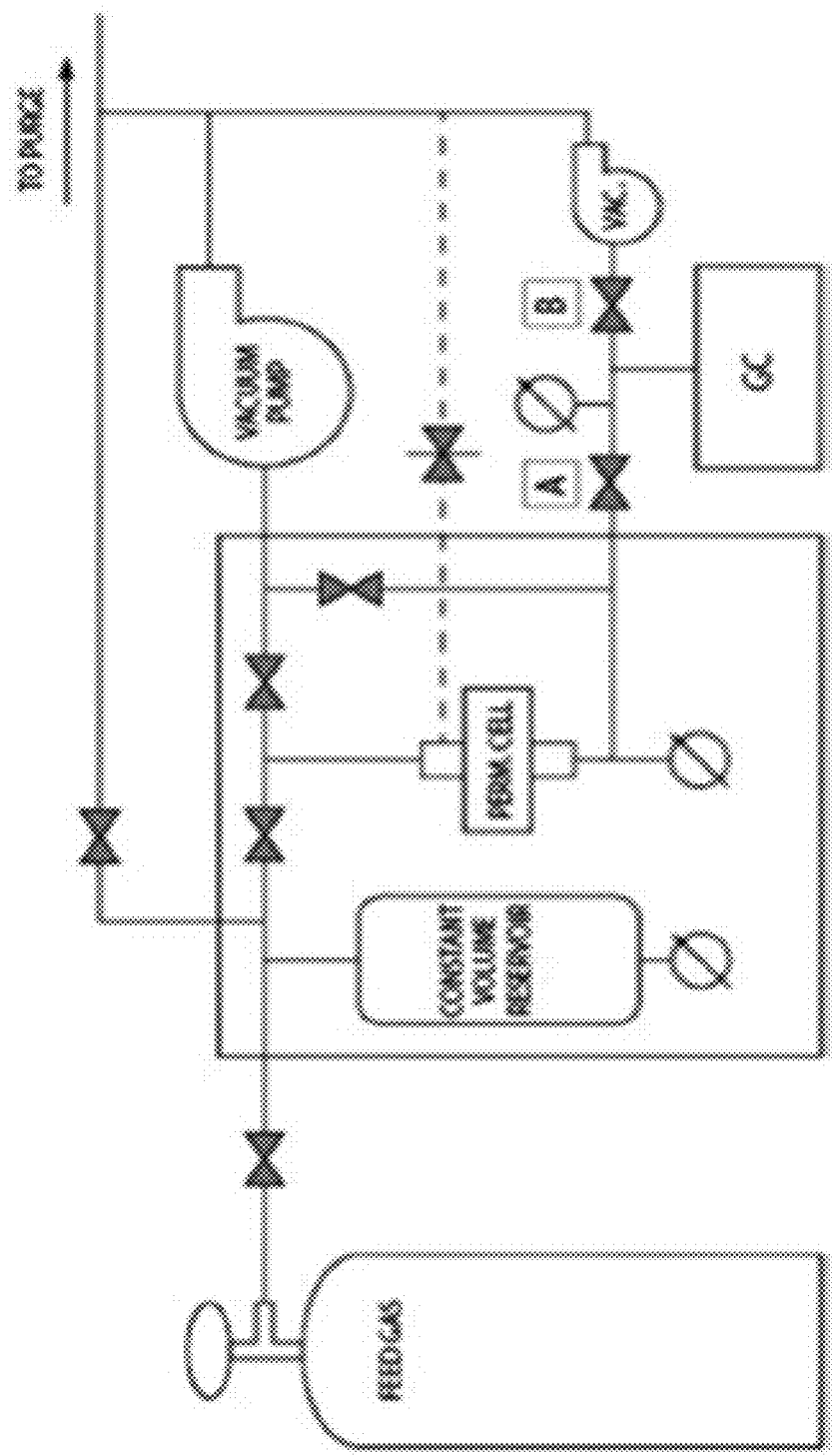
FIG. 17 is a schematic of a gas permeation cell used for pure and mixed gas experimentation.

The fugacity selectivity (above Equation 3) may be obtained by taking the ratio of gas permeabilities described in Equation 1. A schematic of the gas permeability cell 100 that was used for the pure and mixed gas experimentation is set forth in FIG. 17. In FIG. 17, the source of feed gas is indicated at 110 and the system has a number of valves that are indicated by traditional valve symbols commonly used in the art. A gas chromatograph 120 is shown and several vacuum pumps are shown using conventional symbols and notation.

Figure 18:
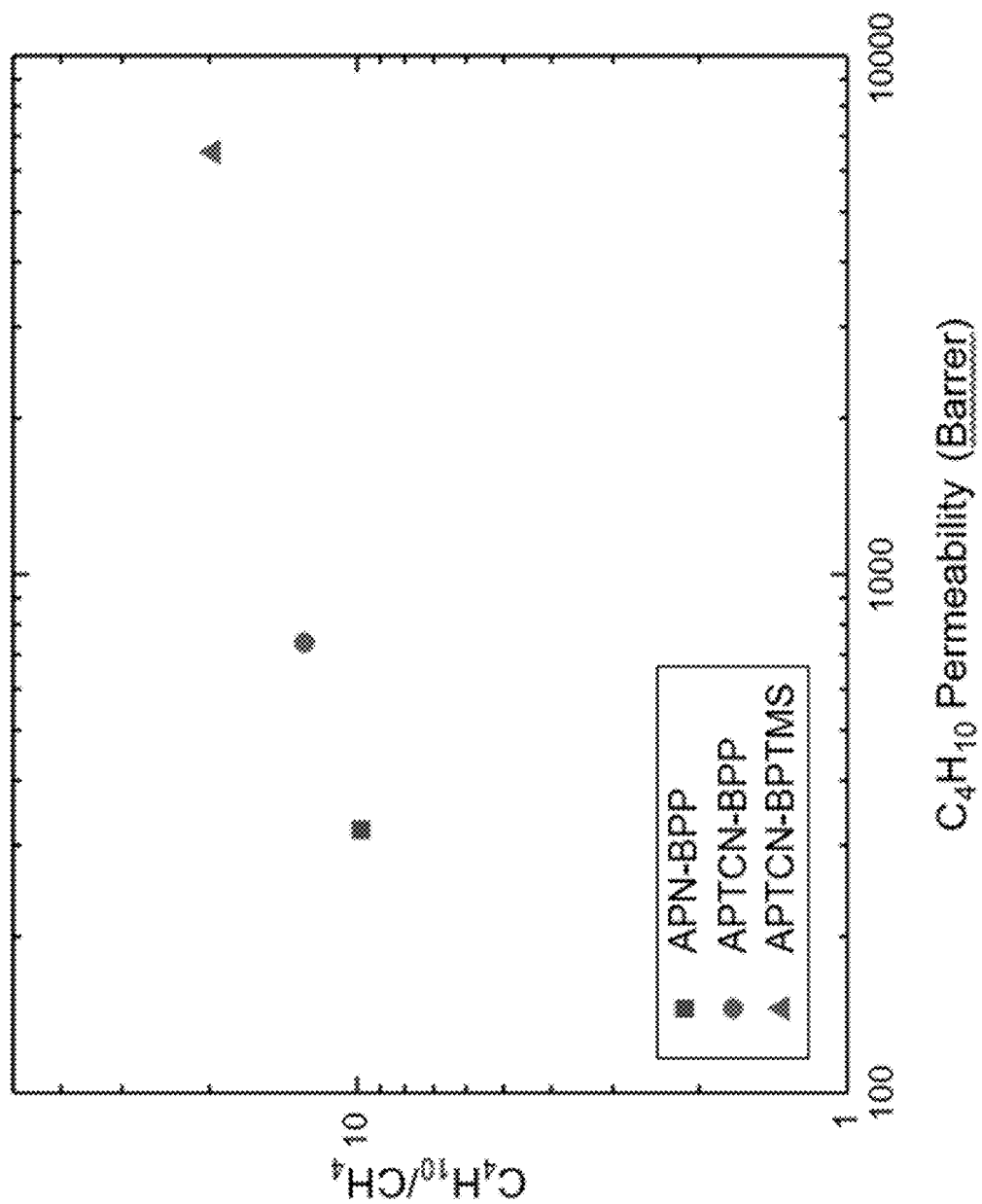
FIG. 18 is a graph of fugacity selectivity for the $C_4H_{10}$/$CH_4$ plotted as a function of fugacity $C_4H_{10}$ permeability.
Figure 19:
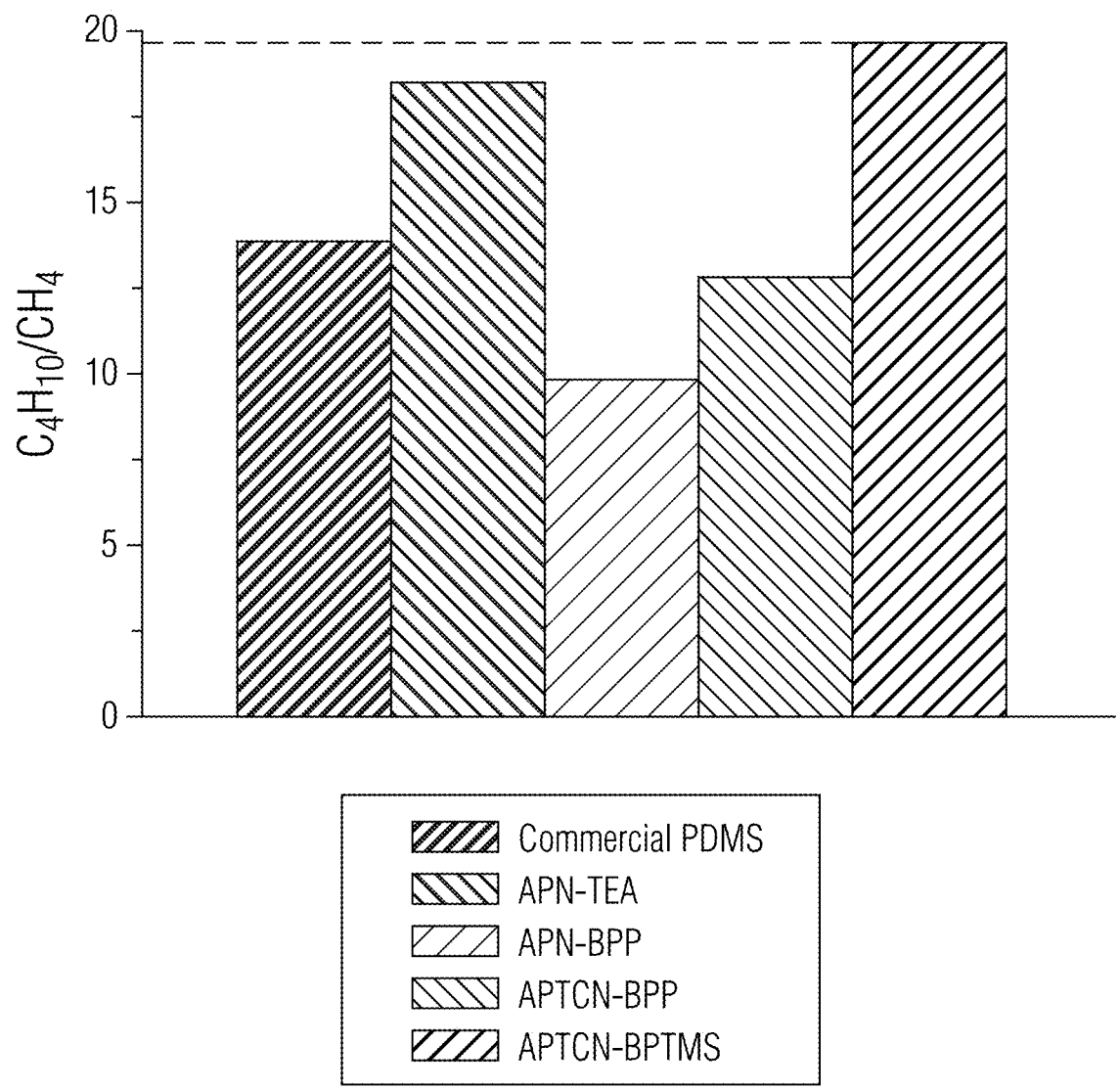
FIG. 19 is a chart that compares the $C_4H_{10}$/$CH_4$ fugacity selectivity for three Heck derived addition-type polynorbornenes to a previously published addition-type polynorbornene (APN-TEA) and commercially PDMS.

The results of the pure gas experimentation are shown in Table 1 (set forth below) and the results of the mixed gas experimentation are shown in FIGS. 18 and 19.

TABLE 1

Pure gas data of exemplary ROMP and addition type Mizoroki-Heck reaction derived polymers

| Pure Gas:[a] | $CH_4$ (Barrer) | $C_3H_8$ (Barrer) | $C_4H_{10}$ (Barrer) | SF ($C_3H_8/CH_4$) | SF ($C_4H_{10}/CH_4$) |
|---|---|---|---|---|---|
| APTCN-BPP | 13.20 | 19.11 | 332.17 | 1.45 | 25.16 |
| ROMP-TCN-BPP | 204.12 | [b] | 1.54 | [b] | 0.01 |
| APN-BPP | 3.31 | [b] | 49.71 | [b] | 15.00 |
| ROMP-N-BPP | 0.74 | 0.27 | [b] | 0.36 | [b] |

[a]14.5 psi upstream pressure at 25° C.:
[b]too slow to measure

The pure gas results indicate that at least several of the Mizoroki-Heck derived polynorbornenes are suitable candidates for heavy hydrocarbon separations, particularly, the addition-type polymers, APTCN-BPP and APN-BPP (as evidenced by SF($C_4H_{10}/CH_4$)>>1). It should be noted that mixed gas permeation varies widely from pure gas experimentation and mixed gas permeation more closely approximates field performance. As a result, the pure gas data shown in Table 1 is suitable for fundamental comparisons, while the data shown in FIGS. 18 and 19 are more indicative of industrial efficacy.

FIG. 18 demonstrates that all of the addition-type polymers tested have $C_4H_{10}/CH_4$ selectivities much greater than 1, thereby confirming their solubility selectivity. In the graph of FIG. 18, fugacity selectivity for the $C_4H_{10}/CH_4$ is plotted as a function of fugacity $C_4H_{10}$ permeability. These "upper-bound" type plots typically show a trade-off relationship between selectivity and permeability, but like many other reverse-selective materials, this plot shows simultaneous improvements in permeability and selectivity. The fugacity selectivity for $C_4H_{10}/CH_4$ improved in the order of APN-BPP (9.82, no additional cyclobutene ring or trimethyl silyl group), to APTCN-BPTMS (19.63, both additional cyclobutene ring and trimethyl silyl group). FIG. 19 compares the $C_4H_{10}/CH_4$ fugacity selectivity for three Heck derived addition-type polynorbornenes to a previously published addition-type polynorbornene (APN-TEA) and commercially PDMS. Notably, the highest performing Heck polynorbornenes, APTCN-BPTMS, had a $C_4H_{10}/CH_4$ fugacity selectivity of 19.63, an improvement compared to APN-TEA (18.53) and a significant improvement over commercial PDMS (13.94).

Exemplary Applications for Polynorbornenes

It will also be appreciated that the polynorbornene derivatives described in the present application are suitable as insulating materials in the manufacturing of integrated circuits due to their low dielectric constants, high hydrophobicity (low moisture uptake), chemical resistance, and high glass transition temperatures.

It will further be appreciated that the aforementioned applications, including a gas separation membrane, are only exemplary in nature and other applications for the polynorbornenes that are formed are equally possible.

FEATURES OF THE PRESENT DISCLOSURE

In one aspect of the present disclosure, it was discovered that the exclusive formation of the substituted norbornene exo isomer (resulting from the Mizoroki-Heck reaction) favors the formation of a high molecular weight polymer (polynorbornenes) which is necessary for membrane formation in (gas) separation applications.

In one aspect of the present disclosure, the Mizoroki-Heck reaction is used to synthesize novel substituted norbornene monomers that will lead to polynorbornenes with enhanced gas separation properties over the 4-substituted analogs due to the incorporation of the benzocyclobutene-fused moiety.

In another aspect, the incorporation of alkoxysilyl content in the substituted norbornene structures (4-substituted derivatives, 4, 5-substituted derivatives, tricyclononene derivatives) imbues the resulting polynorbornenes with acid/base catalyzed crosslinkability to stabilize the resulting membranes against plasticization, swelling, and physical aging in the presence of aggressive gas compositions.

In yet another aspect, the incorporation of alkoxysilyl content in the substituted norbornene structures (4-substituted derivatives, 4, 5-substituted derivatives, tricyclononene derivatives) imbues the resulting polynorbornenes with good adhesion properties to various substrates (e.g., metal, glass, etc.) to enhance their applicability as good insulating materials with low dielectric constants in the manufacturing of integrated circuits.

In one aspect, the present process and its propensity to the exclusive formation of the substituted norbornene exo isomer favors the formation of high molecular weight polymer which is a necessary result for membrane formation in separation applications.

The present disclosure sets forth a series of addition-type and ROMP type polynorbornenes with substituents derived from Mizoroki-Heck reactions. Mizoroki-Heck derived polynorbornenes can include thousands of structures, allow for versatility in 4-position, 4. 5 di-substitution, and cyclic variations. Several cyclic arrangements were proposed to increase rigidity and polymeric free volume, which in turn enhances the subsequent membrane properties in natural gas upgrading.

In sum, the present disclosure teaches using a reductive Mizoroki-Heck reaction applied to substituted norbornenes that yield solely exo norbornene monomers to overcome difficulties endemic to endo isomers. Postulated mechanisms of this reaction show norbornadiene insertion with exo face selectivity into aryl-Pd-halide intermediates, which later reductively eliminate to form solely exo substituted norbornenes and tricyclononenes. Increased stereoregularity provides improvements in gas permeability and also yield important consequences on fields that desire more uniform stereoregularity, especially the life sciences. The use of the Mizoroki-Heck reaction can be utilized to produce several exo-selective norbornene monomers with varying substituents, including trimethylsilyl groups to confer backbone rigidity and improved gas transport properties or propoxy groups to imbue alkoxy ether content promoting polymeric solubility. These monomers produced exo-selective ROMP and addition-type polynorbornenes at yields up to 100% and molecular weights up to 1.8 MDa. Furthermore, the Applicant has demonstrated via XRD that several of these polymers have regimes of frustrated chain-packing that enable solubility-controlled NGL separations. The addition-type tricyclononene polymer with trimethylsilyl substituents achieved higher C4H10/CH4 selectivity performance compared to both addition-type alkoxysilyl polynorbornenes and commercially used rubbery PDMS membranes.

The synthetic methods and full characterization of these materials (NMR, FTIR, TGA, GPC, XRD, EA) is disclosed herein including the appended figures.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for forming a Mizoroki-Heck derived polynorbornene that is suitable for use as a gas separation membrane comprising:
   producing a substituted norbornene monomer by a Mizoroki-Heck coupling reaction in the presence of a catalyst; and
   polymerizing the substituted norbornene monomer to form the Mizoroki-Heck derived polynorbornene, wherein the polymerizing comprises an addition polymerization and is represented by the following synthesis route:

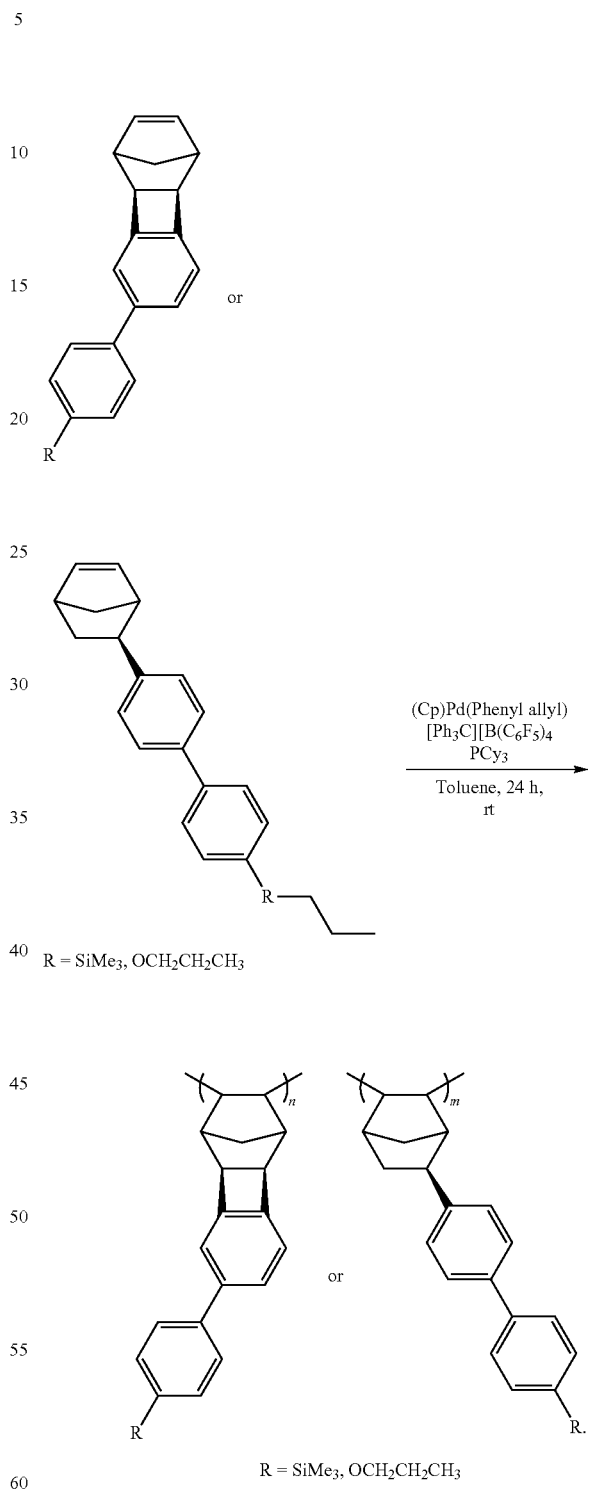

R = SiMe$_3$, OCH$_2$CH$_2$CH$_3$

R = SiMe$_3$, OCH$_2$CH$_2$CH$_3$

2. The process of claim 1, wherein producing the substituted norbornene monomer is represented by the following synthesis route:

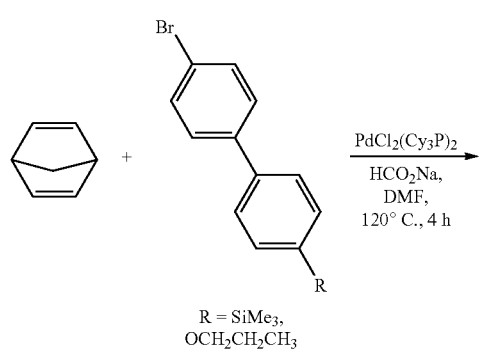

3. The process of claim 1, wherein producing the substituted norbornene monomer is represented by the following synthesis route:

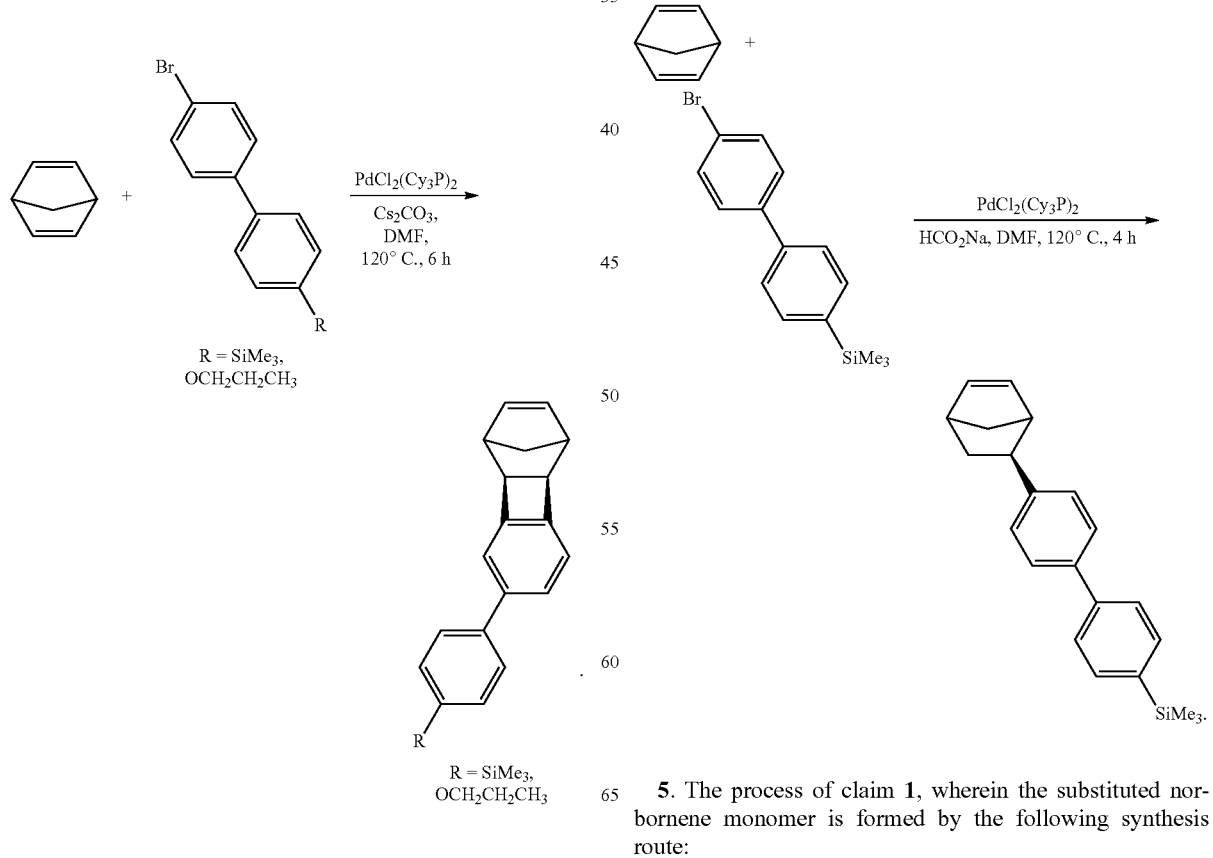

4. The process of claim 1, wherein the substituted norbornene monomer is formed by at least one of the following synthesis routes:

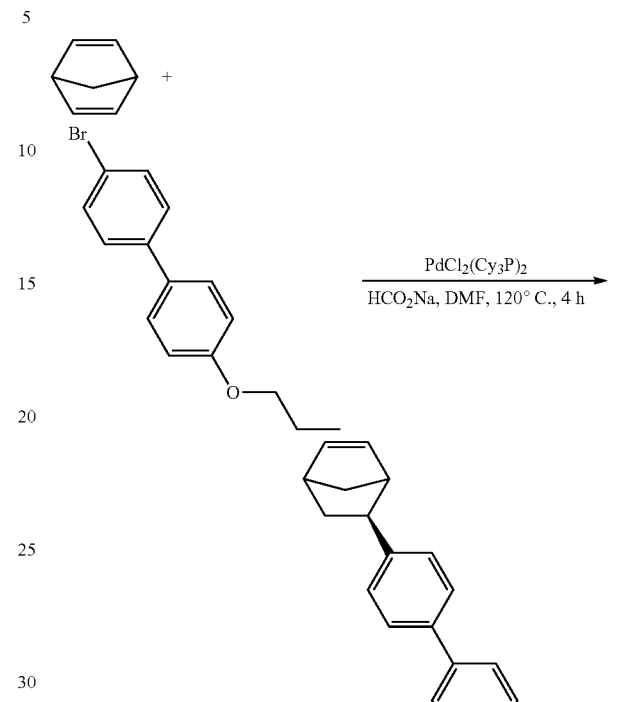

5. The process of claim 1, wherein the substituted norbornene monomer is formed by the following synthesis route:

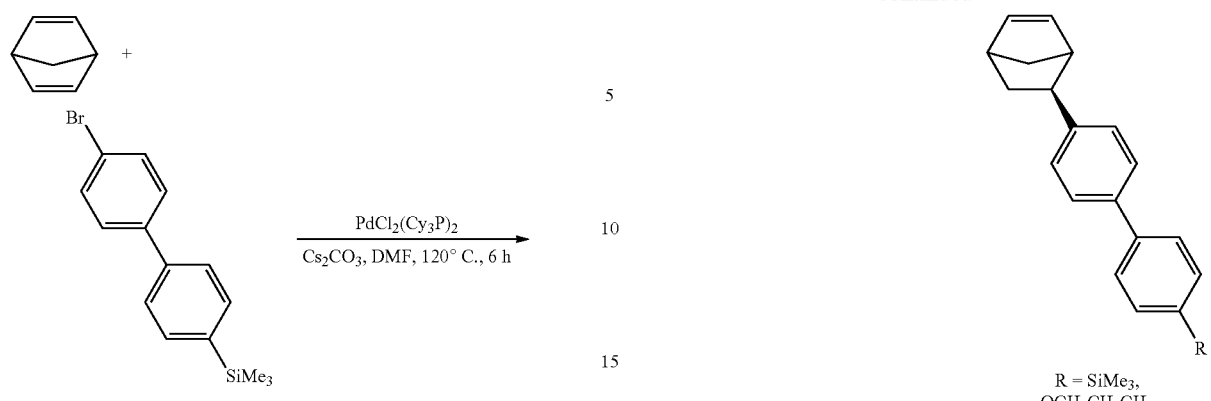

6. A gas separation membrane comprising:

a Mizoroki-Heck derived polynorbornene, wherein the Mizoroki-Heck derived polynorbornene is formed by:

producing a substituted norbornene monomer by a Mizoroki-Heck coupling reaction in the presence of a catalyst; and polymerizing the substituted norbornene monomer to form the Mizoroki-Heck derived polynorbornene, and wherein the polymerizing comprises a ring opening metathesis polymerizing (ROMP), which utilizes a Grubbs 1$^{st}$ Generation catalyst, or any later generation of Grubbs catalyst, wherein producing the substituted norbornene monomer is represented by at least one of the following synthesis routes:

7. The gas separation membrane of claim 6, wherein the substituted norbornene monomer is formed by at least one of the following synthesis routes:

-continued
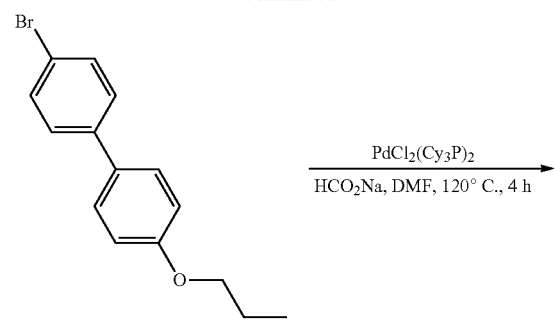
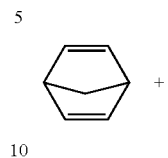
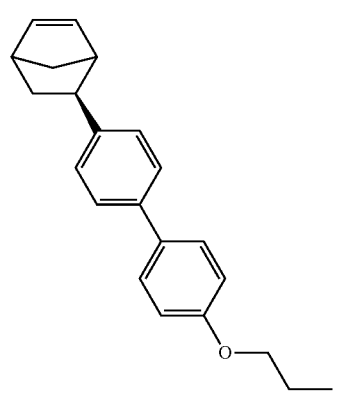
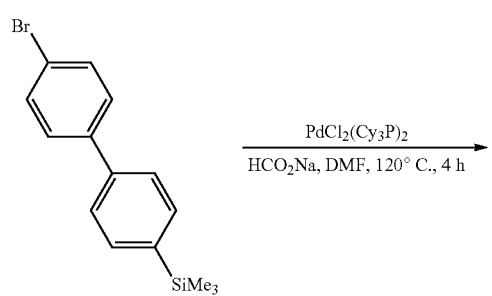
8. The gas separation membrane of claim 6, wherein the substituted norbornene monomer is formed by the following synthesis route:
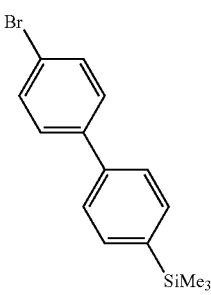
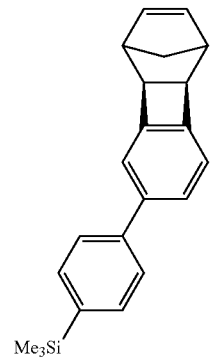
9. The gas separation membrane of claim 6, wherein the polymerizing is represented by the following synthesis route:
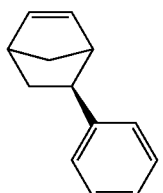
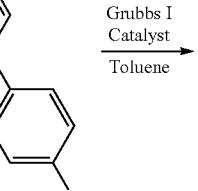
R = SiMe$_3$, OCH$_2$CH$_2$CH$_3$ -continued

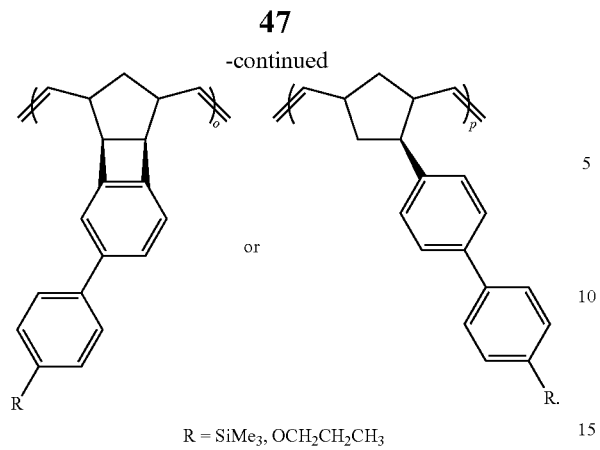

R = SiMe₃, OCH₂CH₂CH₃

-continued

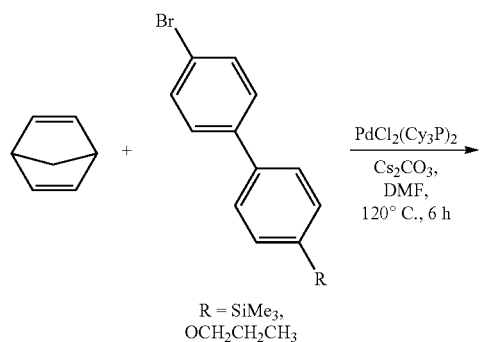

R = SiMe₃, OCH₂CH₂CH₃

10. A process for forming a Mizoroki-Heck derived polynorbornene that is suitable for use as a gas separation membrane comprising:
 producing a substituted norbornene monomer by a Mizoroki-Heck coupling reaction in the presence of a catalyst; and
 polymerizing the substituted norbornene monomer to form the Mizoroki-Heck derived polynorbornene,
wherein producing the substituted norbornene monomer is represented by the following synthesis route:

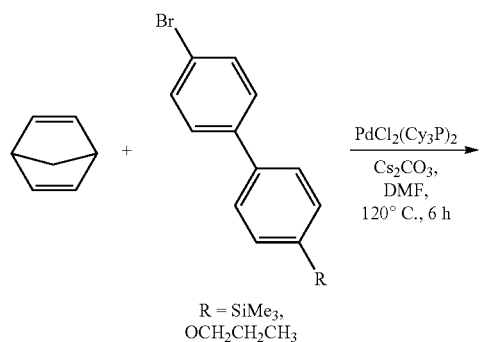

R = SiMe₃, OCH₂CH₂CH₃

11. The process of claim 10, wherein the polymerizing comprises an addition polymerization process.

12. The process of claim 10, wherein the polymerizing comprises a ring opening metathesis polymerizing (ROMP), which utilizes a Grubbs 1$^{st}$ Generation catalyst, or any later generation of Grubbs catalyst.

13. A process for forming a Mizoroki-Heck derived polynorbornene that is suitable for use as a gas separation membrane comprising:
 producing a substituted norbornene monomer by a Mizoroki-Heck coupling reaction in the presence of a catalyst; and
 polymerizing the substituted norbornene monomer to form the Mizoroki-Heck derived polynorbornene,
wherein the substituted norbornene monomer comprises a cyclic substituted norbornene monomer and wherein the cyclic substituted norbornene monomer comprises a cyclobutene Heck monomer.

14. The process of claim 13, wherein the polymerizing step comprises an addition polymerization process.

15. The process of claim 13, wherein the polymerizing comprises a ring opening metathesis polymerizing (ROMP), which utilizes a Grubbs 1$^{st}$ Generation catalyst, or any later generation of Grubbs catalyst.

* * * * *